United States Patent
Uri et al.

(10) Patent No.: US 9,829,434 B2
(45) Date of Patent: Nov. 28, 2017

(54) OPTICAL DETECTION SYSTEM FOR LIQUID SAMPLES

(71) Applicant: Bio-Rad Laboratories Inc., Hercules, CA (US)

(72) Inventors: Yochanan Uri, Givat Elah (IL); Boaz Ran, Haifa (IL); Ariel G. Notcovich, Walnut Creek, CA (US); Shay Nimri, Kibbutz Nir David (IL)

(73) Assignee: Bio-Rad Laboratories Inc., Hercules, CA (US)

( * ) Notice: Subject to any disclaimer, the term of this patent is extended or adjusted under 35 U.S.C. 154(b) by 0 days.

(21) Appl. No.: 15/070,211

(22) Filed: Mar. 15, 2016

(65) Prior Publication Data

US 2016/0299070 A1    Oct. 13, 2016

Related U.S. Application Data

(63) Continuation of application No. 13/911,115, filed on Jun. 6, 2013, now Pat. No. 9,354,179.

(60) Provisional application No. 61/657,818, filed on Jun. 10, 2012.

(51) Int. Cl.
| | |
|---|---|
| *G01N 21/01* | (2006.01) |
| *G01N 21/65* | (2006.01) |
| *G01N 21/25* | (2006.01) |
| *G01N 21/552* | (2014.01) |
| *G01N 33/543* | (2006.01) |
| *G01N 21/03* | (2006.01) |

(52) U.S. Cl.
CPC ......... *G01N 21/553* (2013.01); *G01N 21/253* (2013.01); *G01N 21/658* (2013.01); *G01N 33/54373* (2013.01); *G01N 2021/0328* (2013.01); *G01N 2201/0407* (2013.01); *G01N 2201/0484* (2013.01); *G01N 2201/062* (2013.01)

(58) Field of Classification Search
CPC ........................... G01N 21/553; G01N 21/658
See application file for complete search history.

(56) References Cited

U.S. PATENT DOCUMENTS

| | | | |
|---|---|---|---|
| 4,240,751 | A | 12/1980 | Linnecke et al. |
| 5,313,264 | A | 5/1994 | Ivarsson et al. |
| 5,436,161 | A | 7/1995 | Bergstrom et al. |
| 5,858,799 | A | 1/1999 | Yee et al. |
| 6,139,797 | A | 10/2000 | Suzuki et al. |
| 6,480,282 | B1 | 11/2002 | Chinowsky et al. |

(Continued)

FOREIGN PATENT DOCUMENTS

| | | |
|---|---|---|
| EP | 1054250 | 11/2000 |
| EP | 2230514 | 9/2010 |

(Continued)

OTHER PUBLICATIONS

Advisory Action Before the Filing of an Appeal Brief dated Dec. 24, 2015 From the U.S. Appl. No. 13/911,115.

(Continued)

*Primary Examiner* — Paul Hyun

(57) ABSTRACT

A tip for use in an optical detection system to analyze an analyte in a fluid sample drawn into the tip, using light reflected from a detection surface inside the tip that the analyte binds to, comprising a first detection surface and a second detection surface located in a same flow path with no controllable valve separating them, wherein the first and second detection surfaces have different surface chemistries.

16 Claims, 29 Drawing Sheets

(56) References Cited

U.S. PATENT DOCUMENTS

| | | | |
|---|---|---|---|
| 6,858,423 | B1 | 2/2005 | Abbott et al. |
| 7,394,547 | B2 | 7/2008 | Tan et al. |
| 7,582,487 | B2 | 9/2009 | Malmqvist et al. |
| 7,879,619 | B2 | 2/2011 | Jing et al. |
| 2003/0087292 | A1 | 5/2003 | Chen et al. |
| 2003/0133640 | A1 | 7/2003 | Tiefenthaler |
| 2004/0159798 | A1 | 8/2004 | Martin et al. |
| 2004/0186359 | A1 | 9/2004 | Beaudoin et al. |
| 2004/0241872 | A1 | 12/2004 | Wegrzyn et al. |
| 2005/0059166 | A1 | 3/2005 | Markes |
| 2005/0079520 | A1 | 4/2005 | Wu et al. |
| 2006/0146333 | A1 | 7/2006 | Hakamata et al. |
| 2006/0147941 | A1 | 7/2006 | Su |
| 2006/0147943 | A1 | 7/2006 | Lewis |
| 2007/0082408 | A1 | 4/2007 | Jing et al. |
| 2010/0103421 | A1 | 4/2010 | Johansen et al. |
| 2013/0330230 | A1 | 12/2013 | Uri et al. |

FOREIGN PATENT DOCUMENTS

| | | |
|---|---|---|
| JP | 09-257806 | 10/1997 |
| WO | WO 98/32002 | 7/1998 |
| WO | WO 2007/049269 | 5/2007 |
| WO | WO 2010/077605 | 7/2010 |
| WO | WO 2013/186672 | 12/2013 |

OTHER PUBLICATIONS

Applicant-Initiated Interview Summary dated Mar. 19, 2015 From the U.S. Appl. No. 13/911,115.
Communication Relating to the Results of the Partial International Search dated Oct. 10, 2013 From the International Searching Authority Re. Application No. PCT/IB2013/054660.
International Preliminary Report on Patentability dated Dec. 24, 2014 From the International Bureau of WIPO Re. Application No. PCT/IB2013/054660.
International Search Report and the Written Opinion dated Dec. 20, 2013 From the International Searching Authority Re. Application No. PCT/IB2013/054660.
Notice of Allowance dated Feb. 1, 2016 From the U.S. Appl. No. 13/911,115.
Official Action dated Sep. 17, 2015 From the U.S. Appl. No. 13/911,115.
Official Action dated Jun. 24, 2014 From the U.S. Appl. No. 13/911,115.
Official Action dated Jan. 29, 2015 From the U.S. Appl. No. 13/911,115.
Berger et al. "Surface Plasmon Resonance Multisensing", Analytical Chemistry, 70(4): 703-706, Feb. 15, 1998.
Corning "Corning® Epic® System", Corning Life Sciences, 2 P.
Fortebio "BLI Technology", Fortebio, Retrieved From the Internet, 2 P.
Homola "Surface Plasmon Resonance Sensors for Detection of Chemical and Biological Species", Chemical Reviews, 108: 462-493, 2008.
Lata et al. "Stable and Functional Immobilization of Histidine-Tagged Proteins Via Multivalent Chelator Headgroups on a Molecular Poly(Ethylene Glycol) Brush", Analytical Chemistry, 77(4): 1096-1105, Feb. 15, 2005.
Loefas et al. "A Novel Hydrogel Matrix on Gold Surfaces in Surface Plasmon Resonance Sensors for Fast and Efficient Covalent Immobilization of Ligands", Journal of the Chemical Society, Chemical Communications, 21: 1526-1528, 1990.
Loefas et al. "Methods for Site Controlled Coupling to Carboxymethyldextran Surfaces in Surface Plasmon Resonance Sensors", Biosensors & Bioelectronics, 10: 813-822, 1995.
Rich et al. "Survey of the Year 2005 Commercial Optical Biosensor Literature", Journal of Molecular Recognition, 19: 478-534, 2006.
SRU Biosystems "BIND Technology", SRU Biosystems, Inc., 3 P., 2000-2011.
Communication Pursuant to Article 94(3) EPC dated Sep. 19, 2016 From the European Patent Office Re. Application No. 13736975.7.
Communication Pursuant to Article 94(3) EPC Dated Aug. 1, 2017 From the European Patent Office Re. Application No. 13736975.7. (6 pages).

OPTICAL DETECTION SYSTEM FOR LIQUID SAMPLES

RELATED APPLICATIONS

This application is a continuation of U.S. patent application Ser. No. 13/911,115 filed Jun. 6, 2013, now U.S. Pat. No. 9,354,179 which claims the benefit of priority under 35 U.S.C. §119(e) of U.S. Provisional Patent Application No. 61/657,818 filed Jun. 10, 2012, the contents of which are incorporated herein by reference in their entirety.

This application is also related to co-filed, co-pending and co-assigned PCT Patent Application Number PCT Patent Application No. PCT/IB2013/054660 having International Filing Date of Jun. 6, 2013, entitled "OPTICAL DETECTION SYSTEM FOR LIQUID SAMPLES" by Yochanan Uri, Boaz Ran, Ariel G. Notcovich and Shay Nimri, the disclosure of which is incorporated herein by reference.

FIELD AND BACKGROUND OF THE INVENTION

The present invention, in some embodiments thereof, relates to an optical detection system for liquid samples, and, more particularly, but not exclusively, to a surface plasmon resonance (SPR) system for biological assays in well plates.

Optical detection systems can be useful for detecting and measuring various target molecules, including biological analytes, or small molecules such as drugs, in a fluid sample of very small volume, as well as for studying the reaction dynamics of such target molecules with ligand molecules that they bind to. As used herein, the target molecule will be referred to as an analyte. Typically, in such a system, the fluid sample is in contact with an active surface that is coated with a ligand that binds to the analyte of interest, creating a thin layer on the surface if the analyte is present, with the rate of increase of thickness of the layer depending on the concentration of the analyte in the sample, as well as on reaction constants between the analyte and the ligand, and the surface density of the ligand. The thickness of the layer, or an effective thickness if the layer is not uniform, can be measured with great sensitivity by reflecting light from the back of the surface, and measuring the reflectance as a function of angle of incidence for a given wavelength, and/or the reflectance as a function of wavelength for a given angle of incidence. In surface plasmon resonance (SPR) detection systems, the surface is an SPR surface, coated with a thin film of a metal, such as gold, that exhibits SPR, in which the reflectance has a narrow dip near a particular angle of incidence, due to surface plasmons that are generated in the thin film of metal at that angle of incidence. The angle of incidence of maximum absorption depends sensitively on the thickness of the layer of analyte on the surface. Other optical detection methods, which can be used in such an optical detection system, include ellipsometry, total internal reflection, Brewster angle measurements, thin film interferometry, and spectroscopy from nanoparticles and from nanostructured optical gratings.

Jiri Homola, "Surface Plasmon Resonance Sensors for Detection of Chemical and Biological Species," *Chem. Rev.* 108, 462-493 (2008) provides a review of the literature on SPR sensors and their uses. Rebecca L. Rich and David Myszka, "Survey of the year 2005 commercial optical biosensor literature," *Journal of Molecular Recognition* 19, 478-534 (2006), reviews some of the applications of optical detection systems for studying the reaction kinetics of biomolecules.

U.S. Pat. No. 7,582,487 to Malmqvist et al describes an SPR system that uses microfluidic channels, with individually controlled valves, as well as a system using laminar flow techniques, to position a fluid flow over a discrete sensing area of a sensing surface. One sensing area can be sensitized by exposure to an analyte-specific ligand, while one or more non-sensitized areas can be used as a reference area, or sensitized with a control ligand. Such a microfluidic SPR system with active sensing areas and a reference area is also described, for example, in Charles E. H. Berger, Tom A. M. Beumer, Rob P. H. Kooyman, and Jan Greve, "Surface Plasmon Resonance Multisensing," *Anal. Chem.* 70, 703-706 (1998), and a microfluidic SPR system is also described in U.S. Pat. No. 5,313,264 to Ivarsson.

WO98/32002 to Jorgenson et al describes an SPR-based fiber optic sensor in which a layer of an SPR supporting metal is deposited around an exposed area of a fiber optic core. A sample-drawing device such as a pipette temporarily receives the sensor for use during a sampling or testing procedure.

US2004/0186359 to Beaudoin et al describes an in vivo SPR probe surface with two regions. One region has an immobilized binding member on it that binds specifically to a marker being monitored, and the other region does not. Light from the two regions can be compared, in order to determine the presence or absence of the marker.

U.S. Pat. No. 6,480,282 to Chinowsky et al describes an SPR sensor, in which at least a portion of the inside surface of a capillary tube is an SPR surface, and samples for analysis are introduced into the capillary tube.

US2010/0103421 to Johansen et al describes a transparent wall of a cavity with a concave inner surface provided with a layer of conductive material capable of supporting SPR. There is a flow structure with one or more channels, through which a sample can flow in contact with the SPR surface, and SPR measurements are made.

U.S. Pat. No. 6,139,797 to Suzuki et al describes an immunoassay apparatus with optical fibers, each with an end serving as an SPR sensor. The end portion of the apparatus, with the SPR sensors, is disposable. Multiple fibers with different SPR sensors can be used, which can serve as positive or negative controls to distinguish specific from non-specific binding.

Japanese published Patent application JP9257806 to Uchiyama et al describes an SPR sensor apparatus, in which a disposable hollow needle is used to suck up a sample solution, and an SPR metal film is vapor-deposited on the light reflecting face of a prism at the needle.

Methods of chemically treating SPR surfaces, so that an analyte-specific ligand can be immobilized on them, are described, for example, in: U.S. Pat. No. 5,436,161 to Bergström et al; Stefan Lofas and Bo Johnsson, "A Novel Hydrogel Matrix on Gold Surfaces in Surface Plasmon Resonance Sensors for Fast and Efficient Covalent Mobilization of Ligands," *J. Chem. Soc., Chem. Commun.* (1990), 1526-1528; Stefan Lofas et al, "Methods for site controlled coupling to carboxymethyldextran surfaces in surface plasmon resonance sensors," *Biosensors & Bioelectronics* 10 (1995), 813-822; and in published PCT application WO 2007/049269, "Binding Layer and Methods for its Preparation and Uses Thereof," assigned to Bio-Rad Haifa, Ltd., and with Shay Nimri as the inventor, with the same assignee and one of the same inventors as the present application.

Bio-layer interferometry (BLI), another optical detection technique, is described on the website of Forte-Bio, www-dotfortebiodotcom/bli_technologydothtml, downloaded on Jan. 19, 2012.

The EPIC® system, an optical sensor system based on a refractive waveguide grating, is described on the website of Corning Life Sciences, at wwwdotcorningdotcom/life-sciences/epic/en/products/epic_systemdotaspx, downloaded on Mar. 1, 2012. Another optical detection system based on an optical grating, the BIND® system, is described on the website of SRU Biosystems, at wwwdotsrubiosystemsdot-com/technology/indexdothtml, downloaded on Mar. 1, 2012.

Additional background art includes EP1054250 to Taguchi et al, U.S. Pat. No. 7,394,547 to Tan et al, WO2010/077605 to Xiao et al, U.S. Pat. No. 4,240,751 to Linnecke et al, U.S. Pat. No. 5,858,799 to Yee et al, and U.S. Pat. No. 7,271,885 to Schermer.

SUMMARY OF THE INVENTION

An aspect of some embodiments of the invention concerns a tip for use in a surface plasmon resonance (SPR) well detection system, and a method of manufacturing such a tip, that is inexpensive enough, when mass produced, for the tip to be disposable. The invention is applicable also to other optical detection techniques involving reflection of light from a surface that an analyte adheres to from a fluid sample.

There is thus provided, in accordance with an exemplary embodiment of the invention, a tip for use in an optical detection system to analyze an analyte in a fluid sample drawn into the tip, using light reflected from a detection surface inside the tip that the analyte binds to, comprising a first detection surface and a second detection surface located in a same flow path with no controllable valve separating them, wherein the first and second detection surfaces have different surface chemistries.

Optionally, the detection surfaces are SPR surfaces.

There is further provided, in accordance with an exemplary embodiment of the invention, an SPR detection system comprising a tip according to an exemplary embodiment of the invention, adapted to use SPR to detect the analyte on at least one of the detection surfaces that the analyte binds to, when a fluid sample comprising the analyte is drawn into the tip.

There is further provided, according to an exemplary embodiment of the invention, an optical detection system comprising a tip according to an exemplary embodiment of the invention, adapted to use one or more of ellipsometry, total internal reflection (TIR) detection, Brewster angle detection, and thin-film interferometry, to detect the analyte on at least one of the detection surfaces that the analyte binds to, when a fluid sample comprising the analyte is drawn into the tip.

Optionally, the second detection surface has a surface chemistry that does not allow it to bind to a ligand that binds to the analyte, while the first detection surface has a surface chemistry that allows it to bind to the ligand.

Optionally, the ligand binds to the first detection surface by an amine group of the ligand forming a covalent bond with an active functional group of the first detection surface, while the second detection surface has a surface chemistry with functional groups that do not form a covalent bond with the amine group of the ligand.

Optionally, the active functional group of the first detection surface comprises one or more of active carboxylic ester, epoxide, aldehyde, and acrylate.

Additionally, the functional groups of the second detection surface comprise one or more of hydroxyl, alkyl ester, carboxylic acid, sulfate, sulfonate and phosphonate.

Alternatively, the first detection surface, but not the second detection surface, comprises a capturing agent for affinity-based binding of the ligand.

Optionally, the capturing agent comprises one or more of: avidin or an avidin derivative with a high affinity to biotin; a molecule with a high affinity to an antibody molecule; and a molecule with a high affinity to a recombinant protein tag.

There is further provided, in accordance with an exemplary embodiment of the invention, an optical detection system for simultaneously analyzing one or more analytes in fluid samples in a plurality of different wells of a well plate, the system comprising:
  a) a reading head holding an array of tips according to an exemplary embodiment of the invention, spaced to allow the tips to simultaneously draw in fluid from the plurality of different wells;
  b) an optical sub-system associated with each tip, each sub-system comprising one or more light sources, illuminating optics to direct light from the one or more light sources to reflect from the first and second detection surfaces at a range of angles of incidence, a detector array associated with each of the first and second detection surface, and detecting optics to direct light reflected from the first and second detection surfaces to different elements of the corresponding detector arrays, according to an angle of reflectance of the light.

Optionally, at least some of the tips are arranged to draw in the fluid samples to flow in a flow direction that is substantially parallel in all of those tips, the first and second detection surfaces are arranged along the flow direction in each of those tips, and the illuminating optics for the sub-system for each of those tips directs light to the first and second detection surfaces along paths that are substantially the same but displaced from each other in the flow direction.

Optionally, at least some of the tips are arranged to draw in the fluid samples to flow in a flow direction that is substantially parallel in all of those tips, the first and second detection surfaces are arranged along the flow direction in each of those tips, and the receiving optics for the sub-system of each of those tips directs light from the first and second detection surfaces along paths that are substantially the same but displaced from each other in the flow direction.

Optionally, at least some of the tips are arranged to draw in the fluid samples to flow in a flow direction that is substantially parallel in all of those tips, and the illuminating optics for each of those tips directs at least some of the light in a path that is substantially perpendicular to the flow direction.

Optionally, at least some of the tips are arranged to draw in the fluid samples to flow in a flow direction that is substantially parallel in all of those tips, and the receiving optics for each of those tips directs at least some of the light in a path that is substantially perpendicular to the flow direction.

Alternatively, at least some of the tips are arranged to draw in the fluid samples to flow in a flow direction that is substantially parallel in all of those tips, and the receiving optics for each of those tips comprises an element that directs at least some of the light from a path substantially perpendicular to the flow direction to a path substantially parallel to the flow direction.

There is further provided, in accordance with an exemplary embodiment of the invention, a method of preparing a tip for an optical detection system that analyzes an analyte in a fluid sample drawn into the tip, using light reflected from a detection surface inside the tip that the analyte binds to, the method comprising:
a) providing at least one detection surface outside the tip;
b) chemically preparing the detection surface to be suitable for use in the optical detection system; and
c) assembling the prepared detection surface permanently into the tip.

Optionally, the optical detection system is an SPR system, and preparing the detection surface comprises coating the detection surface with a metal film suitable for SPR.

Additionally or alternatively, preparing the detection surface comprises providing the detection surface with a surface chemistry that can bind to a ligand that the analyte binds to.

In an exemplary embodiment of the invention, preparing the detection surface comprises:
a) making an array of attached surface elements;
b) chemically preparing the surface of the array to be suitable for use in the optical detection system;
c) breaking the array into separate surface elements after the surface of the array has been chemically prepared; and
d) assembling at least two different surface elements from the array into two different tips.

Optionally, the array comprises at least 100 of the surface elements.

Optionally, the array comprises at least 1000 of the surface elements.

Optionally, the surface elements comprise glass.

Optionally, the surface elements comprise a polymer.

Additionally or alternatively, the surface elements comprise a prism.

Alternatively, the surface elements do not comprise a prism, and assembling each surface element into a tip comprises assembling the surface element with a prism.

Optionally, the method also comprises:
a) making an array of attached prisms; and
b) breaking the array of attached prisms into separate prisms;
wherein assembling each surface element with a prism comprises assembling each surface element with one of the prisms from the array of prisms, and assembling each surface element into a tip comprises assembling the combined prism and surface element into the tip.

Optionally, the at least one detection surface comprises a first detection surface and a second detection surface, chemically preparing comprises applying a chemical treatment to at least one of the detection surfaces that is not applied to the other detection surface, and assembling comprises assembling the first and second detection surfaces permanently into the tip, after applying the chemical treatment.

Optionally, the difference in chemical treatment of the first and second detection surfaces causes the second detection surface not to bind to a ligand that the analyte binds to, but makes the first detection surface capable of binding to the ligand.

Optionally, the method also comprises exposing both the first and second detection surfaces to the ligand after assembling the first and second detection surfaces into the tip, thereby binding the ligand to the first detection surface and not to the second detection surface.

Optionally, the method also comprises detecting the analyte in the tip, using the optical system with the first detection surface as the detection surface that the analyte binds to, after the ligand has been bound to the first detection surface, and using the second detection surface as a reference surface for the optical system.

Optionally, the first and second detection surfaces have similar non-specific binding properties to other substances in the fluid sample.

There is further provided, in accordance with an exemplary embodiment of the invention, a tip for use in an optical detection system to analyze an analyte in a fluid sample drawn into the tip, using light reflected from a detection surface inside the tip that the analyte binds to, the tip comprising:
a) a flow chamber with a proximal end, a distal portion, and an opening on the side, the flow chamber being attached to a nozzle on the proximal end for inserting into the fluid sample, and to an aspiration system on the distal portion for drawing in the fluid sample when the nozzle is inserted into the fluid sample;
b) the detection surface, made separately from the flow chamber and assembled into the flow chamber through the opening; and
c) a seal that seals the opening, comprising a channel through which the fluid sample flows along the detection surface when the aspiration system draws the fluid sample in, when the opening is sealed.

Optionally, a portion of the seal surrounding the channel is configured to rest against a portion of the detection surface, when the opening is sealed.

Optionally, the tip also comprises a reference surface, and the channel is configured so that the fluid sample flows through the channel past both the detection and reference surfaces, when the aspiration system draws the fluid sample in, when the opening is sealed.

Optionally, the detection surface is an SPR surface.

There is further provided, in accordance with an exemplary embodiment of the invention, a tip for use in an optical detection system that analyzes an analyte in a fluid sample drawn into the tip, using light reflected from a detection surface inside the tip that the analyte binds to, the tip comprising the detection surface with a ligand bound to it that the analyte binds to, and a reference surface without the ligand bound to it, separate from the detection surface.

There is further provided, in accordance with an exemplary embodiment of the invention, a method of preparing a detection surface for use in an optical detection system that analyzes an analyte in a fluid sample using light reflected from the detection surface after it is prepared so that the analyte binds to it, the method comprising:
a) providing a first detection surface and a second detection surface; and
b) chemically treating only the first or only the second detection surface, or chemically treating the first detection surface differently than the second detection surface, such that the first detection surface, but substantially not the second detection surface, is capable of binding to a ligand that is capable of binding to the analyte, but the first and second detection surfaces have surface chemistries that give them similar non-specific binding properties to the analyte and other materials in the fluid sample.

Optionally, the method also comprises exposing both the first and second detection surfaces to the ligand, so that the ligand binds to the first detection surface but substantially not to the second detection surface.

There is further provided, in accordance with an exemplary embodiment of the invention a tip for use in an optical detection system to analyze an analyte in a fluid sample drawn into the tip, by reflecting light from a detection surface inside the tip that the analyte binds to, comprising a first detection surface with a surface chemistry such that the surface binds to a ligand that binds to the analyte, and a second detection surface with a surface chemistry such that the surface does not bind to the ligand, wherein the surface chemistries of the first and second detection surfaces are similar enough so that the analyte and other materials in the fluid sample bind non-specifically to the first and second detection surfaces at a similar rate.

There is further provided, in accordance with an exemplary embodiment of the invention, a method of preparing a tip for an optical detection system for analyzing an analyte in a fluid sample drawn into the tip, using light reflected from a detection surface inside the tip that the analyte binds to, the method comprising:
- a) providing first and second detection surfaces outside the tip, suitable for use in the optical system;
- b) applying a chemical treatment to at least one of the detection surfaces that is not applied to the other detection surface; and
- c) assembling the first and second detection surfaces into the tip, after applying the chemical treatment.

There is further provided, in accordance with an exemplary embodiment of the invention, a method of assembling a tip for use in an optical detection system that analyzes an analyte in a fluid sample drawn into the tip, using light reflected from a detection surface inside the tip that the analyte binds to, the method comprising:
- a) providing a first module containing a flow chamber with a first detection surface, the module attached at its proximal end to a detachable nozzle;
- b) drawing into the nozzle and at least up to the first detection surface a fluid containing a ligand that binds to the analyte, such that the ligand binds to the first detection surface, preparing the first detection surface to be the detection surface that the analyte binds to;
- c) covering the first detection surface with a buffer solution, after the ligand is bound to it;
- d) detaching the nozzle from the first module, keeping the first detection surface covered with the buffer solution;
- e) attaching a second module, containing a flow chamber with a second detection surface, without the ligand bound to it, to the proximal end of the first module, the second detection surface functioning as a reference surface; and
- f) attaching the same or a different nozzle to a proximal end of the second module.

Optionally, the first and second detection surfaces are SPR surfaces, and the optical detection system analyzes the analyte using SPR.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
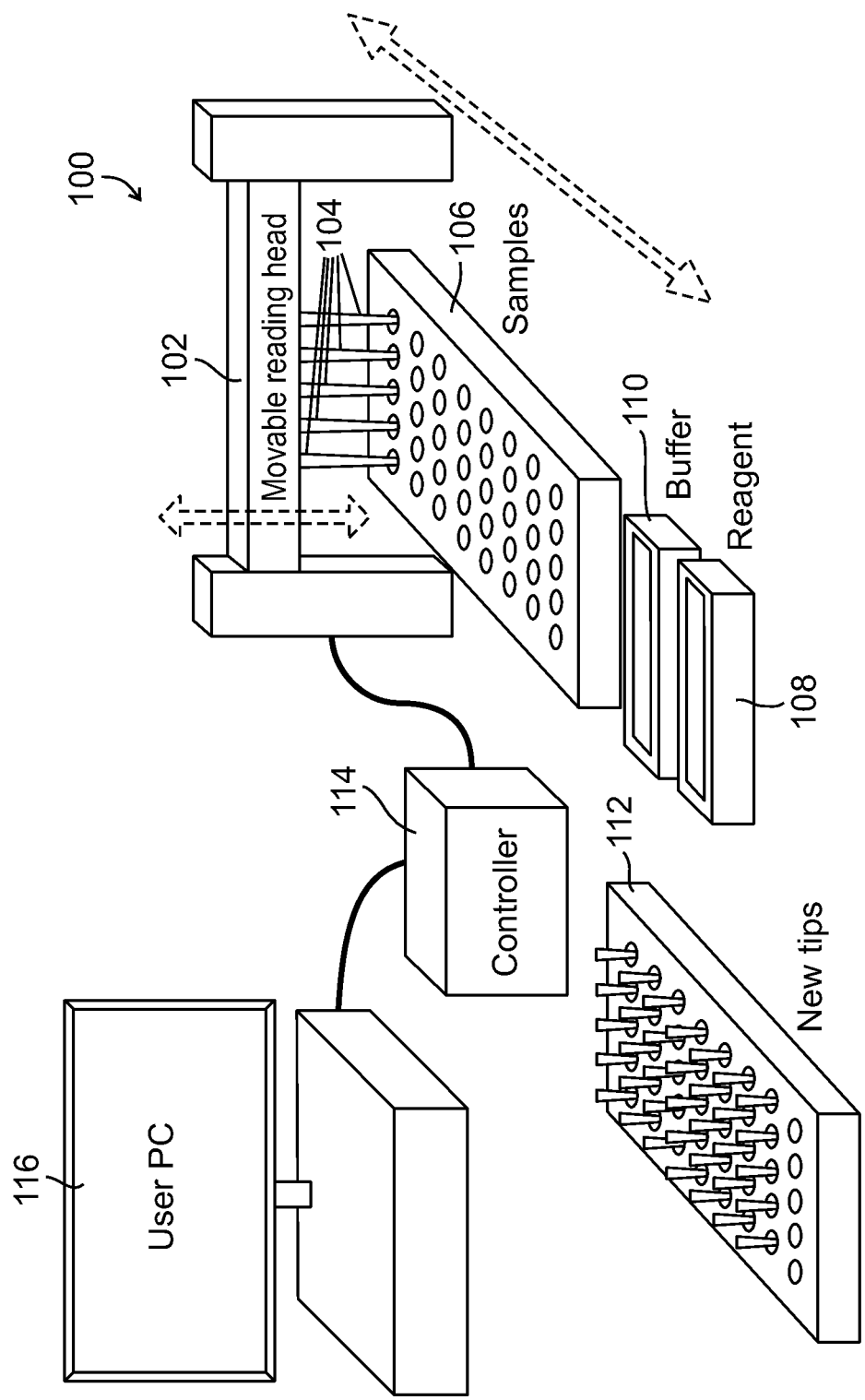
FIG. 1A is a schematic perspective view of an SPR system for analyzing an array of fluid samples in a well plate, with a row of SPR tips for analyzing one row of the fluid samples at a time, according to an exemplary embodiment of the invention.

The present invention, in some embodiments thereof, relates to an optical detection system for liquid samples in well plates, and, more particularly, but not exclusively, to a surface plasmon resonance (SPR) system for biological assays.

An aspect of some embodiments of the invention concerns a single tip, for an optical detection system that detects an analyte by reflecting light from a detection surface that the analyte binds to. The tip has at least two different detection surfaces, prepared separately with different surface chemistries, and then assembled into the tip. As used herein, a tip means a device for drawing in a fluid sample, for example from a well in a well plate, and exposing it to a detection surface, which is coated with a ligand that an analyte of interest, which may be found in the fluid sample, adheres to. In the case of an SPR system, the detection surface is an SPR surface. By measuring light, directed into the tip and reflected from the surface, during or after the time it is exposed to the fluid sample, very small quantities of the analyte may be detected, and/or reaction kinetics of the analyte may be measured, due to changes in the thickness of a film on the surface when it is exposed to the analyte. Furthermore, optionally the fluid sample can be returned to the well from the tip after it is analyzed, and later re-used, for example by drawing it into another tip to detect a different analyte. Such re-use of the fluid sample further reduces the volume of the fluid sample needed, compared to a microfluidic SPR system in which fluid samples cannot easily be re-used.

It should be understood that an optical detection system, as described above, can be used for detecting the presence and/or measuring the concentration of an analyte in a fluid sample, when its presence or concentration is not known in advance, as well as for studying the reaction kinetics of an analyte of known concentration in a fluid sample, with a ligand on the detection surface. In all these cases, the terms "detection system", "detection technique," and "detection surface" are used herein. It should be understood that when a detection system is described herein as being used to detect an analyte, it can also be used to measure the concentration of the analyte, and/or to study the reaction kinetics of the analyte. The terms "analyze a sample" or "analyze an analyte" include all of these uses of an optical detection system.

Optionally, an array of many tips is used to simultaneously analyze samples from many different wells in a well plate, with each tip drawing in a fluid sample from a different well.

Aspects of the invention, as described herein, are generally applicable to a variety of sensitive optical detection techniques, for analytes that adhere to a surface, using light reflecting from the surface. These detection techniques include, but are not limited to, surface plasmon resonance (SPR), ellipsometry, total internal reflection, Brewster angle measurements, thin film interferometry, including bio-layer interferometry (BLI), and spectroscopy from nanoparticles and from nanostructured optical gratings, such as the BIND® system sold by SRU Biosystems, or the Epic® system sold by Corning. For convenience, the exemplary embodiments described herein generally refer to SPR systems and SPR surfaces, but it should be understood that these embodiments can be implemented with these other detection techniques as well. Systems using these other techniques will generally differ from SPR systems in using different types of surfaces, different ranges of angles of reflection, and in some cases light sources with different ranges of wavelengths. For example, spectroscopy methods may use broader ranges of wavelengths than the other techniques, which may use relatively monochromatic light sources.

As used herein, "surface chemistry" refers to the chemical composition of the detection surface before the ligand has been bound to it. Specific ligands, used for detecting or studying specific analytes, may or may not bind to an SPR surface, depending on its surface chemistry. By preparing a single tip containing two SPR surfaces with different suitable surface chemistries, a fluid containing a desired ligand can be drawn into the tip, and it will only bind to one of the SPR surfaces. The tip can then be used to detect an analyte that adheres to that ligand, using one of the SPR surfaces, with the ligand attached to it, as the active detection surface, and the other SPR surface, without the ligand attached, as a reference surface. It is desirable, in an SPR system for detecting an analyte in a fluid sample, to have an active SPR surface and a reference SPR surface, both exposed simultaneously to the sample, and located close to each other. Such a configuration can be useful for distinguishing the effect of the analyte binding to the ligand, from other effects such as changes in temperature, changes in the refractive index of the bulk fluid above the SPR surface, and non-specific binding to the SPR surface of other materials in the fluid sample. In prior art SPR systems, such active surfaces and reference surfaces have been prepared by using microfluidics to expose only one of the SPR surfaces to the ligand. Using two SPR surfaces with different surface chemistries, only one of which binds to the ligand, has the potential advantage that the system may be less expensive than a system using microfluidics.

As used herein, "detection surface" may be used to refer not only to an active detection surface, but to any surface suitable for use by the optical system, including a reference surface, or a detection surface before the ligand has been bound to it, even though the analyte will not bind to a reference surface or to a detection surface that does not yet have the ligand bound to it.

In some embodiments of the invention, there are three or more SPR surfaces with different surface chemistries in the same tip. For example, one of the surfaces is used as a reference surface, and has a surface chemistry that a ligand will not bind to, while two or more of the surfaces are used as active detection surfaces, and have surface chemistries that will bind the same ligand with different surface densities. When a fluid sample flows past the active detection surfaces, the analyte will bind to them at different rates, and measuring these rates on different detection surfaces in the same tip simultaneously can lead to a more accurate measurement of the concentration of the analyte in the fluid sample, or a more accurate measurement of the reaction rate between the analyte and the ligand, as well as being faster than making multiple measurements sequentially in different tips with different surface densities of ligand. Such a "one shot" SPR system is described, for example, in U.S. Pat. No. 8,105,845. Additionally or alternatively, the two or more active surfaces in the same tip have surface chemistries that bind different ligands, which bind to different analytes, and the tip is used to detect two or more different analytes in the same fluid sample, simultaneously. Alternatively, the different ligands bind to the same analyte, and the tip is used to study the reaction kinetics of the analyte with two different ligands, simultaneously.

An aspect of some embodiments of the invention concerns an SPR tip containing at least one SPR surface element that is made separately from the tip, and then assembled permanently into the tip. This can potentially reduce the cost of the tip, because, for example, the tip can be molded inexpensively out of a polymer such as a plastic, while the SPR surface element can be made out of glass, which is often preferable to a polymer because of possible difficulty in obtaining a desired surface chemistry, for binding (or not binding) with a desired ligand, if the SPR surface is made of a polymer. In some embodiments of the invention, even greater cost savings is achieved by using a large array of SPR elements made as a single wafer, with the entire surface of the wafer coated and chemically treated to produce an SPR surface with the desired surface chemistry, and then broken up into individual SPR surface elements, each of which is assembled into a tip. This procedure can save money because the expensive steps of producing the SPR surface and chemically treating it have their cost divided by the number of elements in the array, which can be, for example, over a thousand. Optionally, the SPR surfaces are joined together with prisms, used for the illumination and detection system, which are made separately, and assembled with the SPR surfaces only after the wafer is coated and chemically treated and broken apart into individual SPR surfaces. Optionally, the prisms are made of a polymer and molded or cast in one piece with the tips. Alternatively, the prisms are themselves made from a wafer that is broken into individual prisms, or the SPR surfaces are coated directly on the prisms, and the array of prisms is the array of SPR surfaces.

An aspect of some embodiments of the invention concerns an SPR tip with two or more SPR surfaces, with different surface chemistries, in a single flow path with no controllable valve separating them. The surface chemistries optionally differ in that a ligand, which is capable of binding to an analyte which is to be detected, is capable of binding to one of the surfaces but substantially not to the other. This makes it possible to expose both of the SPR surfaces to the ligand, and have the ligand bind to one of the surfaces, which then functions as an active SPR surface, while the other SPR surface, which the ligand substantially does not bind to, functions as a reference SPR surface.

An aspect of some embodiments of the invention concerns an SPR tip, and a method of preparing it, using two SPR surfaces, the first one chemically treated to form a surface chemistry so that a ligand binds to it, and the second one chemically treated to form a surface chemistry so that the ligand substantially does not bind to it. Both surfaces are exposed to the ligand, and the ligand binds substantially only to the first surface. The first surface then serves as an active SPR surface for an analyte that binds to the ligand, while the second surface serves as a reference surface. Optionally, the second surface has non-specific binding properties that are similar to the first surface.

There are a number of options for chemically treating a first SPR surface to form a surface chemistry so that a ligand binds to it, and for chemically treating a second SPR surface so that the ligand substantially does not bind to it. For example, the ligand binds to the first surface by an amine group of the ligand forming a covalent bond with an active functional group of the first surface, while the second surface has a surface chemistry with functional groups that do not form a covalent bond with the amine group of the ligand. Alternatively, the first surface, but not the second surface, has a capturing agent for affinity-based binding of the ligand.

An aspect of some embodiments of the invention concerns an SPR tip comprising a flow chamber into which a fluid sample is aspirated through a nozzle, the flow chamber containing an SPR surface, made separately from the tip, and assembled into the flow chamber through an opening in its side. After the SPR surface is assembled into the flow chamber, the opening is sealed, using a seal, such as a gasket, which has a flow channel running through it, that directs the aspirated fluid sample to flow along the SPR surface when the seal is in place sealing the opening, the SPR surface forming one side of the channel when the seal is in place. Optionally, at least a portion of the seal, surrounding the channel, rests against the SPR surface, when the seal is in place. Optionally, the channel also directs the fluid sample to flow past a second SPR surface, used as a reference surface.

An aspect of some embodiments of the invention concerns a method of preparing an SPR tip, for use in an SPR system for detecting an analyte in a fluid sample. The SPR tip comprises a first flow chamber module with a first SPR surface in it, and a nozzle attached to the proximal end of the first flow chamber module. Fluid containing a ligand, which binds to the analyte, is drawn through the nozzle to the first flow chamber module, where it binds to the first SPR surface. The nozzle is then detached from the first flow chamber module, keeping the first SPR surface covered with a buffer solution, and a second flow chamber module is then attached to proximal end of the first module. The second flow chamber module contains an SPR surface with no ligand bound to it. The same or a different nozzle is then attached to the proximal end of the second flow chamber module. The first SPR surface can then act as an active SPR surface, and the second SPR surface can act as a reference SPR surface, for detecting the analyte in a fluid sample drawn up to the flow chamber modules through the nozzle.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Overview of System and Procedure

Referring now to the drawings, FIG. 1A illustrates an SPR system 100 for analyzing an array of fluid samples in a well plate, according to an exemplary embodiment of the invention. The hardware in three different SPR systems, representing low cost, mid-range, and high cost systems, shown in FIGS. 1A-1D, will be described first, followed by a more detailed description of a method of operation of the systems, in FIG. 2. All of these systems take advantage of the low cost of SPR tips manufactured by the methods to be described below, which may make it practical to use many tips at once, and to use each tip only once, or only a few times, before disposing of it. The low cost of the tips also makes it possible to use the automated operating procedures that are described below, especially in the high end system shown in FIGS. 1C and 1D, to provide a high throughput of testing fluid samples.

System 100 is a relatively low end system, with only a single row of samples analyzed at a time, and with some of the operations of the system done manually. A moveable reading head 102 holds a row of SPR tips 104, that can be lowered into one row of samples in a well plate 106. Alternatively, the reading head is fixed and the well plate is moveable, or they are both moveable. A vacuum system in reading head 102 draws a fluid sample into each tip from the well that it is inserted into. As will be described in more detail below, the tip is optionally configured so that the fluid sample flows in a single channel past both an active SPR surface and a reference SPR surface, when it is drawn into the tip by the vacuum system. Optionally, a single vacuum system is used for all of the tips, which can be less expensive than having a separate vacuum system for each tip. Alternatively, there are different vacuum systems for some tips, or even a separate vacuum system for each tip, for example a separate piston in reading head 102 is used to draw fluid from each well, which has the potential advantage that equal amounts of fluid can be drawn into each well even if the different tips have different resistance to fluid flow. Optionally in that case, a single actuator can control all of the pistons, which is potentially less expensive than having separate actuators for different pistons.

Once the fluid sample has been drawn into the tip, it is analyzed using an optical sub-system that is described below, in the description of FIGS. 3A-3F, with each tip having its own light sources, optical elements, and detector arrays. For clarity, the optical sub-system is not shown in FIGS. 1A-1C. Reading head 102 can be moved along well plate 106, for example manually in the case of this low end system, to draw samples from other rows. The vacuum system of reading head 102 can also be used to draw a reagent from a tray 108 into the tips, for example to bind a ligand to the SPR surface that will bind specifically to an analyte that is being tested for, before drawing in the samples from the well plates. Reagent tray 108, or an additional reagent tray, optionally also has reagents that are used for procedures of the chemical treatment that are done after binding the ligand to the SPR surface, as described below in FIGS. 12A and 12B. A buffer solution in a tray 110 can also be drawn into the tips by the vacuum system, for example to make sure that the SPR surface does not dry out or become exposed to oxygen once the ligand is bound to it, and the chemical treatment is complete. The buffer solution can also be used to measure the baseline SPR curve of the surface, to wash the surface, or to let the surface and SPR measurement stabilize after an analyte is bound to it. Typically each tip is only used once, or only a few times, and an array 112 of new tips is available, for example to replace the tips each time reading head 102 moves to a new row. Optionally, particularly in a low end system such as system 100, the tips are replaced manually. A controller 114 controls the automated operations of system 100, such as the vacuum system, and the illumination of the samples and the measurement of SPR signals from them. A computer 116 optionally provides a user interface to the controller, for controlling the system and receiving data from it, and/or for analyzing the data.

Figure 1B:
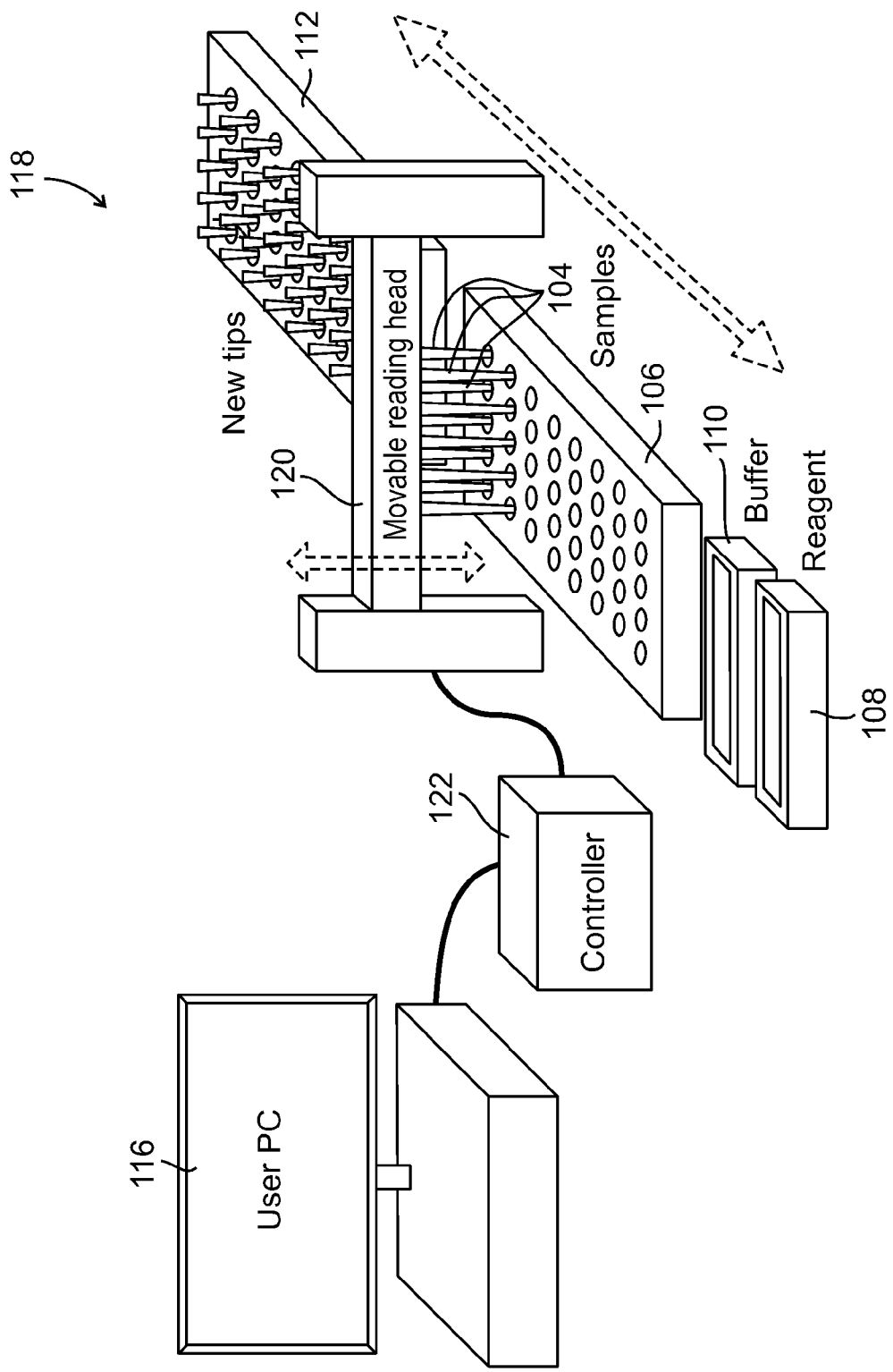
FIGS. 1B and 1C are schematic perspective views of SPR systems for analyzing an array of fluid samples in a well plate, with an array of SPR tips for analyzing a plurality of rows of the fluid samples at a time, according to exemplary embodiments of the invention.

FIG. 1B shows an SPR system 118, similar to system 100, but with more automated functions and potentially greater throughput. A motorized reading head 120 is used, in place of reading head 102 in system 100, which is capable of moving tips 194 along well plate 106, to analyze samples in successive rows, under the controller of a controller 122. Alternatively or additionally, the well plate is motorized, and its position relative to the reading head is controlled by controller 122. Optionally, reading head 120 has more than one row of tips, for example two rows of tips, and can analyze samples from a corresponding number of rows of well plate 106, simultaneously. Optionally, motorized reading head also raises and lowers the tips automatically, under the control of controller 122, and moves automatically to reagent tray 108 and buffer tray 110, to draw reagent, for example fluid containing a ligand, and buffer, into the tips, when needed, for example before measuring one or more new rows of samples with a new set of tips. Optionally, motorized reading head 120 also moves automatically to tray 112 to pick up new tips, and optionally the operation of picking up new tips is also done automatically by reading head 120. In some embodiments of the invention, motorized reading head also automatically releases used tips into tray 112 for disposal, and/or automatically releases new tips into tray 112 for later use, after they have been prepared using reagent 108 and buffer 110.

Figure 1C:
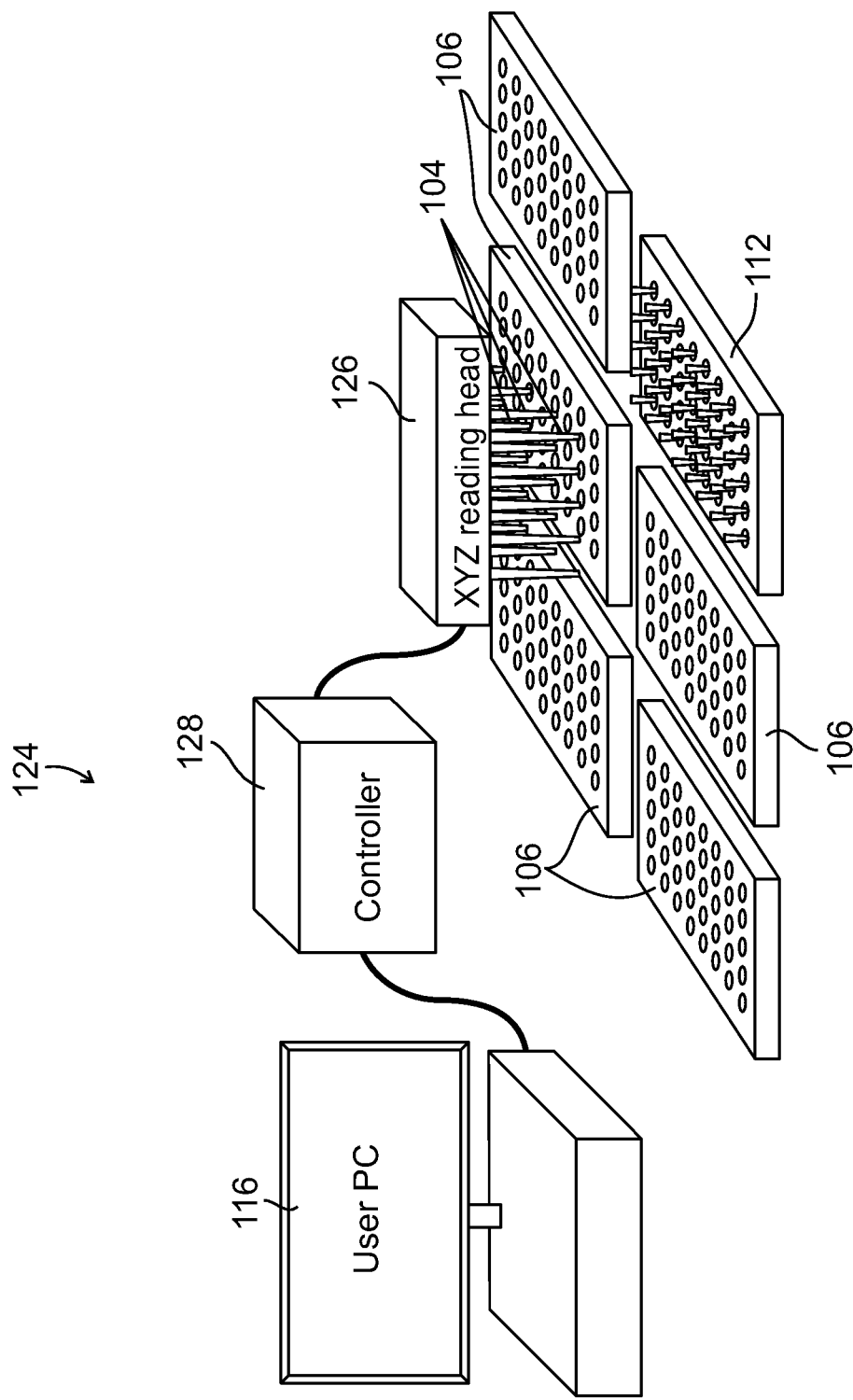

FIG. 1C shows a high end SPR system 124, with more automated functions and potentially greater throughput than system 100 or system 118. In place of reading head 102 and motorized reading head 120, system 124 has an XYZ moving head 126, which is capable of automatically moving in the x-direction along a well plate 106 from one row to the next, as well as from one well plate to another well plate, in either the x or y direction, under the control of a controller 128. In addition, like motorized moving head 120, XYZ moving head 126 can lower tips 104 into wells and raise them out of wells, and pick up new tips from plate 112 and dispose of used tips, under the control of controller 128. In addition, XYZ reading head 126 holds several rows of tips, for example 6 rows of 8 tips each, which allows system 124 to analyze half of the samples in a well plate with an 8 by 12 array of wells, simultaneously and automatically. In the embodiment shown in FIG. 1C, there are six plates, five of them holding fluid samples to be analyzed, and one of them holding new tips to be picked up, and available of disposing of used tips. A user, through personal computer 116, can program controller 128 to analyze any set of the samples in the well plates, up to 96 samples in each of five well plates, in the system shown, without need for any intervention in the middle. In other embodiments of the invention, the numbers are even greater. If, as is typically done, a fresh tip is used for each sample, and if all of the well plates have samples to be analyzed in every well, and the plates are all the same size, then the number of plates holding new tips is optionally equal to the number of well plates holding samples.

Figure 1D:
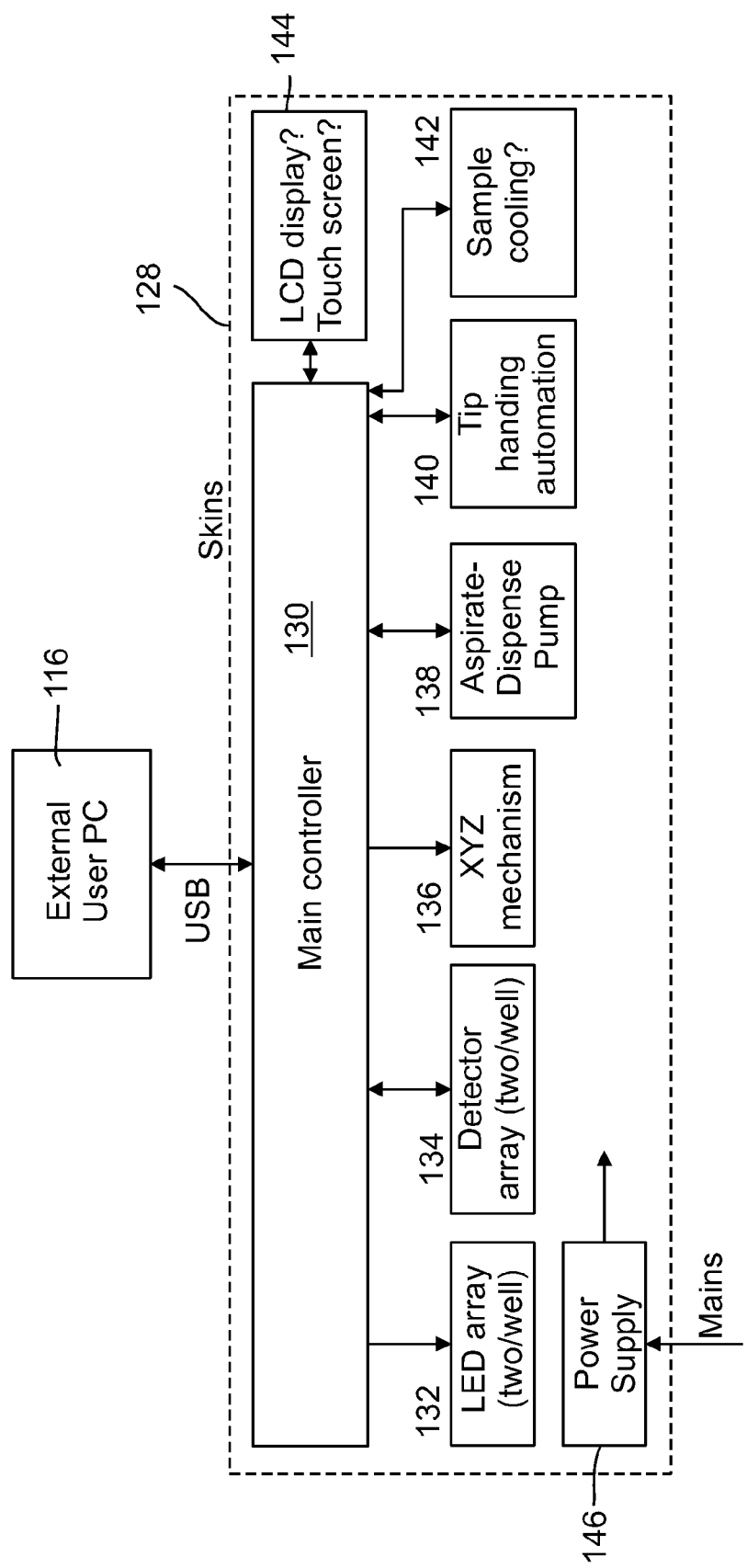
FIG. 1D is a block diagram of a controller for automated analysis of one or more arrays of fluid samples in well plates, used in the system shown in FIG. 1C.

FIG. 1D shows a block diagram for controller 128 in FIG. 1C, according to an exemplary embodiment of the invention. Controllers 114 and 122 optionally have a similar architecture, but with fewer functions. Controller 128 has a main controller 130, which includes the CPU and memory, and modules which provide input and output to the motors of reading head 126, the vacuum system, and the light sources and detectors that are used for the SPR measurements. These modules optionally include, for example, an LED array module 132, which turns on and off each of the LEDs or other light sources used for the SPR measurements; a detector module 134, which receives SPR data from detectors, for example CCD arrays; an XYZ mechanism module 136, which controls the motors in the reading head that raise and lower the tips, and move them from one row to another and/or from one plate to another; a pump module 138, that controls the vacuum pump in reading head 126, drawing in and releasing fluid samples from the well plate, as well as drawing in and releasing reagent containing ligands, and/or buffer fluid; and a tip handling module 140 that controls the picking up and releasing of tips. Optionally, there may also be a sample cooling module 142 that controls a temperature of the fluid samples, and/or a user interface module 144 that controls a display screen, for example, and/or a touch screen, for example a standard display screen and/or touch screen connected to the personal computer. Additional modules for other functions are optionally included as well, and one or more the modules described may be absent, for example the LEDs or other light sources for the SPR measurement could be on all the time, whenever system 124 has power, instead of being controlled by controller 128. Controller 128 also optionally includes a power supply 146, runs software for user interface skins, and has an I/O port for communication with personal computer 116, for example a USB port.

It should be understood that the three SPR systems shown in FIGS. 1A-1D are merely illustrative, and other combinations of automated procedures and manual procedures, and different numbers of tips being held by the reading head, are also possible. For example, an even lower end system than system 100 optionally uses only a single hand-held tip, and analyzes only one sample at a time. This flexibility of the design, which allows less expensive systems to be sold to some customers, and more expensive systems, with higher throughput and more automated procedures, to be sold to other customers, is a potential advantage of SPR systems with the kind of modular architecture shown in FIGS. 1A-1D.

Figure 2:
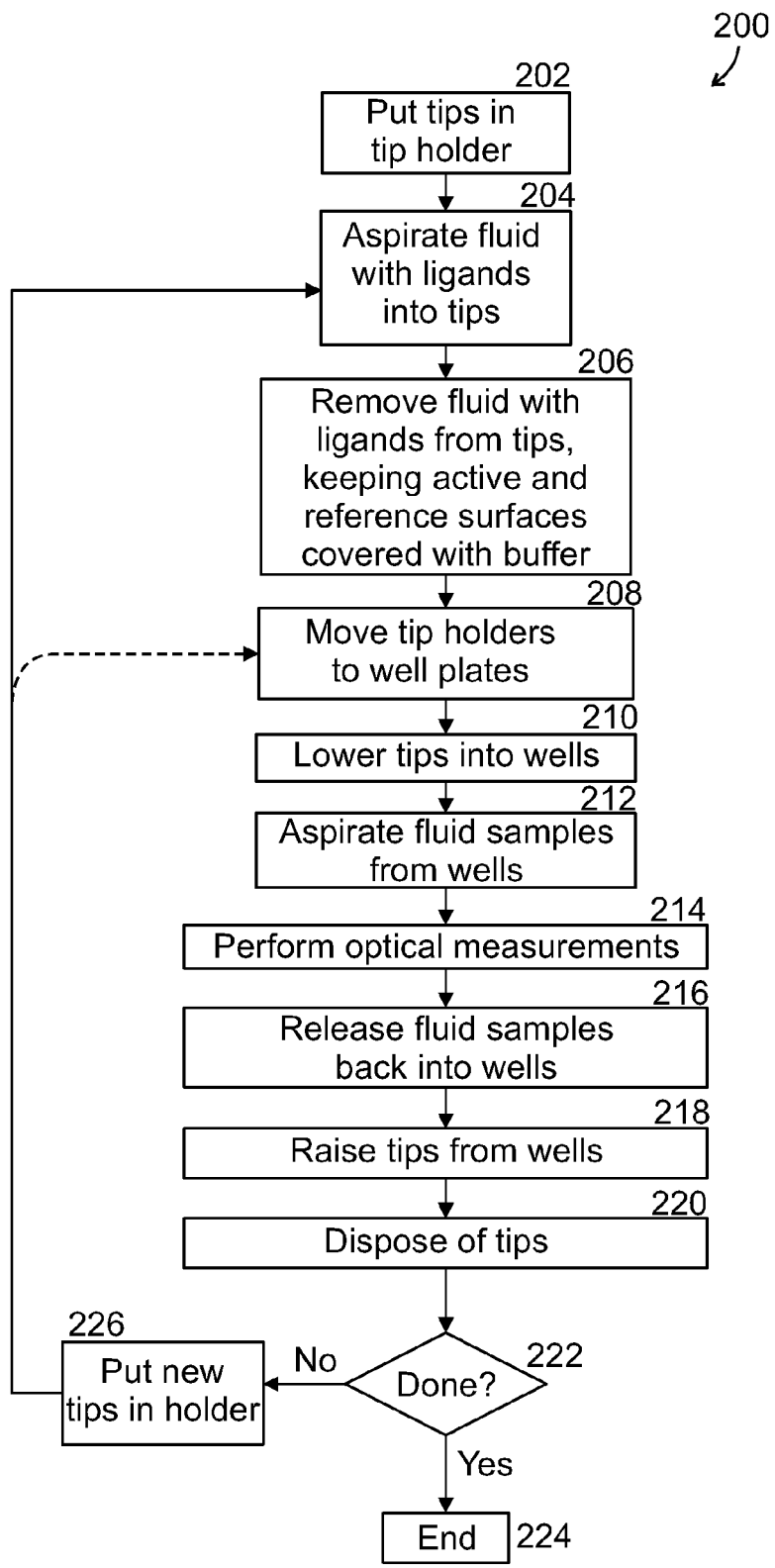
FIG. 2 is a flow chart showing a method of analyzing fluid samples using, for example any of the systems shown in FIGS. 1A-1C, according to an exemplary embodiment of the invention.

FIG. 2 shows a flowchart for a method of operation of any of SPR systems 100, 118, and 124. Each of the elements of the method may be done automatically, under the control of a controller, or manually by a user. At 202, new tips are placed in a tip holder, for example the reading head in FIG. 1A, 1B, or 1C. Optionally, the tips do not already include a ligand bound to an active SPR surface, specific for a particular analyte, but have an active SPR surface that the ligand will bind to if the surface is exposed to it, and a reference SPR surface that the ligand will not bind to, even if the surface is exposed to it, and the active and reference SPR surfaces have similar nonspecific binding properties. Tips with these properties can be made, for example, using any of the methods described below in FIGS. 4A, 4B, and 4C.

At 204, fluid containing the ligand is aspirated into the tips, and binds to the active SPR surface in each tip, but not to the reference SPR surface. At 206, after giving the ligand enough time to bind, the fluid with the ligand is optionally released from the tips, but the active and reference SPR surfaces are optionally kept covered with a buffer solution, so they will not dry out or become exposed to oxygen. Keeping the surfaces wet, and/or keeping them away from air, is often important, particularly for the active surfaces, since the ligand may lose its binding properties if it is allowed to dry out or become exposed to oxygen. Optionally, after releasing the fluid with the ligand, procedures of the chemical treatment, that are done only after binding the ligand, are performed. For example, remaining active functional groups on the SPR surfaces are optionally inactivated, by aspirating into the tip a concentrated solution of a material that covalently bonds to the active functional groups, as described below in FIGS. 12A and 12B, and then releasing the solution.

Actions 204 and 206 are optionally done as a last stage of manufacturing the tips, which are then stored, before being sold to users and used. Alternatively, and more typically, users will want to supply their own ligands for the active surfaces, and actions 202 and 204 are done by the user, either immediately before using the tips to analyze samples, or sometime in advance and are then stored by the user until they are ready to use. If actions 204 and 206 are not done immediately before the tips are used, then the tips are optionally removed from the tip holder, sealed with covers, manually or robotically, to keep them from losing their buffer fluid, and unsealed and placed on a tip holder again only when they are ready to be used for analyzing fluid samples.

At 208, the tip holder that will be used for analyzing the sample, referred to as the reading head in FIGS. 1A, 1B and 1C, is moved to the first well plate which has samples to be analyzed. At 210, the tips are lowered into the wells. At 212, fluid from the wells is aspirated into the tips, where it flows past the SPR surface, for example an active and a reference SPR surface in each tip, and the analyte being tested for, if it is present in the sample, binds to the ligand on the active SPR surface. There may also be some nonspecific binding of the analyte being tested for, and/or other materials in the fluid sample, to both the active and reference SPR surface.

At 214, optical measurements, SPR measurements in the case of an SPR system, are made on the tips, for example using an optical system such as one of those shown in FIGS. 3A-3F, described below. Optionally, optical measurements are made repeatedly, or continuously, while the fluid sample is flowing past the SPR surface or surfaces. This may be done, for example, in order to study the dynamics of the interaction between the analyte and the ligand, and/or in order to obtain a measurement of the concentration of the analyte in the sample, by measuring a rate at which the amount of analyte bound to the SPR surface increases with time. Alternatively or additionally, a single end point measurement is made, after the sample is done flowing past the SPR surface, or after enough of the sample fluid has flowed by so that the surface is saturated.

At 216, when the optical measurement or measurements have been made, the fluid sample is optionally dispensed back into the well. Optionally, optical measurements are made also when the fluid sample is being dispensed back into the well, and is flowing back past the SPR surface or surfaces. This allows further data to be obtained on the rate at which the amount of bound analyte increases with time, if it has not saturated already. Tests done by the inventors, described below in the Examples section, show that the thickness of the bound layer of analyte increases smoothly with time throughout the time that the fluid sample is being aspirated into the tip past the SPR surface and being dispensed back into the well, with no visible jump or change in slope when the direction of flow changes. This result indicates that there is negligible dilution of the fluid sample by the buffer solution that is already in the tip before the fluid sample is aspirated, during the time that the fluid sample is being aspirated and dispensed, a total of 110 seconds. Further aspiration and dispensing of buffer solution, following the dispensing of the fluid sample, causes only very small further changes in the thickness of the bound layer of analyte, showing that very little of the fluid sample remains in the tip mixed with the buffer solution, after the fluid sample is dispensed back into the well.

Optionally, after the sample has returned to the well, it can be used again later for another measurement, looking for the same analyte, for example in order to reduce error rates by obtaining better statistics, or looking for a different analyte. The ability to use the sample over again repeatedly has the potential advantage that much information can be obtained even from a very small sample, when it may be difficult to obtain a larger sample.

At 218, the tips are raised from the wells. Optionally, the tips used in that set of measurements is disposed of at 220, for example by moving to an empty tray and releasing each tip into a well, or simply releasing all of the tips into a common area for disposal. Using each tip only once has the potential advantage that future measurements of other samples will not be contaminated by small amounts of earlier samples remaining in the tip, and disposing of the tip as quickly as possible has the advantage, in the case of a sample potentially containing hazardous material, for example infectious material, that the risk of the hazardous material escaping can be kept very low. And the inexpensive methods that can be used for manufacturing the tips, for example the methods described below in FIGS. 4A-4C, make it practical to use each tip only once. However, in some cases, for example if a series of measurements are being made on the same sample, or on different samples that are expected to be identical, for example in order to reduce errors by improving the statistics, the same tip is optionally used more than once for making a measurement. If a tip is to be used more than once, even for different samples, then analyte adhering to the SPR surface is optionally first removed from the surface, by drawing into the tip a solution containing a reagent, for example an acid, that removes the analyte when it flows past the surface.

At 222, a decision is made whether the measurements are done, or if more measurements are to be made. If the measurements are done, then the procedure ends at 224. If more measurements are to be made, using new tips, then the new tips are put into the tip holder, for example the reading head if measurements are to be made right away, at 226. If the new tips do not already have ligand bound to their active surfaces, then fluid containing the ligand is aspirated into the tips again at 204, and the procedure repeats. If the new tips already have ligand bound to the active surfaces, because they were stored that away after binding ligand in advance, then the procedure moves instead directly to 208, and the tip holder is moved to the next well plate, or the next row or set of rows on the same well plate, to draw a new set of samples. Optionally, the SPR system is used to aspirate ligand into a new set of tips, which are then removed from the system and stored in an orientation so that the ligand will slowly drip down and bind to the surface, freeing up the system for a different task.

Configuration of Exemplary Optical Sub-system

Figure 3A:
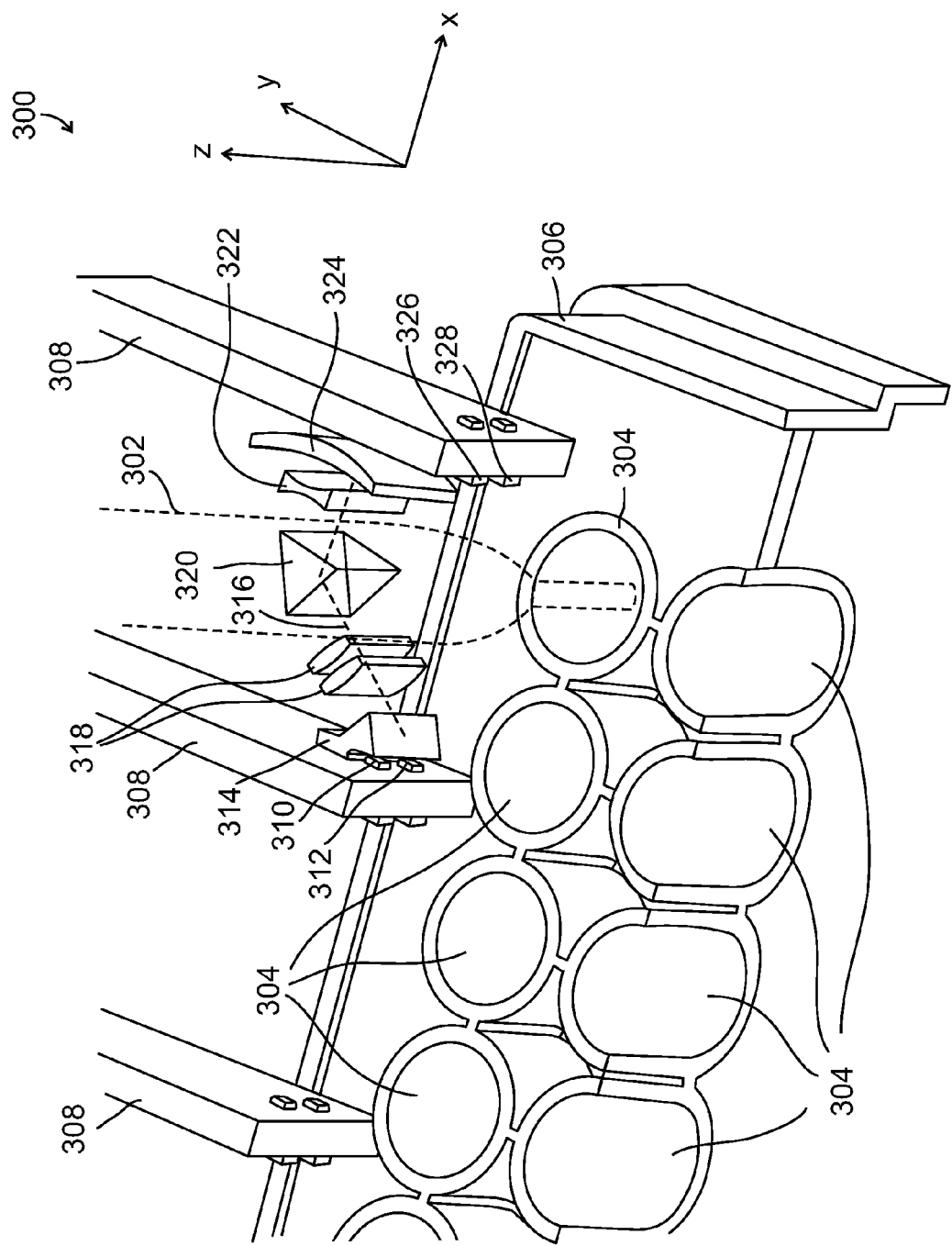
FIG. 3A is a schematic perspective view of an optical sub-system that is optionally used in the SPR system shown in any of FIGS. 1A-1C, according to an exemplary embodiment of the invention.

FIG. 3A shows a perspective view of an optical sub-system 300, used for illuminating the active surface in one tip, and for obtaining data on optical measurements, for example SPR measurements, made of the active surface of the tip. The measurements are made, for example, when an analyte has been bound to the active surface, or is in the process of being bound to the surface, by an analyte-specific ligand. Alternatively, if the analyte is absent from the sample, measurements indicating the failure of any analyte molecules to bind to the ligand can be used to show that it is absent, at least down to a level of sensitivity of the measurements. In the case of SPR measurements, for example, the exact angle at which reflectance from the surface is minimal, due to the excitation of surface plasmons by the incident light, depends on a surface density of the analyte bound to the active surface, so the quantity of bound analyte can be measured by measuring the reflectance from the surface as a function of angle of incidence.

In FIG. 3A, for clarity, only one optical sub-system is shown, for making optical measurements on one tip 302, shown only as an outline with dashed lines. In an actual system, such as the systems shown in FIGS. 1A-1C, there will generally be a row of tips, or an array of more than one row of tips, each tip associated with its own optical sub-system, an arrangement that allows optical measurements to be made simultaneously in the entire row or array of tips. Optionally, the optical sub-systems are attached to the reading head. Alternatively, the optical sub-systems are attached to the well plates, but attaching them to the reading head has the potential advantage that a given system needs fewer optical sub-systems, which saves money, and that the reading head can more easily keep the tips positioned precisely relative to the optical sub-system, which in some systems is required for the optical sub-system to work properly.

Figure 3B:
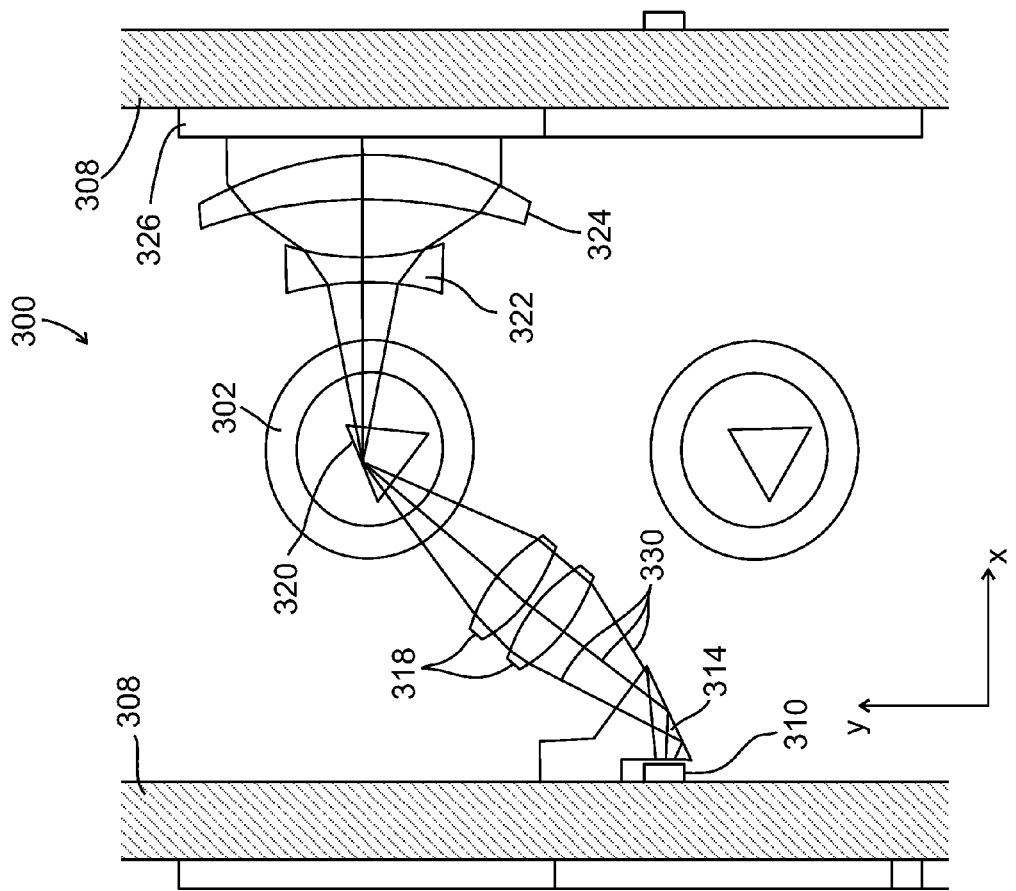
FIG. 3B is a view of the same optical sub-system in the x-y plane.
Figure 3B:
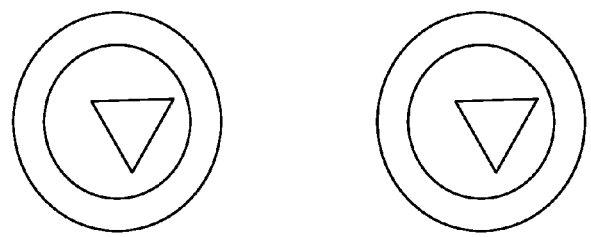
Figure 3C:
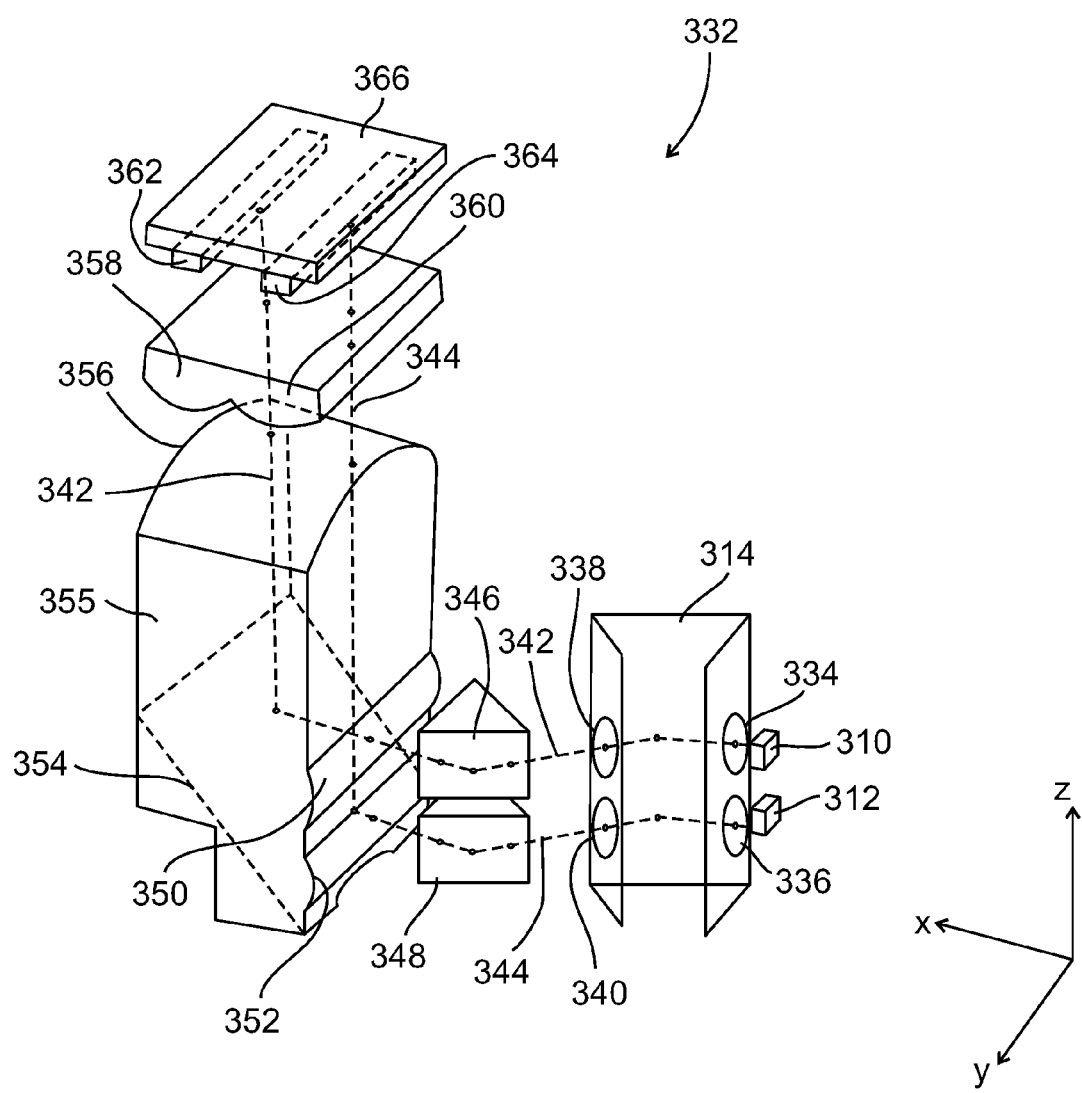
FIG. 3C is a schematic perspective view of an alternative optical sub-system that is optionally used in the SPR system shown in any of FIGS. 1A-1C, according to an exemplary embodiment of the invention.

Although the optical sub-systems need not be of the modular form shown in FIGS. 3A and 3C, identical for each tip, such a modular optical sub-system has the potential advantages that it may be easier to design and to manufacture, and measurement results will not depend on which optical sub-system in the array is used. One goal of such a design, which may be challenging to meet, is to fit the entire optical path, from light source to detector, into the space available between adjacent tips in the reading head. The particular designs shown in FIGS. 3A and 3C represent two different exemplary solutions to that design problem, but other optical sub-system configurations may be used instead. For example, an optical sub-system may be used which combines features of the system shown in FIG. 3A with features of the system shown in FIG. 3C.

In FIG. 3A, tip 302 is shown inserted into one of the wells 304 in a well plate 306. Well plate 306 is shown in a cutaway view, so that the bottoms of some of the wells 304 can be seen. The optical sub-systems are supported by a set of bars 308, running parallel to the rows of wells and the rows of tips, i.e. in the y-direction in FIG. 3A one more bar than there are rows of tips held by the reading head. The bars are approximately at the level of the SPR surfaces in the tip, at least when the SPR measurements are being made. Because each optical sub-system may extend further in the x-direction than in the y-direction, if the optical systems are packed as closely together as possible, then optionally, if there is more than one row of tips, the spacing between rows of tips may be greater than the spacing between adjacent tips on a given row, for example twice as great. Optionally, the spacing of the wells in well plate 306 matches the spacing of the tips. Alternatively, the wells are arranged with a different spacing than the tips, and only some of the wells have tips associated with them at a given time. For example, as in the case shown in FIG. 3A, there is a row of tips only associated with every other row of wells, and the wells are arranged in a square array. In this case, fluid samples in half of the wells, under the footprint of the reading head, can be analyzed at a given time, and the fluid samples in the other wells can then be analyzed by raising the tips out of the wells, exchanging them for new tips if desired, or optionally stripping off the analyte from the SPR surfaces in the tips and re-using the tips, and moving the reading head to a position displaced in the x-direction by one row of wells, or by an odd number of rows of wells, from its original position, and lowering the tips into the other rows of wells.

The SPR surfaces are illuminated by light sources, for example LEDs, and if there are two SPR surfaces in each tip, an active surface and a reference surface, then optionally there are two LEDs, 310 and 312, associated with each tip, mounted on bars 308. The two LEDs are optionally displaced from each other in the z-direction, for example by the same distance as the active and reference SPR surfaces in each tip, which are displaced from each other in the z-direction, in the embodiment of the invention shown in FIG. 3A. Alternatively there is only a single LED, whose light is directed by the optical sub-system to both SPR surfaces. Light from the two LEDs is optionally reflected from a mirror 314 which aims the light toward the SPR surfaces in the tip. The axis of the light beams is indicated in FIG. 3A by a dotted line 316. For clarity, instead of showing two parallel light beams, one for each SPR surface, only a single light beam axis is shown, halfway in between the two light beam axes. The light beams pass through a convex lens 318, optionally cylindrical in the z-direction and convex only in the x-y plane, optionally two cylindrical convex lenses as shown in FIG. 3A, and reflect from the SPR surfaces on the back of a prism 320. Optionally, the two surfaces are located on separate prisms, as will be shown in FIGS. 7 and 9 below. But in FIG. 3A, for clarity, only a single prism is shown, and optionally that is true of the tip, for example in the embodiment shown in FIG. 10, below. Similarly, lenses 318, and other lenses of optical sub-system 300, particularly if they are cylindrical in the z-direction, optionally extend far enough in the z-direction for both beams of light to pass through them, or alternatively separate lenses are used for each beam of light.

It should be understood that lenses 318, and other optical elements shown in FIG. 3A as if they were floating in air, are mechanically connected to bars 308, and held rigidly in place, but for clarity these connections are not shown in FIG. 3A. Prism 320, of course, is part of tip 302, and optionally is connected to bars 308 only indirectly through the reading head.

After reflecting from the SPR surfaces on prism 320, the beams go through a concave lens 322, optionally cylindrical in the z-direction, then through another convex lens 324, optionally cylindrical in the z-direction. Alternatively, any of the lenses are spherical, which has the potential advantage that the optical system may be easier to assemble because spherical lenses may be easier to align. After passing through the lenses, the beams reach two linear array detectors 326 and 328, running along the length of bar 308 in the y-direction, one linear array for the light beam reflecting from the active SPR surface, and one linear array for the light beam reflecting from the reference SPR surface.

In a case where there are three or more SPR surfaces in each tip, for example one reference surface and two or more active surfaces, with different surface densities of ligand, or with different ligands, then optical sub-system 300 is modified to make SPR measurements on all of the SPR surfaces in the tip. There is, for example, a separate prism for each SPR surface, or one prism long enough to accommodate all of the SPR surfaces, and optionally there is a separate light source for each SPR surface, and a separate linear array detector for each SPR surface. There are cylindrical lenses long enough to focus the light on each SPR surface and to bring the reflected light from each SPR surface to the detector for that SPR surface, similar to what is shown in FIG. 3A for the case of two SPR surfaces, or there is a separate set of lenses to accomplish this task for each SPR surface.

The effect of the lenses and reflecting surfaces on the light beams is shown in FIG. 3B, which is cross-sectional view of optical sub-system 300, in the x-y plane. FIG. 3B shows not only a light ray going along the axis of each beam, but also a light beam going along the edge of the beam on each side of the axis in the x-y plane, a total of three light rays 330. Because FIG. 3B shows only a cross-section of the optical sub-system in the x-y plane, only the light beam from one of the LEDs, LED 310, is shown, the light beam from LED 312 behaves in the same way, in another x-y plane parallel to the plane shown in FIG. 3B. FIG. 3B also shows other tips in the array of tips, and the other LEDs and linear array detectors, but for clarity does not show the lenses and light rays of the other optical sub-systems associated with those tips.

The light rays emitted by LED 310 are initially diverging, and continue to diverge after reflecting from mirror 314, which is optionally a planar mirror, or a total internal reflector. Lens 318 make light rays 330 converge on SPR surface 320, for example focusing an image of LED 310, at least in the x-y plane, on SPR surface 320, inside tip 302. SPR surface 320 is one face of a prism, which is optionally configured so that axis of the light beam enters and leaves the prism nearly perpendicular to the faces that it passes through, to minimize displacement and/or chromatic aberration of the light beam. There are light rays converging on SPR surface 320 from a range of angles of incidence. The rays are reflected at their angle of incidence, and diverge after reflecting from SPR surface 320. Optical system 300 is configured so that the range of angles includes the range of angles of incidence of interest for SPR measurements, and optionally this range of interest makes up a substantial part of the range of angles of incidence of the light rays reaching SPR surface 320 from LED 310, so that the light is used efficiently. For example, the range of angles optionally extends over a range of 2 degrees, 3 degrees, 5 degrees, 7 degrees, 10 degrees, 15 degrees, or smaller, larger or intermediate angles, and is centered at 2 degrees, 3 degrees, 5 degrees, 7 degrees, 10 degrees, 15 degrees, or a smaller, larger, or intermediate angle.

The light leaving SPR surface 320 diverges more rapidly after passing through concave lens 322, and then optionally becomes nearly parallel after passing through convex lens 324. Finally, the light beam reaches linear array detector 326. The purpose of concave lens 322 is to spread out the light beam, which is initially rather narrow, to a large fraction of the full width of linear array detector 326, in the relatively short distance available between tip 302 and linear array detector 326. The length of linear array detector 326 can be as great as the distance between adjacent tips, or adjacent wells, in the y-direction. The light rays at different lateral positions in the light beam, in the x-y plane, have reflected from SPR surface 320 at different angles, so measuring the intensity of light as a function of position along linear array detector 326 provides a measure of the reflection coefficient of the SPR surface as a function of angle of incidence. Having a relatively long linear array detector makes it possible to measure the reflection coefficient as a function of angle of incidence, in the relatively small range of interest for SPR, more accurately. Convex lens 324 optionally makes the light rays all hit linear array detector perpendicularly, so that the signals from the different elements of the linear array detector differ only from differences in angle of incidence at the SPR surface, not from differences in angle of incidence at the linear array detector, or from differences in distance to the linear array detector, and further allows the optical sub-system to be designed so that all parts of the linear array detector have an optimized sensitivity, for example providing an optimized trade-off between angular resolution and signal to noise level. However, if the light rays leave concave lens 322 diverging at a large angle, as shown schematically in FIG. 3B, then there may be a significant difference in distance to the linear array detector, for rays on the edge of the light beam and rays in the center.

Optionally, the measured SPR signal is normalized to the signal at the detector when the SPR tip is replaced by an unused SPR tip with no liquid in it, and a dry SPR surface. Such a dry measurement typically does not include any SPR effects, since the dip in reflectance due to SPR is generally shifted to an angle far from the dip when the SPR surface is surrounded by liquid, and is outside the range seen by the detector. But the dry measurement will include the dependence of reflectance on angle of incidence, due to other effects, for example the optics configuration. The normalized signal may then exhibit only the SPR effects, and may be easier to compare to theoretical SPR curves.

Because the lenses shown in FIG. 3A are cylindrical in the z-direction, the light beams from LEDs 310 and 312 will, in general, diverge in the z-direction, at whatever rate they are diverging initially when they emerge from the LEDs. It is potentially advantageous if the light beams diverge at a low enough rate in the z-direction so that they do not extend too much more than the width of the linear array detectors in the z-direction, when they reach the linear array detectors, so that light from the LEDs is not wasted. It is particularly advantageous if the rate of divergence in the z-direction is small enough so that light from each of the two SPR surfaces, the active and reference surface, only reaches its own linear array detector, and does not reach the other linear array detector, which might make it difficult to cleanly separate the signals from the two SPR surfaces. It is also potentially advantageous if the light rays reaching the SPR surface at a given angle in the x-y plane and at different values of z all are nearly parallel to each other, so that all the light rays reaching the linear array detector at a given value of y have the same angle of incidence on the SPR surface. If the light beams initially diverge too fast to satisfy one or both of these conditions, when they are emitted by LEDs 310 and 320, then optionally lenses 318 are also convex in the z-direction, so that the beam becomes more nearly parallel. Alternatively, another lens, not shown in FIG. 3A, makes the light beams more nearly parallel, before they diverge too much.

Optical sub-system 300, shown in FIGS. 3A and 3B, has the properties that the light ray on the axis of each of the light beams travels substantially perpendicularly to the direction of the flow of the fluid sample in the tip, between the light source and the SPR surface, as well as between the SPR surface and the detector array. One or both of these properties optionally apply to an optical sub-system used in such an optical detection system, even if it does not have exactly the same configuration as optical sub-system 300, and these properties are potentially advantageous because they may make the distance between the light source and the SPR surface relatively short, and they may make the distance between the SPR surface and the detector array relatively short, providing a relatively high signal to noise ratio for a given type of light source and detector array. Optical sub-system 300 also has the properties that the light paths for the active SPR surface and the reference SPR surface are substantially similar to each other, being oriented in substantially parallel directions at corresponding parts of the light path, but are displaced from each other along the direction of flow of the fluid sample, both the portions of the optical path between the light source and the SPR surface, and the portions of the optical path between the SPR surface and the detector array. These properties, which also optionally apply to another optical sub-system used in such an optical detection system, have the potential advantage that the optical sub-system may be more compact, fitting into the limited space between adjacent rows of tips, and may be easier to design and build, since corresponding optical elements for active and reference SPR surfaces may be substantially identical.

Optionally, any of the lenses in optical sub-system 300 has a polarizing filter, so that the light reaching the linear array detector all has the P-polarization for which SPR effects occur. Alternatively, there is a separate polarizing filter, not shown in FIGS. 3A and 3B, somewhere in the optical path between the LEDs and the linear array detector, including on the LED or on the linear array detector. Light of the other polarization, the S-polarization, does not exhibit SPR effects, so would only contribute noise to the measurement, and not signal, and filtering it out has the potential advantage of increasing the signal to noise ratio. In some embodiments of the invention, the SPR surface is covered with a thin layer of a material, such as a 500 nm thick layer of $SiO_2$, which results in an SPR effect occurring with light of the S-polarization, rather than the P-polarization. In these embodiments, it is the $SiO_2$ surface, rather than the underlying layer of metal, that is chemically treated to bind to the ligand, or not to bind to the ligand in the case of the reference surface. In these embodiments of the invention, the polarizing filter optionally polarizes light so that the light reaching the linear array detector has the S-polarization. Optionally, both methods are used, for example on different SPR surfaces.

FIGS. 3C-3F show an optical sub-system 332 according to another exemplary embodiment of the invention. Sub-system 332 does not have a concave lens 322, which, in optical sub-system 300, spreads the light beam out in the y-direction, in the short distance from the tip to the linear array detector. Instead, optical sub-system 332 has a reflecting element that directs the beams emerging from the tip upward in the z-direction, giving them more room to spread out in the y-direction, even without passing through a concave lens. The linear array detectors are situated some distance above the SPR surfaces, in the z-direction. Optical sub-system 332 has the potential advantage that the light rays do not diverge at large angles, so that all light rays travel nearly the same distance from the LED to the linear array detector. But optical sub-system 300 has the potential advantage that the optical elements may be simpler in shape, for example all cylindrical, smaller, and cheaper to manufacture. On the other hand, the fact that the light rays in sub-system 300 diverge at large angles may make sub-system 300 more sensitive to errors in the shape of the lenses, and if so the optical elements in sub-system 332 may be less expensive to manufacture to the required tolerance.

It should be understood that the elements of optical sub-system 332 are mechanically coupled to the reading head, optionally through bars similar to bars 308 in FIGS. 3A and 3B, even though, for clarity, they are shown in FIGS. 3C-3F as floating in air.

As shown in FIG. 3C, light beams from LED 310 and LED 312 pass through convex lenses 334 and 336 respectively, reflect from mirror 314 which directs them toward the SPR surfaces, and then pass through a second set of convex lenses, 338 for LED 310, and 340 for LED 312. Optionally, lenses 334, 336, 338 and 340, and mirror 314, are formed from curved and flat surfaces of a single transparent solid element. The axes of the two light beams, 342 and 344, are shown as dotted lines in FIG. 3C. The convex lenses concentrate light beams 342 and 344 respectively on SPR surfaces 346 and 348, one of them, for example, an active SPR surface, and the other one, for example, a reference SPR surface. In other embodiments of the invention, there is only one convex lens for each beam, either before or after mirror 314, or a single convex lens that concentrates both beams, or the mirror is curved and concentrates the beams. Optionally, the convex lenses focus images of the two LEDs respectively on the two SPR surfaces. Whether or not the SPR surface is exactly at a focal plane of the convex lenses, there is a range of angles of incidence made by the different light rays in each of the light beams, on the SPR surfaces. Optionally, that range of angles includes a range of interest of angles of incidence for SPR, but is not much greater than that range of interest, which has the potential advantage that the light is used efficiently to obtain the SPR curves. Optionally, SPR surfaces 346 and 348 are located on faces of prisms, which other faces of the prisms arranged so that the axes of the incident beams and reflected beams are approximately normal to the faces, potentially reducing chromatic aberration and other distortion or displacement of the beams.

After beams 342 and 344 reflect from the SPR surfaces, they pass respectively through cylindrical convex lenses 350 and 352, which reduce their divergence in the z-direction, and reflect from a reflecting surface 354, oriented at a 45 degree angle, so that they are directed upward in the z-direction. Optionally, lenses 350 and 352, and reflecting surface 354, are part of a single solid transparent reflecting element 355, and are formed from curved and flat surfaces of element 355. Alternatively, lenses 350 and 352, and reflecting surface 354, are separate elements, coupled mechanically. Light beams 342 and 344 travel upward to the top of element 355, which is optionally located far enough away so that the light beams have spread out in the y-direction over a relatively large fraction of the distance between adjacent tips in the y-direction. However, due to passing through lenses 350 and 352, the light beams do not diverge very much in the x-direction, and may even converge somewhat in the x-direction, when passing upward through element 355. When the light beams reach the top of element 355, they optionally pass through a convex cylindrical lens 356, optionally formed from a curved upper surface of element 355 if it is a single solid transparent element. Cylindrical lens 356 optionally makes each of the light beams nearly parallel, rather than diverging, in the y-direction. Optionally, light beams 342 and 344 then pass, respectively, through cylindrical convex lenses 358 and 360. The two light beams then reach linear array detectors 362 and 364 respectively, mounted on a holder 366. Lens 356 is optionally configured so that the different rays of each light beam are nearly parallel to each other, and perpendicular to the surface of the linear array detector, when they reach it, while lenses 358 and 360 optionally concentrate the light beams in the x-direction so that most or all of the power in each light beam reaches its own linear array detector, but very little of the power in each light beam reaches the other linear array detector, which has the potential advantage of increasing light intensity on the linear array detectors, while decreasing interference between the SPR measurements for the active and reference surfaces. The linear array detectors each optionally extend almost as far as they can in the y-direction, i.e. nearly the distance from one tip to an adjacent tip in the y-direction. Different array elements of the linear array detectors detect light rays that reflected from the SPR surface at different angles of incidence. By spreading light rays from the entire range of interest of angles of incidence for SPR, over close to the maximum distance in the y-direction, it is potentially possible to increase the angular resolution and/or signal to noise ratio of the SPR measurements.

Figure 3D:
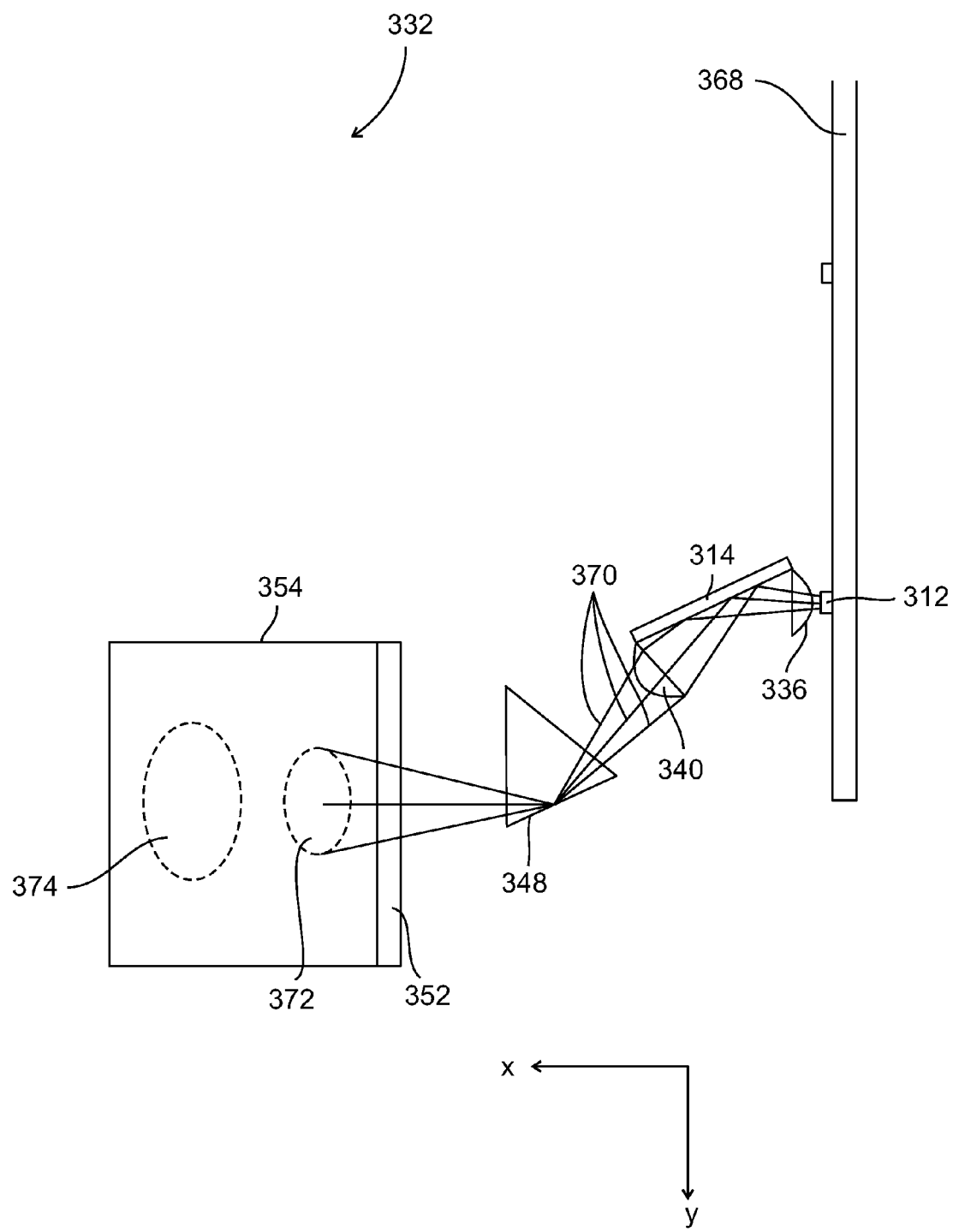
FIGS. 3D, 3E, and 3F are views of the same system in the x-y, x-z, and y-z planes, respectively.
Figure 3E:
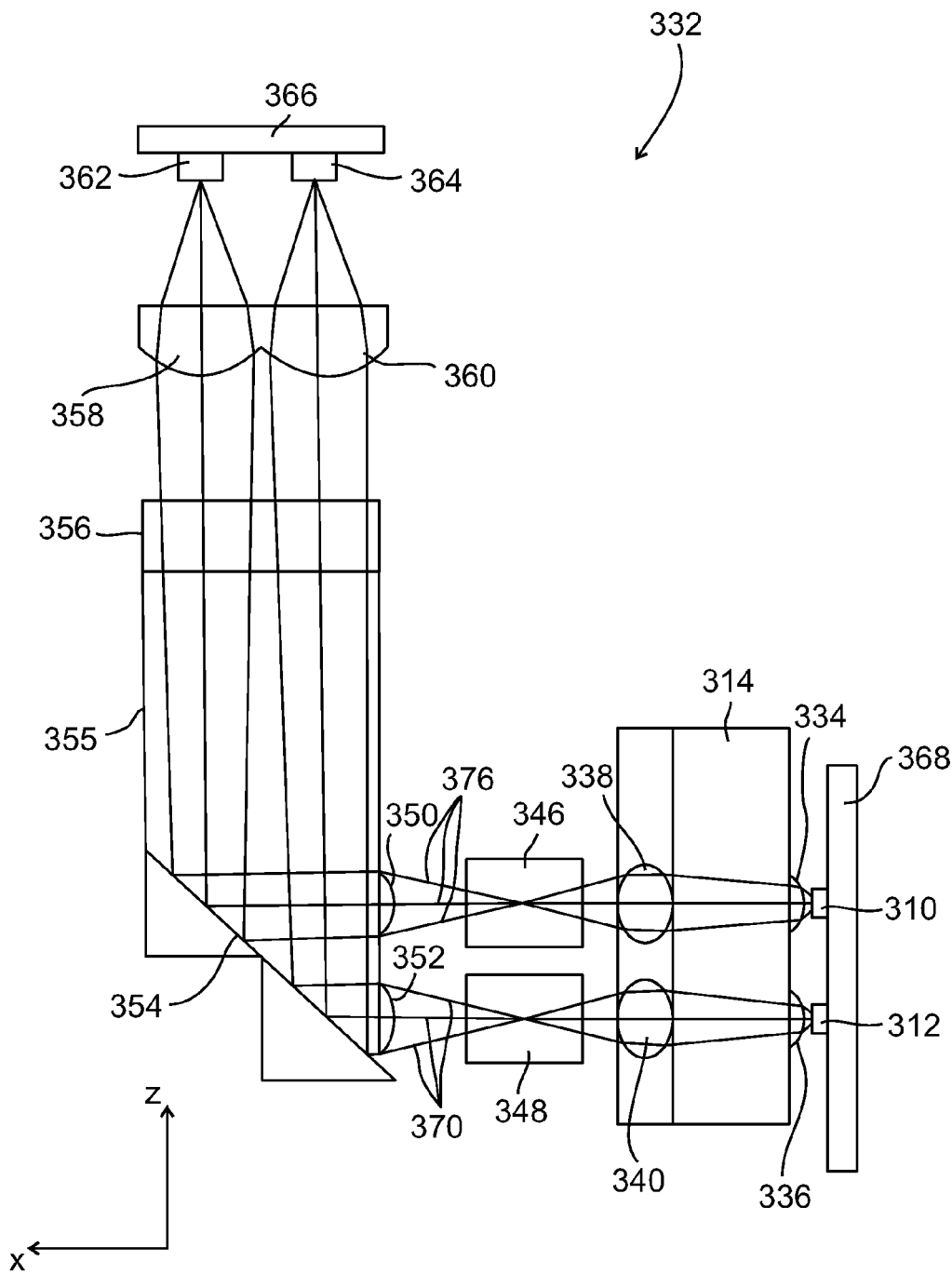
Figure 3F:
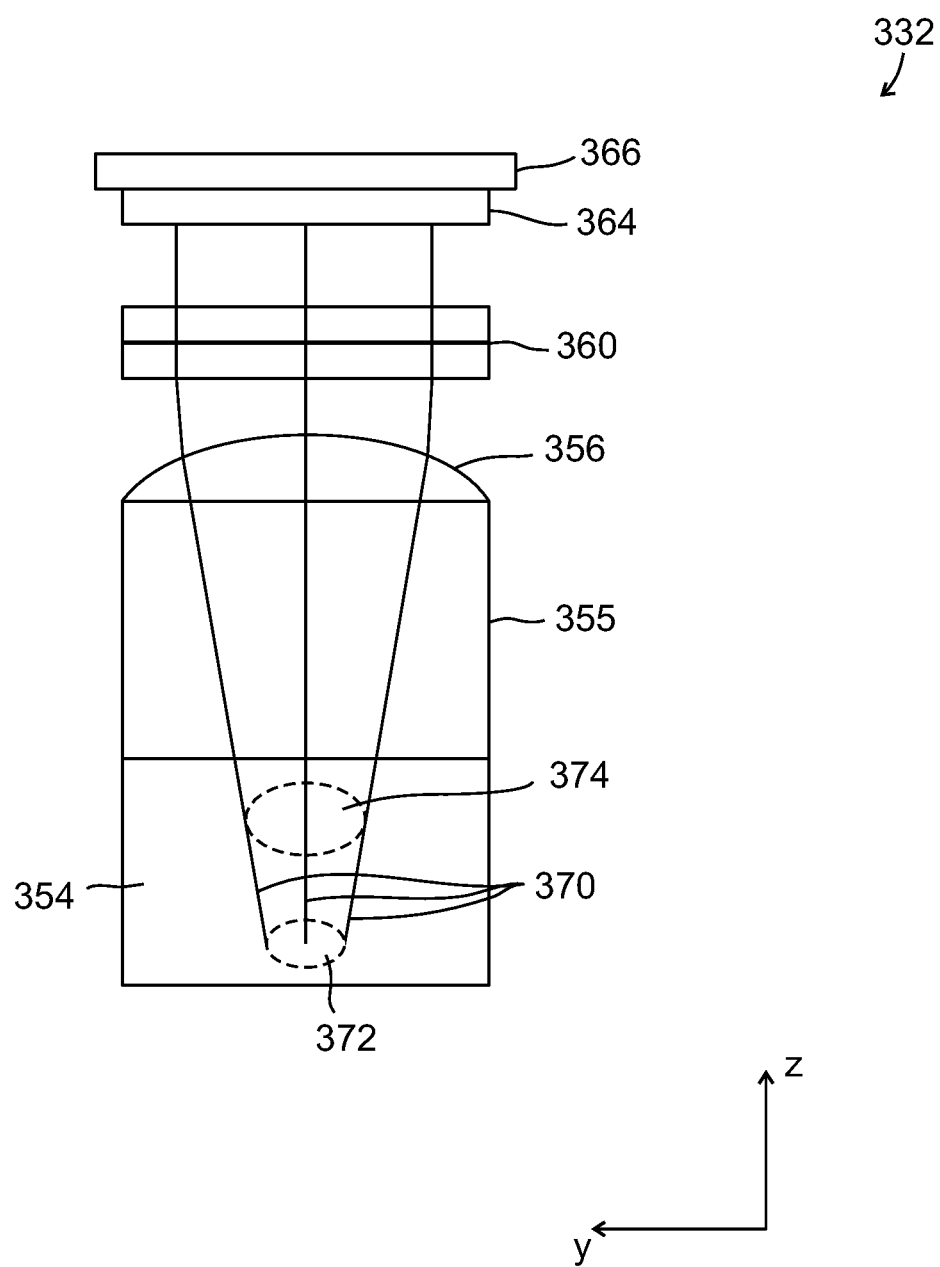

FIGS. 3D, 3E, and 3F show views of optical sub-system 332 respectively in the x-y plane, the x-z plane, and the y-z plane. FIG. 3D shows the x-y plane that contains LED 312, and also shows a bar 368, similar to bar 308 in FIGS. 3A and 3B, that LEDs 312 and 310 are optionally mounted on. Light rays 370 from LED 312 are focused by convex lenses 336 and 340, and reflected by mirror 314, so that they converge on SPR surface 348, where they reflect at different angles of incidence, providing SPR data. Light rays 370 then diverge, pass through cylindrical lens 352 which has no effect on than appearance of the beam in the plane of the drawing, and reach reflecting element 354, which appears foreshortened in the x-direction because it is oriented at a 45 degree angle to the plane of the drawing. Light rays 370 form, for example, a circular spot on the surface of reflecting element 354, which appears foreshortened in the x-direction in FIG. 3D. LED 310 and its light rays and the optical elements they interact with are not shown in FIG. 3D because they are in a different plane, parallel to the plane of the drawing, directly over LED 312 and light rays 370. However, the light rays from LED 310 extend further in the x-direction than light rays 370 before they reach reflecting element 354, so a foreshortened circular spot 374, of the light rays from LED 310 on reflecting element 354, is shown in FIG. 3D.

FIG. 3E shows optical sub-system 332 in the x-z plane, as seen from the y-direction. LED 310, its light rays 376, including light rays on the edge of the beam and a light ray on the axis of the beam, and the optical elements they interact with, are shown in FIG. 3E, as well as LED 312, its light rays 370, and the optical elements they interact with. After reflecting from reflecting surface 354, light rays 370 and light rays 376 pass upward through element 355, more or less parallel although they may be diverging or converging slightly, and in FIG. 3E they are shown diverging slightly. They pass through cylindrical convex lens 356 at the top of element 355, which does not affect their appearance in the plane of the drawing. Light rays 370 then pass through cylindrical convex lens 360 which concentrates them on linear array detector 364, and light rays 376 pass through cylindrical convex lens 358, which concentrates them on linear array detector 362. In other embodiments of the invention, separate lenses for the two light beams may be replaced by a single larger lens for both light beams, a single lens such as lens 356 may be replaced by separate lenses for the two light beams, two cylindrical lenses with curvature in different planes may be replaced by a single lens, generally astigmatic, with curvature in both planes, and pairs of focusing lenses, for example lenses 352 and 360, or lenses 336 and 340, may be replaced by a single focusing lens which focuses the light at the same distance. But preferably the optical sub-system is designed so that none of the power from one beam reaches the linear array detector for the other beam, which could result in cross-talk between the signals from the two SPR surfaces. The design shown in FIG. 3C has the potential advantage over these other embodiments, that the operation of the optical sub-system may be less adversely affected by errors in the shape of the lenses.

FIG. 3F shows a view in the y-z plane of light rays 370, in element 355. Light rays 370, travelling in the x-direction after reflecting from the SPR surface, illuminate reflecting surface 354 in a circular spot 372, for example. Because reflecting surface 354 is oriented at a 45 degree angle to the plane of the drawing, reflecting surface 354 and circular spot 372 appear foreshortened in the z-direction, is FIG. 3F. After reflecting from surface 354, light rays 370 travel upward in the z-direction, while spreading out in the y-direction. At the top of element 355, when they have spread out to a large fraction of the distance between adjacent tips in the y-direction, light rays 370 pass through cylindrical convex lens 356, after which they are parallel rather than diverging. They pass through cylindrical convex lens 360, which does not change their appearance in the plane of the drawing, and reach linear array detector 364, all striking linear array detector nearly perpendicular to the surface. The light rays striking different detector elements of linear array detector 364, at different positions in the y-direction, have reflected from SPR surface 348 at different angles of incidence. By measuring the light intensity striking each of the detector elements of linear array detector 364, the reflectance as a function of angle of incidence, from the SPR surface, can be determined. Having light rays 370 all strike linear array detector 364 nearly perpendicular to the surface has the potential advantage that the response of the linear array detector varies from one detector element to another mostly because of differences in the reflectance of the SPR surface at different angles of incidence, and not because the light rays are striking different detector elements of linear array detector 364 and different angles of incidence. Furthermore, the light intensity on the surface of the linear array detector will be greatest, for a given light beam, if the light rays strike the linear array detector at a perpendicular angle, which will make the signal to noise ratio greater.

Light rays 376, from the other SPR surface, also reflect from reflecting surface 354. They do not reflect from reflecting element 354 at the same location as light rays 370, but illuminate reflecting element 354 over circular spot 374, for example, which appears foreshortened in FIG. 3F because reflecting element 354 is oriented at a 45 angle to the plane of the drawing. Above spot 374, light rays 376 would overlap light rays 370 in FIG. 3F, as they travel upward through element 355, so they are not shown in FIG. 3F.

Optical system 332, as shown in FIGS. 3C-3F, may be modified to accommodate measurements from three or more SPR surfaces in a tip, similar to what was described above for optical sub-system 300 in FIGS. 3A-3B. Optionally, if there are more than two SPR surfaces in a tip, then there is a separate light source, set of lenses and other optical elements, prism, and linear array detector, for each SPR surface.

Exemplary Tip Design and Method of Manufacture

Figure 4A:
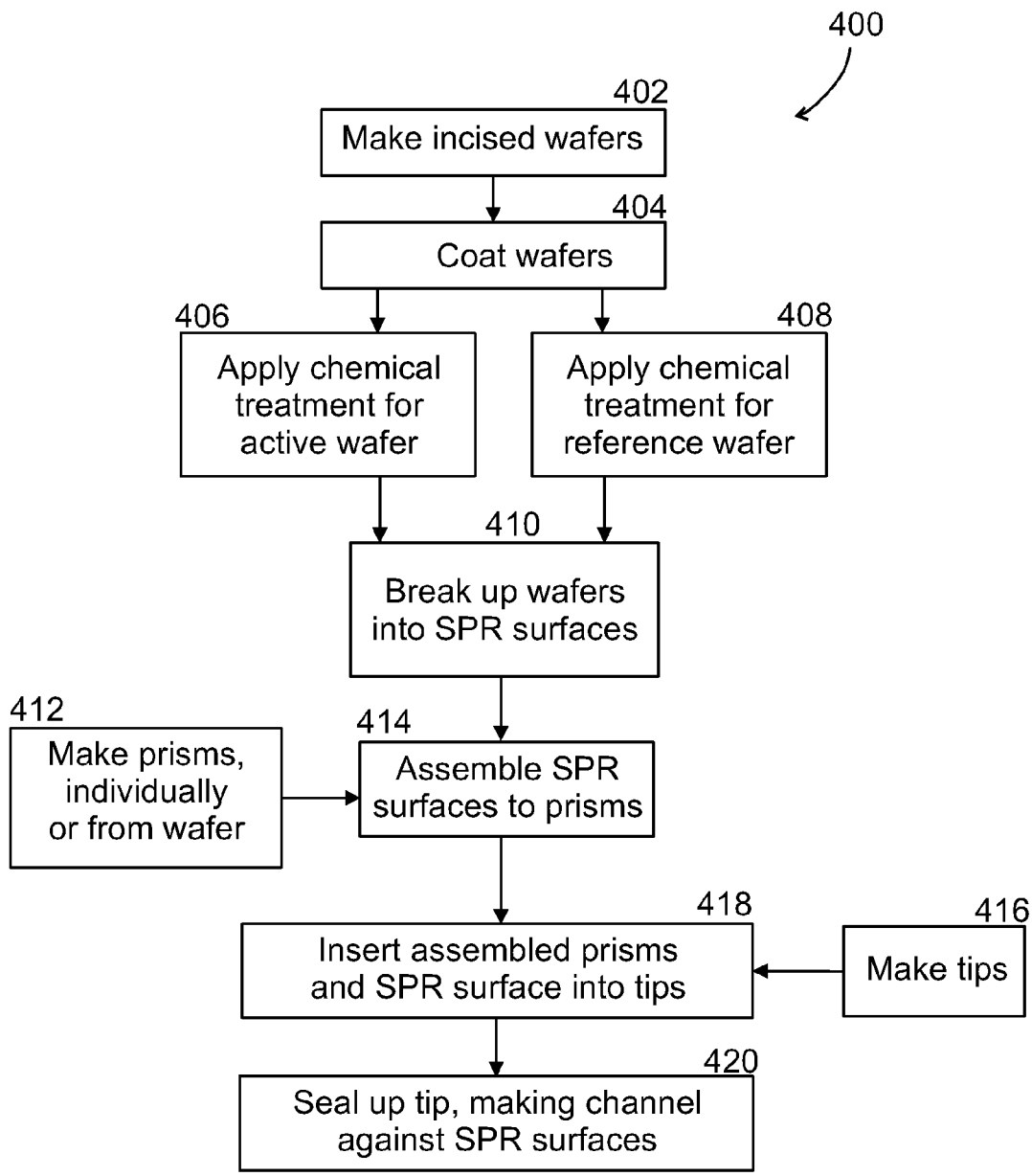
FIGS. 4A-4C are flowcharts showing different methods of manufacturing SPR tips, according to exemplary embodiments of the invention.
Figure 4B:
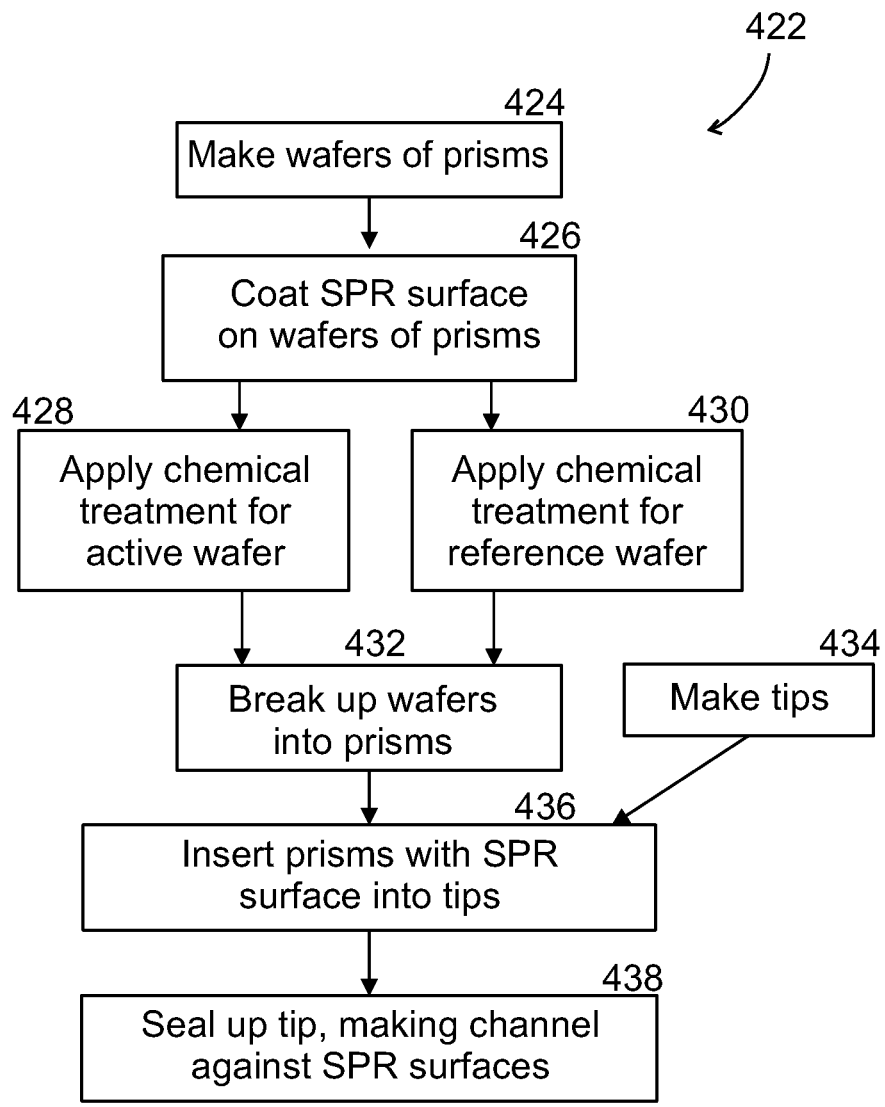
Figure 4C:
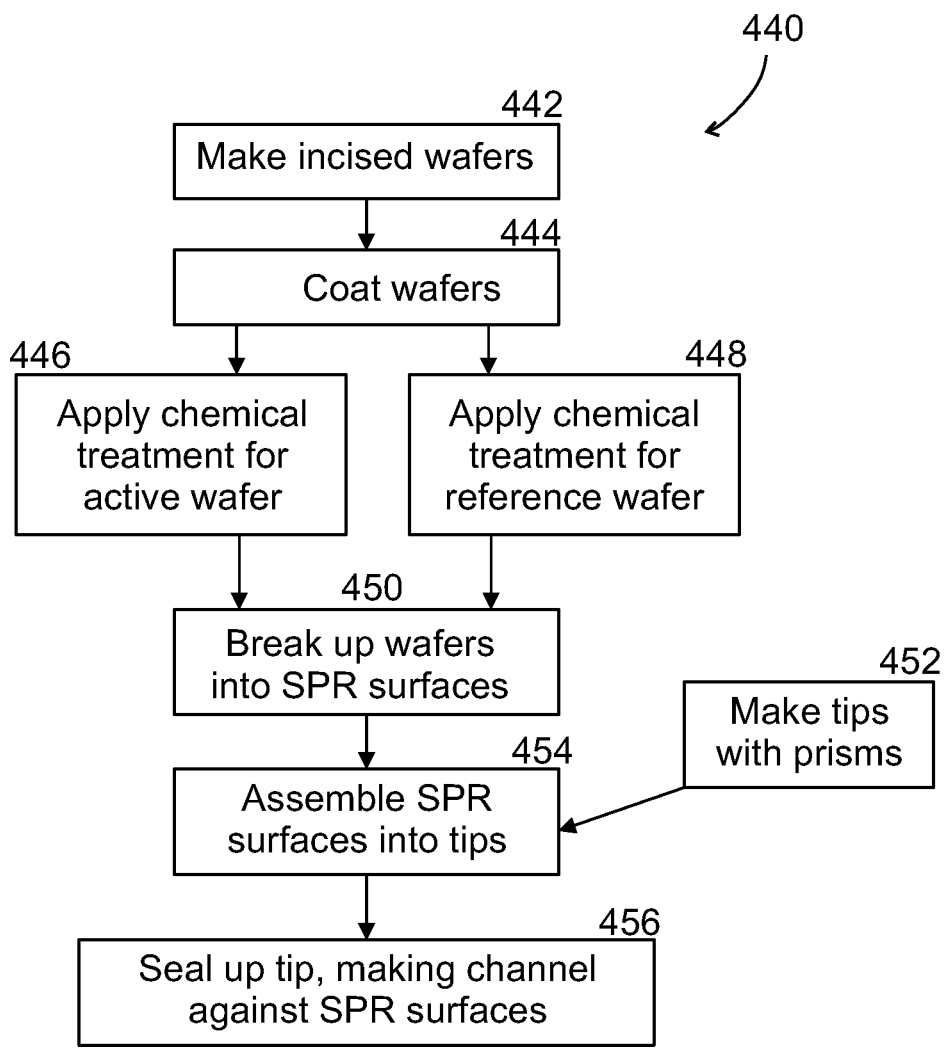

FIGS. 4A-4C show flowcharts for different methods of manufacturing SPR tips, that are inexpensive enough so that the tips can be used only once, or only a few times.

Figure 5:
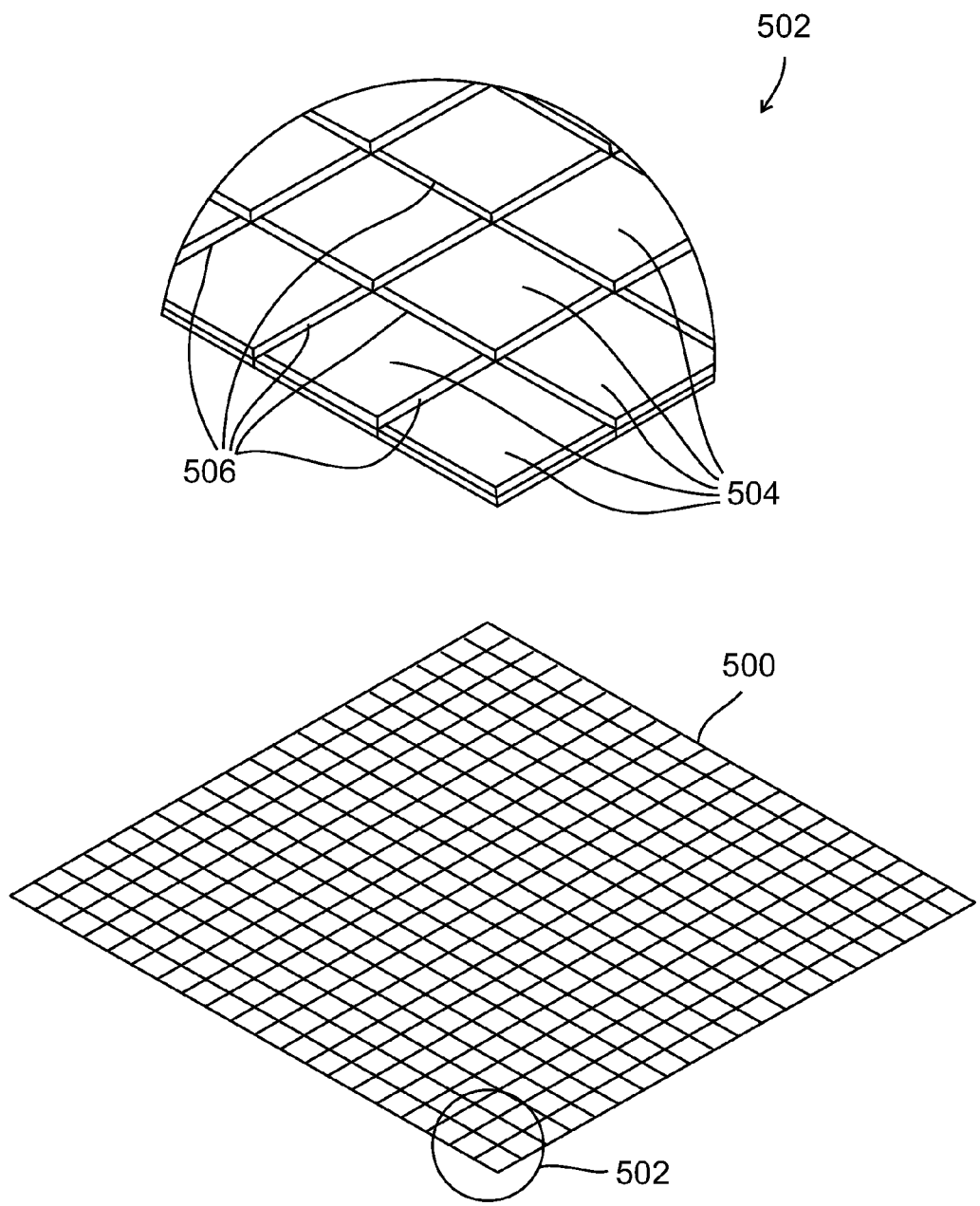
FIG. 5 is a schematic perspective view of a wafer with an array of SPR surfaces, used in the methods of FIGS. 4A and 4C, according to an exemplary embodiment of the invention.

In flowchart 400, shown in FIG. 4A, a wafer with an array of SPR surface elements is made at 402. An example of such a wafer 500 is shown in FIG. 5, and detailed view 502 in FIG. 5 shows the individual SPR surface elements 504, with incised lines 506 between them. Wafer 500 can include, for example, fewer than 10, between 10 and 20, between 20 and 50, between 50 and 100, between 100 and 200, between 200 and 500, between 500 and 1000, between 1000 and 2000, between 2000 and 5000, between 5000 and 10,000, or more than 10,000 individual SPR surfaces. By making a large number of SPR surface elements on a single wafer, performing the relatively expensive steps of applying an SPR film and chemical treatment to the whole wafer, and then breaking the wafer apart into individual SPR surface elements, it is possible to greatly reduce the unit cost of making an SPR surface, compared to the cost of making one SPR surface at a time.

The wafer is optionally molded or cast, from glass, or from a polymer such as epoxy or a plastic. Although making the wafer from plastic has the potential advantage of being less expensive than making it from glass, using glass has the potential advantage that it is easier to apply an SPR film and chemical treatment if glass is used, because of possible adverse chemical reactions with the polymer. The cost per unit is relatively low, even if glass is used, if there are a large enough number of individual SPR surface elements on the wafer. Incised lines 506, demarcating the individual SPR surface elements, are optionally included in the wafer when it is molded or cast, or cut into the wafer with a cutting tool after it is molded or cast.

At 404, the wafer is coated with a thin metallic film that exhibits SPR effects, for example a thin film of gold about 50 nm thick. Optionally, the wafer is first coated with an adhesion film, for example an even thinner layer of chromium or titanium, only a few nm thick, for example about 2 nm thick, for the gold to adhere to. As used herein, "coating with a metallic film that exhibits SPR effects," and similar expressions, refer both to coating the film directly on the surface in question, and to coating it on top of such an adhesion layer. Although the wafer could be coated before any incised lines are cut into it, incising the lines before coating the wafer has the potential advantage that the cutting process will not damage the thin metal coating, which may be easily damaged.

In the method of flowchart 400, different chemical treatments are applied to active and reference SPR surfaces, and since the chemical treatments are applied to the entire wafer, different wafers are used to produce active and reference SPR surfaces. At 406, a chemical treatment is applied to the active wafer, i.e. the wafer that will be used to produce the active SPR surfaces. At 408, a different chemical treatment is applied to the reference wafer, i.e. the wafer that will be used to produce the reference SPR surfaces. The chemical treatment applied to the active wafer allows a ligand, that binds specifically to an analyte to be tested for, to bind to the SPR surface. The chemical treatment applied to the reference wafer does not allow the ligand to bind to the SPR surface, but produces an SPR surface that has similar nonspecific binding properties to the active SPR surface. Further details of the chemical treatments of the active and reference SPR surfaces are described below, in the description of FIGS. 12A and 12B.

At 410, the active and reference wafers are broken into individual SPR surface elements, along the incised lines. Optionally, breaking up the wafers into individual SPR surface elements, and later steps, to be described below, that involve handling the individual SPR surface elements, are done robotically. At 412, prisms are made for each SPR surface element. The prisms may be molded or cast individually, or a number of prisms may be made together on a wafer, which may be molded or cast. The prisms may be made out of glass or out of a polymer such as epoxy, polycarbonate, or another plastic. Making the prisms out of a polymer has the potential advantage that it is less expensive than making them out of glass, and since the SPR surface is not applied directly to the prism in the method of flowchart 400, there is no concern of the chemical treatment of the SPR surface reacting in an adverse way with the polymer. Using glass has the potential advantage that it may have a larger index of refraction and lower birefringence than many polymers, but a recently developed polycarbonate, with index of refraction 1.63 and low birefringence, also has those advantages. Molding or casting the prisms individually has the potential advantage that the mold is a simpler shape and easier to produce than the mold for a wafer with a large number of prisms, but molding or casting a wafer with a large number of prisms has the potential advantage that the unit cost of making a prism is less when a large number of prisms are made at once.

If the prisms are molded or cast out of plastic, then the manufacturing process is optionally done is such a way that the prisms solidify slowly enough in the mold so they do not develop significant internal stresses, especially not internal stresses that are unpredictable, even though this is potentially more expensive than cooling the prisms more quickly. For example, if the prisms are molded, then they are cooled down over a period of at least 5 minutes, or at least 10 minutes, and if the prisms are cast, then they undergo polymerization for at least 1 hours, or at least 2 hours, or at least 3 hours. Such internal stresses can cause changes in the direction of polarization of the light that illuminates the SPR surface, and reflects from the SPR surface, as it passes through the prism. If the state of polarization of the light changes in an unpredictable way, then it will not be known which polarization of light, reaching the linear array detectors, exhibits the dip in reflectivity due to SPR. In this case, in order to be sure of measuring the SPR dip in reflectivity, no polarizing filter is optionally applied to the beam of light, or the beam is optionally divided into two polarized beams of orthogonal polarizations, and the intensity of each beam is measured as a function of angle of incidence on the SPR surface. In either case, for a given available area of the linear array detectors, the signal to noise ratio will potentially be reduced. Alternatively, the change in polarization is measured for each prism, and a polarization rotating element is added to each prism to compensate for the change in polarization, but this may be prohibitively expensive to do individually for each prism.

At 414, each SPR surface element is assembled to a prism. The prisms and SPR surfaces are optionally joined in such as way as to reduce internal reflections from the interface due to mismatch in index of refraction. This is optionally done, for example, by putting a material between a prism and the SPR surface adjoining it, for example a gel, an oil, or an epoxy, that has an index of refraction that will reduce internal reflections, for example an index of refraction that is intermediate between the index of refraction of the prism and the index of refraction of the SPR surface, which is expected to be most effective at reducing internal reflections. Alternatively, the index of refraction of the material placed between the prism and the SPR surface is lower than the index of refraction of either of them, which will be somewhat effective at reducing internal reflections. Such a material may be a good choice, for example, if it has superior adhesive properties for joining the SPR surface to the prism. In some embodiments of the invention, two SPR surface elements, one with an active SPR surface and one with a reference SPR surface, are joined to a single prism.

At 416, before, after, or in parallel with the manufacture of the SPR surfaces and prisms, tips are made, for example out of molded plastic, which has the potential advantage that it is relatively inexpensive for mass production. In the tips made according to the method of flowchart 400, the light enters the prism and leaves the prism through windows in the side of the tip, rather than going through the wall of the tip, so there is no need to cool the molded tips very slowly to avoid internal stresses that might significantly change the polarization of light passing through it, and there is no need to use transparent plastic. Alternatively, light passes through a transparent wall of the tip before entering the prism and/or after the leaving the prism.

At 418, the prisms and SPR surface elements are inserted into the tips, for example through an opening in the side of each tip, Two SPR surfaces and their associated prisms, an active SPR surface and a reference SPR surface, are optionally inserted into each tip. Optionally this is done after the prism has been joined to the SPR surface element. Alternatively, one of them, for example the SPR surface element, is inserted into the tip first, and the other one, for example, the prism, is then inserted into the tip and joined to the SPR surface.

Optionally, the prisms and SPR surface elements are inserted into the tip with the SPR surfaces facing the opening. Alternatively, the SPR surfaces face away from the opening, and the prisms face the opening.

At 420, the tip is sealed up, covering the opening where the prisms and SPR surface elements were inserted, with a plug. When the tip is sealed up, the SPR surface is optionally pressed against a surface, for example an elastomeric surface such as a gasket, with a groove in it, thereby forming a channel which runs along the SPR surface, through which the fluid sample flows when it is drawn into the tip. The gasket also serves to make the tip air tight, so that air is not drawn into the tip when fluid is aspirated into the tip. Optionally, for example if the SPR surface faces the opening, then the gasket is part of the plug, or is a separate element placed between the plug and the SPR surface. Alternatively, for example if the SPR surface faces away from the opening, then the gasket is inserted into the tip before the prism and SPR surface element, and the SPR surface is then pressed against the gasket by the prism, which is pressed against the SPR surface by the plug. Both configurations are shown below in FIGS. 7A, 8, and 10.

FIG. 4B shows a flowchart 422 for an alternative method of making the tips. The method of flowchart 422 differs from the method of flowchart 400, in that the SPR surfaces are coated directly on the prisms in the method of flowchart 422, rather than coating the SPR surface on a separate surface element which is later assembled to a prism, as is done in the method of flowchart 400. Coating the SPR surface directly on the prism has the potential advantage that it avoids the step of joining each SPR surface element to a prism, potentially saving money. But coating the SPR surface on a separate SPR surface element has the potential advantage that the prisms can be made of molded plastic, rather than glass, without any concern about adverse reactions with plastic when the chemical treatment is applied to the SPR surface, and making the prisms out of molded plastic may be less expensive than making them out of glass. Although the SPR surface elements are still optionally made of glass in the method of flowchart 400, making a flat wafer out of glass is potentially much less expensive than making a wafer of prisms out of glass.

Figure 6:
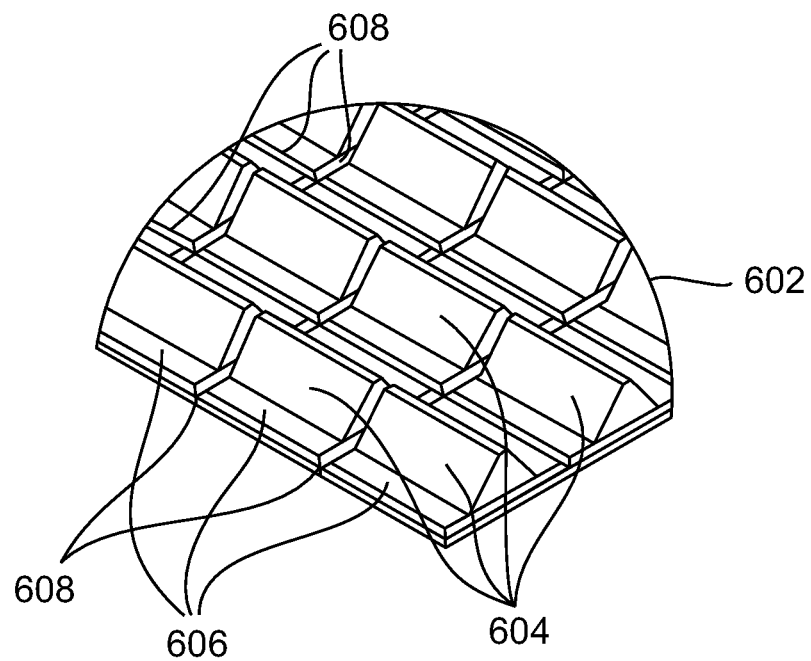
FIG. 6 is a schematic perspective view of a wafer with an array of prisms, used in the method of FIG. 4B, according to an exemplary embodiment of the invention.
Figure 6:
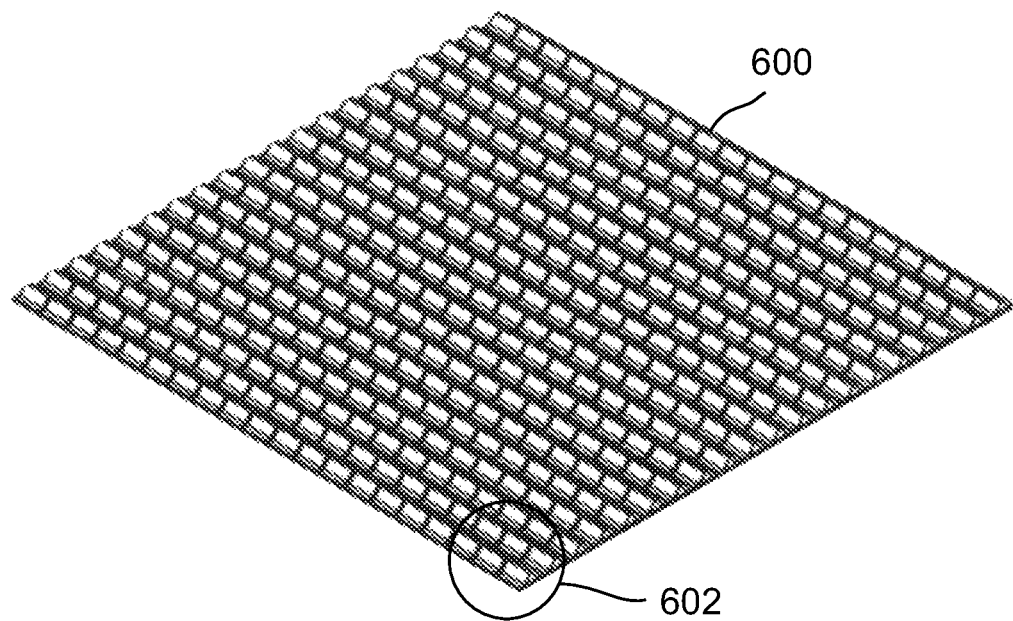

At 424, a wafer is made with an array of prisms. Such a wafer 600 is shown in FIG. 6. A detailed view 602 of FIG. 6 shows individual prisms 604 in the array, separated by incised lines 606. The prisms are optionally molded, for example in glass or in plastic, although if plastic is used, then the SPR coating and surface chemistry is optionally selected so that it can be produced on plastic. Incised lines 606 are optionally molded with the wafer, or are incised in the wafer after the wafer is molded. Optionally, each prism in wafer 600 has an extended thin base portion 608, on which the SPR surface is produced, on the bottom surface of wafer 600 as viewed in detail 602 in FIG. 6. The extended thin base portion potentially makes it easier to break the wafer along the incised lines, and easier to distinguish which surface of the prism is the SPR surface, which may make it easier to assemble the prisms into the SPR tips, particularly if an automated robotic assembly system is used. The parts of the extended portion sticking out beyond the raised part of the prism may also serve as handles which a robotic assembly system could use to pick up the prism.

At 426, the SPR surface, for example a thin film of gold or another metal that exhibits SPR effects, optionally with an adhesion layer such as a thin layer of titanium or chromium, is coated on the bottom surface of the wafers. At 428, a chemical treatment is applied to the active wafer, and at 430 a different chemical treatment is applied to the reference wafer, as in FIG. 4A. The wafers are broken up into individual prisms, with prepared SPR surfaces already on them, at 432. The tips are made at 434, optionally with the same possible characteristics and method of manufacture as in FIG. 4A. The prisms with the SPR surfaces are inserted into the tips at 436, and the tips are sealed up, creating a flow channel along the SPR surfaces, at 438, similarly to FIG. 4A.

FIG. 4C shows a flowchart 440 for still another method of making the tips. In the method of flowchart 440, the prisms are molded together with the tips in a single piece, and the SPR surface elements are assembled to the prisms in the tips. The method of FIG. 4C has the potential advantage over the methods of FIGS. 4A and 4B, that it is not necessary to produce the prism separately and insert it into the tip. But the methods of FIGS. 4A and 4B have the potential advantage that the prism can be made of glass, or molded from plastic but cooled slowly enough, so that it does not have internal stresses that can cause unpredictable changes in polarization of light passing through it. While the entire tip with prism is optionally molded from plastic and cooled very slowly in the method of FIG. 4C, this may make the production of the tip more considerably more expensive than if the tip is cooled more rapidly.

At 442, wafers with an array of SPR surface elements are made, similar to the wafers of SPR surface elements made in the method of flowchart 400, and shown in FIG. 5. At 444, the wafers are coated with a thin film of a metal, such as gold, that exhibits SPR. A chemical treatment is applied to the active wafer at 446, and a different chemical treatment is applied to the reference wafer at 448, as in the method of flowchart 400. The wafers are broken up into individual SPR surface elements at 450, as in the method of flowchart 400.

At 452, tips are made from molded plastic, with prisms included in them, as a single piece. Optionally, there is a single long prism in each tip, for both the active and reference SPR surface element. Alternatively, there are separate prisms for the active and reference SPR surface elements. At 454, the SPR surface elements are inserted into the tips, and joined to the prisms, optionally in a way that avoids a mismatch in index of refraction between the SPR surface element and the prism, which could cause internal reflections of light at the interface between the SPR surface element and the prism. At 456, the tips are sealed up, optionally with a plug covering the opening where the SPR surface elements were inserted. A gasket, part of the plug or a separate element from the plug, optionally forms a flow channel against the SPR surfaces, and prevents air from leaking into the tip when fluid is aspirated into the tip. An example of a tip assembled in this way is shown below in FIGS. 10 and 11.

Figure 7A:
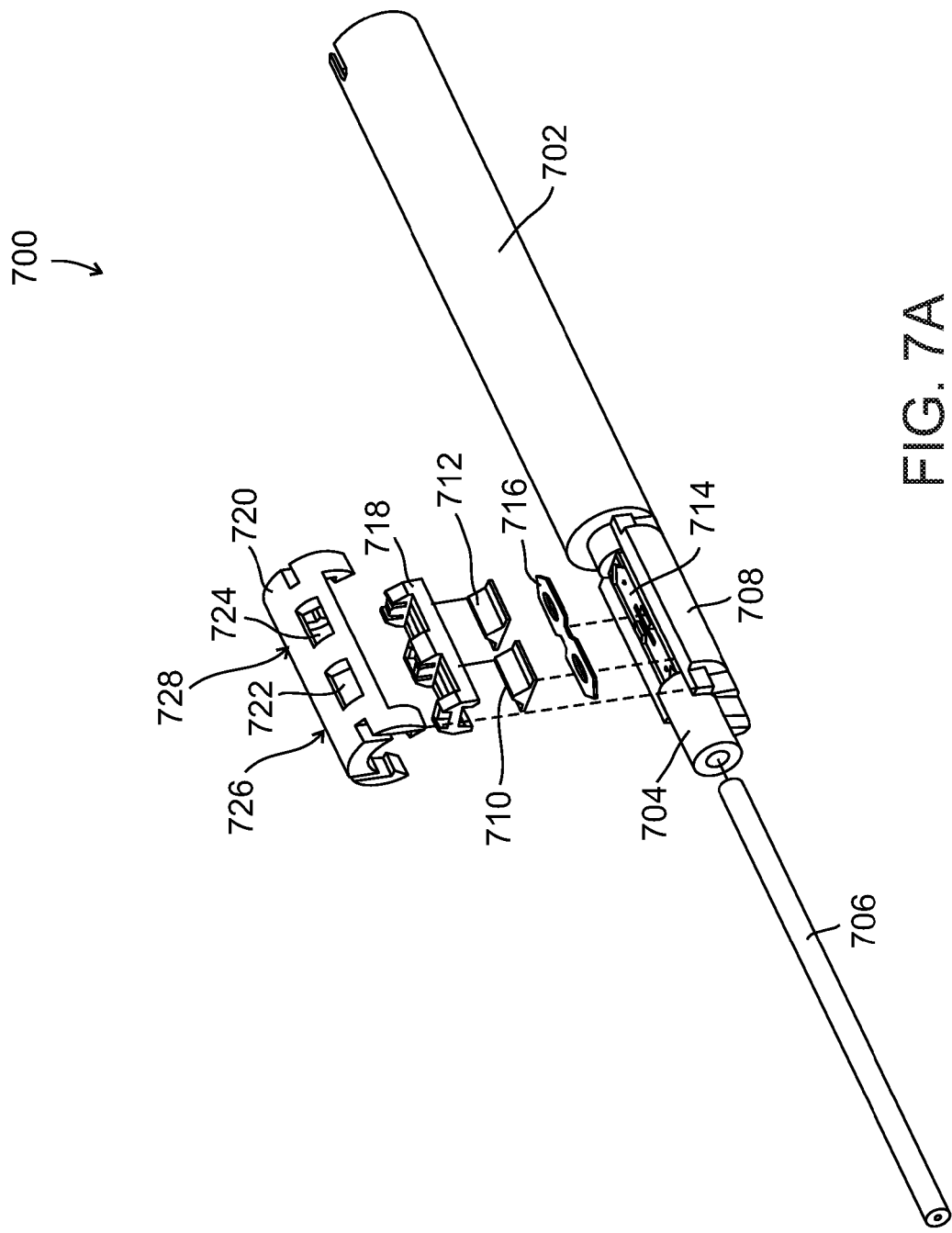
FIG. 7A is a schematic exploded perspective view of the components of an SPR tip made according to the method of FIG. 4B, according to an exemplary embodiment of the invention.
Figure 7B:
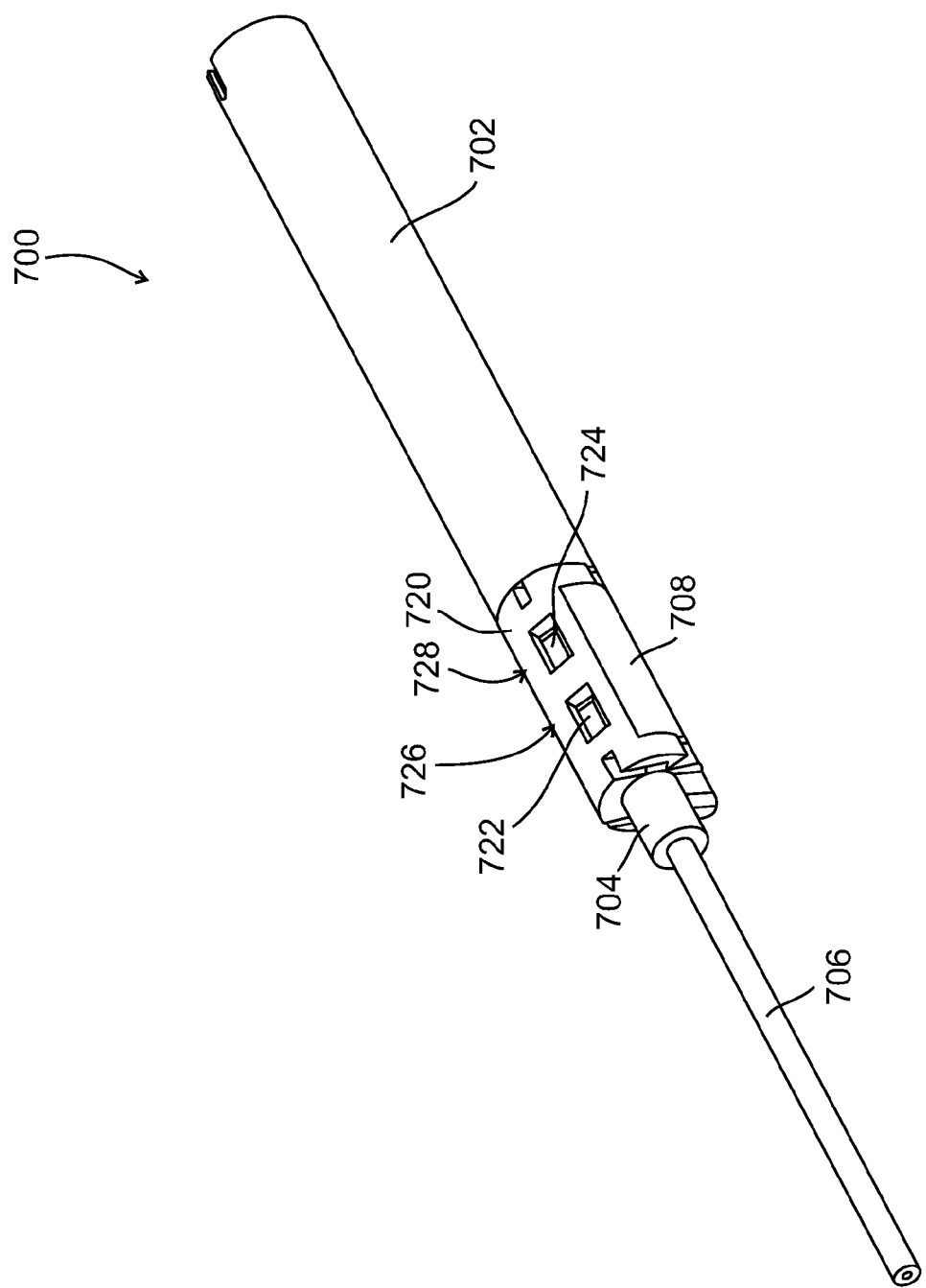
FIG. 7B is a schematic perspective view of the tip when it is assembled.

FIG. 7A shows an exploded perspective view of the parts of a tip 700, made by the method of flowchart 422 in FIG. 4B. The assembled tip is shown in FIG. 7B. A distal portion 702 of the tip, the portion that is closest to the reading head in FIGS. 1A-1C, is attached to a vacuum system when the tip is in use, for drawing fluids into the tip and releasing them. A proximal portion 704 of the tip is attached to a capillary tube 706, which is the part of the tip inserted into the wells in FIGS. 1A-1C. The vacuum system draws fluid into the tip through capillary tube 706, and releases it, for example back into the sample well that it came from, through capillary tube 706. A central portion 708 of the tip holds the SPR surfaces and the prisms through which light is reflected from the SPR surfaces, to measure the SPR curve. In tip 700, the SPR surfaces are coated directly on the prisms. There are two prisms, for example an active prism 710 and a reference prism 712, though the order of the prisms could be reversed. Each prism has an SPR surface coated on its bottom face, as seen in FIG. 7A. The SPR surfaces rest on a base surface 714 of central portion 708 of the tip, with gasket 716 separating the SPR surfaces from base surface 714. The gaskets, SPR surface, and base surface together form the flow channel, through which fluid flows when it is aspirated into the tip, as will be explained below in FIG. 9. A prism holder 718 holds the prisms in place against the gasket, and a cover 720 optionally snaps over the prisms and prism holder, holding all the elements in place. Cover 720 has two windows 722 and 724 on one side of the tip, one window for each prism, and two windows 726 and 728, hidden from view in FIG. 7A, located on the other side of the tip across from windows 722 and 724, respectively, again one window for each prism. The windows on one side, for example windows 722 and 724, are used for light beams to enter the tip and to illuminate the two SPR surfaces through the prisms. After reflecting from the SPR surfaces, the light beams exit the tip through the two windows on the other side, for example windows 726 and 728. Optionally the tip itself is mirror symmetric on the two sides, and which windows are used for the light to enter the tip, and which windows are used for the light to exit the tip, depends on the configuration of the optical sub-system.

It should be understood that, although FIGS. 7A-7B show a tip with two SPR surfaces, the tip design can be modified to accommodate three or more SPR surfaces, for example a reference SPR surface and two or more different active SPR surfaces, with different surface densities of a ligand, or with different ligands. For example, gasket 716, prism holder 718, and cover 720 are optionally lengthened to accommodate three or more prisms and SPR surfaces, arranged along the length of the tip. This is also true of the other tip designs described below.

Figure 8:
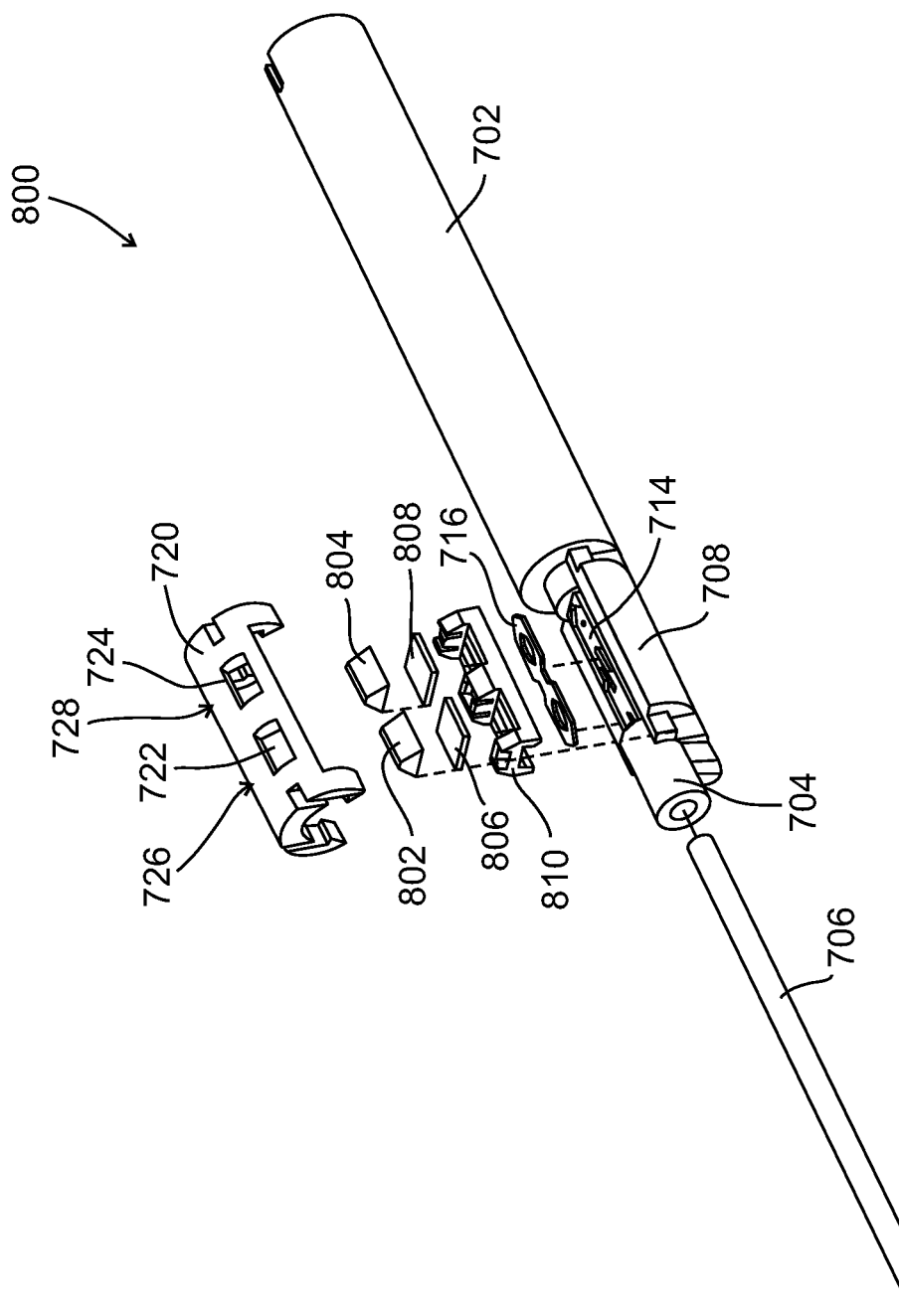
FIG. 8 is a schematic exploded perspective view of the components of an SPR tip made according to the method of FIG. 4A, according to an exemplary embodiment of the invention.

FIG. 8 shows an exploded perspective view of the parts of a tip 800, which is similar to tip 700 but has separate prisms and SPR surface elements, as in the method of flowchart 400 in FIG. 4A. In place of prism 710 and 712 in tip 700, tip 800 has prisms 802 and 804, which are joined respectively to separate SPR surface elements 806 and 808.

Figure 9:
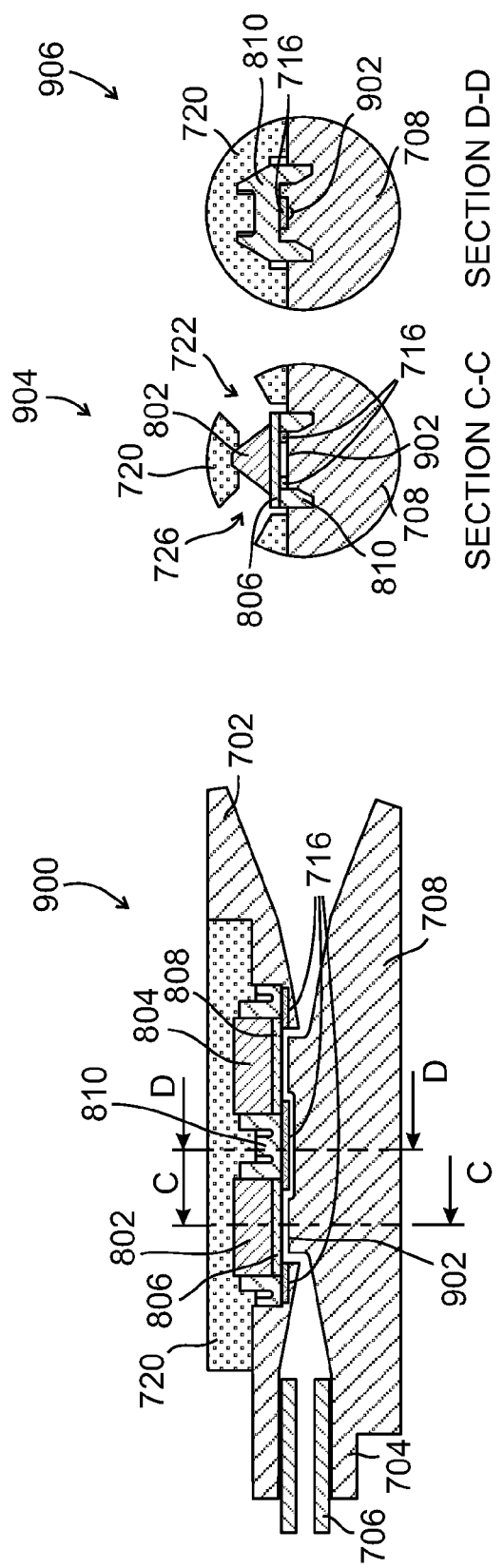
FIG. 9 shows schematic side and axial cross-sectional views of the SPR tip shown in FIG. 8.

FIG. 9 shows a side cross-sectional view 900, and two axial cross-sectional views 904 and 906, of tip 800, showing a flow channel 902 along which fluid flows past the SPR surfaces when it is aspirated into the tip. Tip 700 would look the same, except that the prisms and SPR surface elements would be a single piece. Channel 902 starts, on the left side of view 900, as a continuation of capillary tube 706, going through proximal portion 704. When it reaches central portion 708, channel 902 comes up to the upper surface of central portion 708, the surface labeled 714 in FIGS. 7A and 8, and forms a wide channel along the symmetry plane of the upper surface, directly under SPR surface element 806. The SPR surface on the bottom of element 806 forms the top of this portion of channel 902, and gasket 716 forms its sides. This portion of channel 902 is optionally almost as wide as the SPR surface, as may be seen in axial cross-sectional view 904, making use of most of the surface, which has the potential advantage that the optical system does not have to aim the beam of light so precisely in illuminating the SPR surface, and which potentially allows a higher signal to noise ratio by increasing the area of the SPR surface that contributes to the SPR signal, for a given light source. When it reaches the end of SPR surface element 806, channel 902 gets narrower, and is formed by gasket 716 and the upper surface of central portion 708, either as a groove in gasket 716 or as a groove in the upper surface of central portion 708, or both. Using a groove in only one of them has the potential advantage that the gasket does not have to be aligned so precisely with central portion 708, and having the groove in central portion 708, as shown in axial cross-sectional view 906, has the potential advantages that the cross-sectional size and shape of the channel will not depend on the pressure applied to gasket 716, and that there is no danger that the groove will split the center part of gasket 716 in half, which could cause the gasket to move out of its proper place and not function properly. When it reaches SPR surface element 808, the groove in the upper surface of central portion 708 ends, and channel 902 is again formed by the SPR surface of SRP surface element 808 on top, by the upper surface of central portion 708 on the bottom, and gasket 716 on the sides, similar to axial cross-section 904. At the end of SPR surface element 808, channel 902 goes down into central portion 708, and connects to the inner bore of distal portion 702, which is connected to the vacuum system.

Figure 10A:
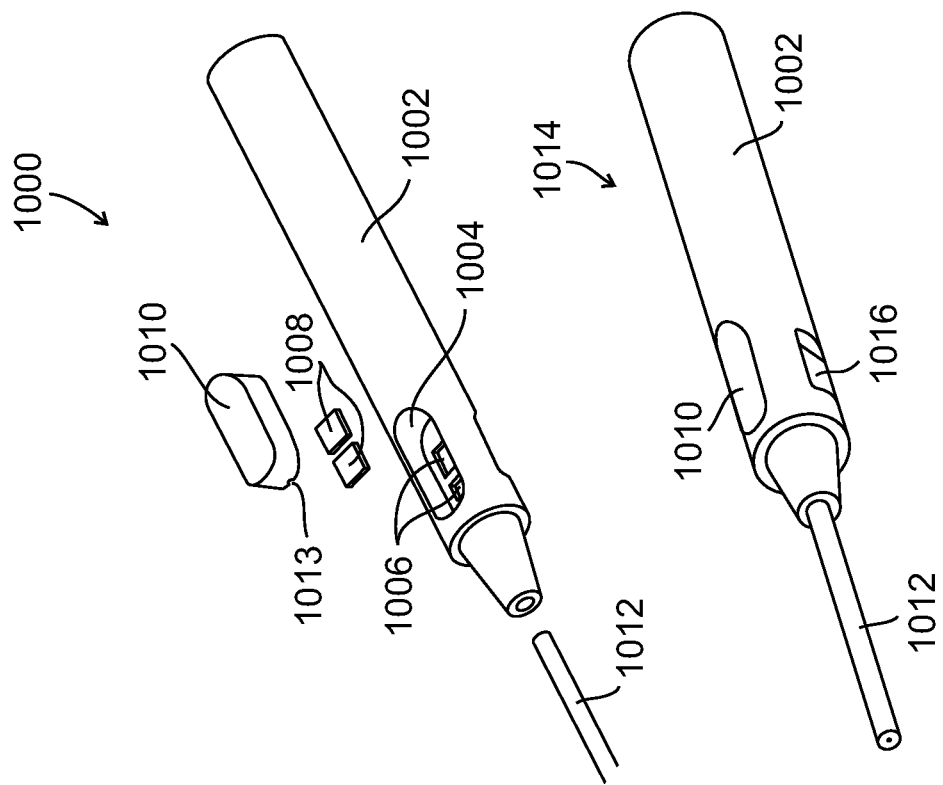
FIG. 10A shows a schematic perspective exploded view of the components of an SPR tip made according to the method of FIG. 4C, and two schematic perspective views of the assembled tip, according to an exemplary embodiment of the invention.
Figure 10A:
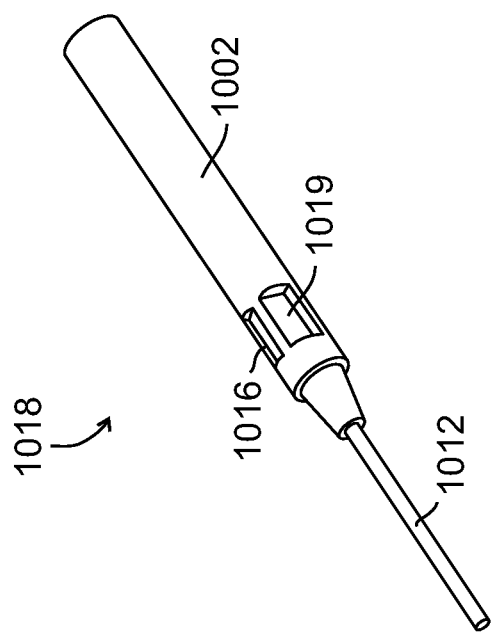

FIG. 10A shows an exploded view 1000 of an SPR tip made according to the method of FIG. 4C, with the prism and the tip made in one piece from molded transparent plastic, and the SPR surface elements made separately and inserted into the tip. The main body 1002 of the tip has an opening 1004 on its side, with two depressions 1006 where two SPR surface elements are inserted, for example an active SPR surface element and a reference SPR surface element. A plug 1010 seals up opening 1004 after the SPR surface elements are inserted, holding the SPR surface elements in place, and preventing air from leaking into the tip when the vacuum system aspirates fluid into the tip through a capillary tube 1012. A groove 1013 in the bottom surface of plug 1010, i.e. the surface that rests against the SPR surfaces, serves as a channel for fluid to flow along the SPR surfaces when it is aspirated into the tip. A perspective view 1014 shows the tip when it is assembled, with main body 1002, plug 1010, and capillary tube 1012 visible from the outside. In perspective view 1014, the tip is rotated slightly upward, so that a prism face 1016 is visible. Perspective view 1018 shows further rotated, so that a second prism face 1019 is visible. These prism faces are an integral part of the molded plastic tip, and provide an optical surface through which light beams enter the tip and illuminate the SPR surfaces, and an optical surface through which the light beams leave the tip after reflecting from the SPR surfaces.

Figure 10B:
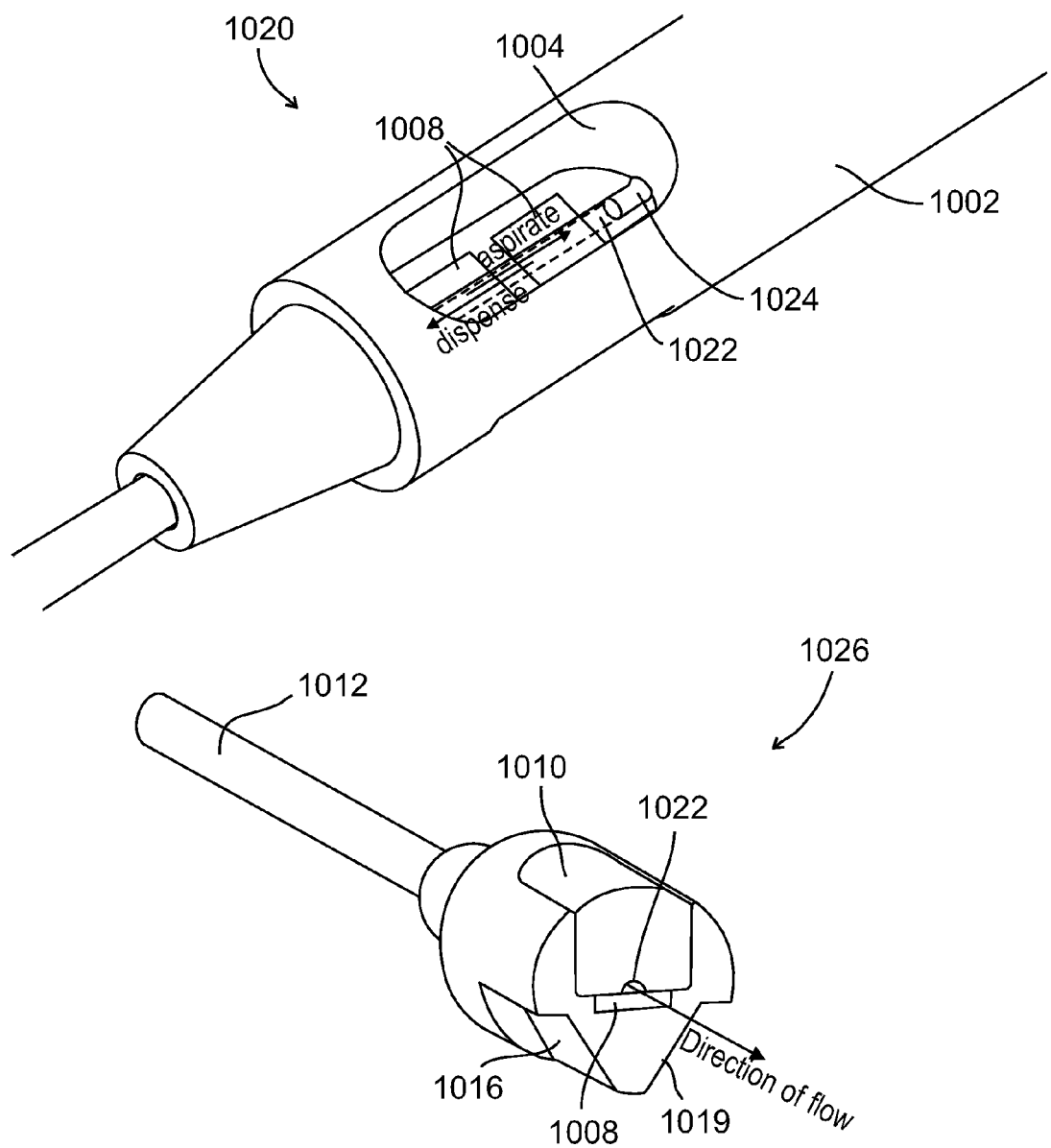
FIG. 10B shows two schematic cutaway perspective views of the SPR tip shown in FIG. 10A.

FIG. 10B shows more detailed views of the interior of the tip shown in FIG. 10A, when it is assembled. A perspective view 1020 looks down into opening 1004, when plug 1010 is in place, but plug 1010 is rendered transparent in the drawing, so SPR surface elements 1008 can be seen at the bottom of opening 1004. A flow channel 1022, along the SPR surfaces of surface elements 1008, is formed from groove 1013 of plug 1010. Another portion 1024 of the flow channel is formed in body 1002 of the tip, and optionally sticks a short distance into groove 1013, to ensure that groove 1013 lines up with the rest of the flow channel. Similarly, a portion of the flow channel that connects to capillary tube 1012, not visible in FIG. 10B, optionally sticks a short distance into groove 1013 on the other end of plug 1010, to ensure that the groove lines up with the flow channel on that side. Cutaway perspective view 1026 shows an axial cross-section of the tip, including plug 1010, SPR surface element 1008, prism faces 1016 and 1019, and flow channel 1022, formed from the groove of the flow channel. The flow channel optionally is aligned with the channel of capillary tube 1012.

Figure 11A:
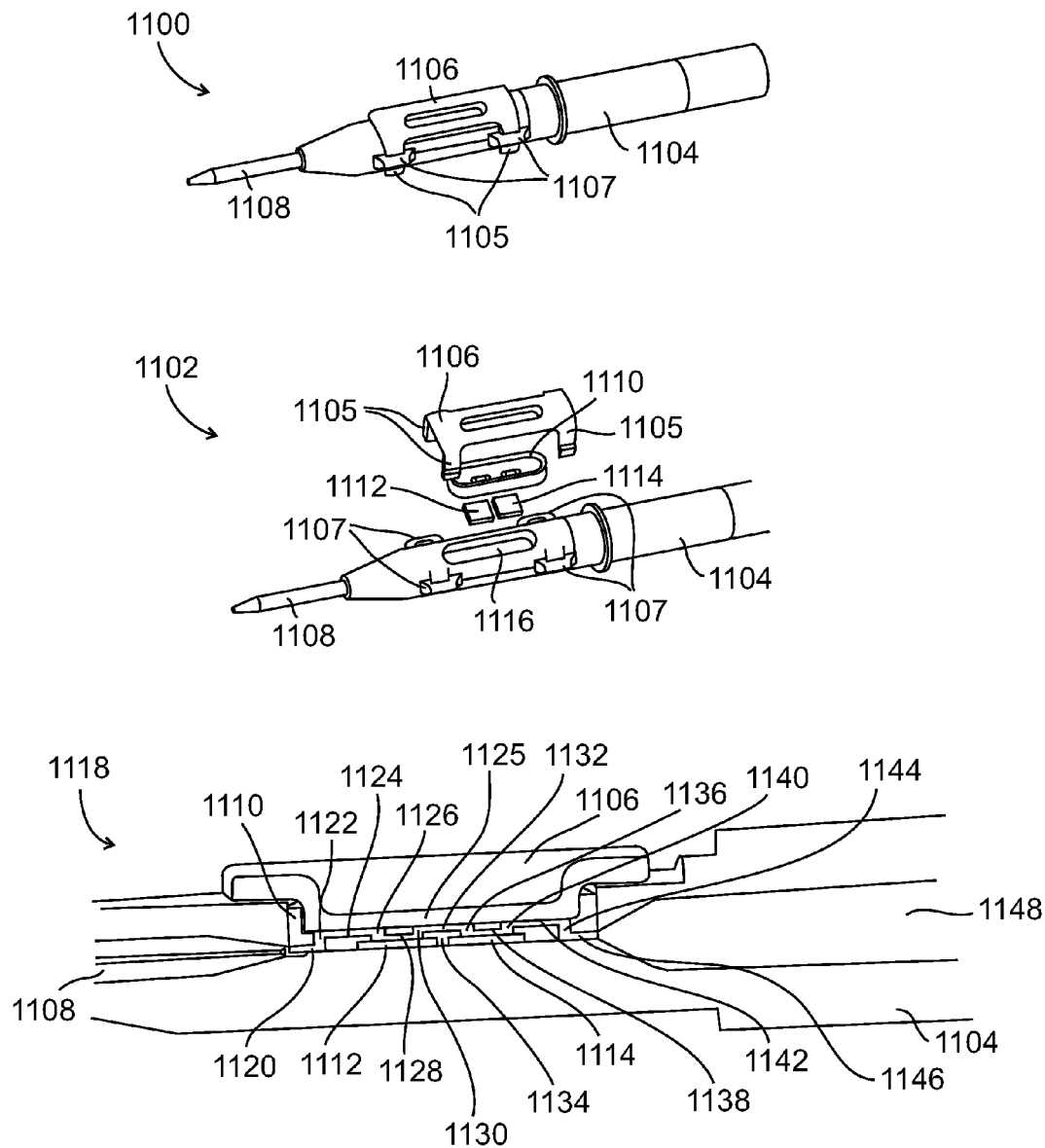
FIG. 11A shows a schematic perspective exploded view of the components of another SPR tip made according to the method of FIG. 4C, a schematic perspective view of the assembled tip, and a schematic side cross-sectional view of the assembled tip, according to an exemplary embodiment of the invention.

FIG. 11A shows an SPR tip according to a different embodiment of the invention, also made according to the method of FIG. 4C. Tip 1100 is shown assembled at the top of FIG. 11A, and its parts are shown in an exploded view in view 1102. A main body 1104 of the tip has a plug 1106, with tabs 1105 that are inserted into slots 1107 on the sides of tip 1100, and click into place. Fluid is aspirated through a capillary tube 1108. Tip 1100 differs from the tip shown in FIGS. 10A and 10B in that there is a gasket 1110, separate from plug 1106, visible in exploded view 1102. Gasket 1110 rests on SPR surface elements 1112 and 1114, for example an active SPR surface element and a reference SPR surface element. The gasket and SPR surface elements are inserted into an opening 1116 in the side of the tip. Gasket 1110 is optionally made of an elastomeric material such as silicone. When plug 1106 clicks into place, it exerts some force on gasket 1110, deforming the gasket slightly, helping the gasket to seal opening 1116, making it air tight.

A side cross-sectional view 1118 shows how gasket 1110, plug 1106, and SPR surface elements 1112 and 1114 define a flow channel, along which fluid flows when it is aspirated into the tip through capillary tube 1108. The flow channel starts on the left, in view 1118, through capillary tube 1108. When it reaches gasket 1110, it goes along a groove in the bottom of gasket 1110, between the gasket and main body 1104. The flow channel then continues upward through a hole 1122 in gasket 1110, and along a groove 1124 in the top of gasket 1110, between the gasket and a bottom surface 1125 of plug 1106. When the flow channel reaches the beginning of SPR surface element 1112, it goes down through a hole 1126 in gasket 1110, and along a groove 1128 on the bottom of gasket 1110, between the gasket and the SPR surface of element 1112. Near the end of SPR surface element 1112, the flow channel goes up through a hole 1130 in gasket 1110, and along a groove 1132 on the top of gasket 1110, between gasket 1110 and lower surface 1125 of plug 1106. This part of the flow channel passes above a spacer 1134 in gasket 1110, which goes between SPR surface elements 1112 and 1114, holding them in place. When the flow channel reaches SPR surface element 1114, it goes down through a hole 1136 is gasket 1110, and along a groove 1138 on the bottom of gasket 1110, between gasket 1110 and the SPR surface of element 1114. Near the end of SPR surface element 1114, the flow channel goes back up through a hole 1140 in gasket 1110, and through a groove 1142 in the top of gasket 1110, between gasket 1110 and lower surface 1125 of plug 1106. Finally, the flow channel goes down through a hole 1144 in gasket 1110, through a groove 1146 in the bottom of gasket 1110, and joins a bore 1148 inside main body 1104, which is connected to the vacuum system.

A potential advantage of having the flow channel go along the top of the gasket in grooves 1124, 1132, and 1142, instead of going along a single long groove at the level of the top of the SPR surface elements, is that this allows the gasket to be thicker in the regions adjacent to and between the SPR surface elements. This thickness of the gasket potentially allows the gasket to retain its shape better and to avoid being torn in those regions, so that it provides a good seal around and between the SPR surface elements, and fluid in the flow channel does not leak out around the SPR surface elements.

Figure 11B:
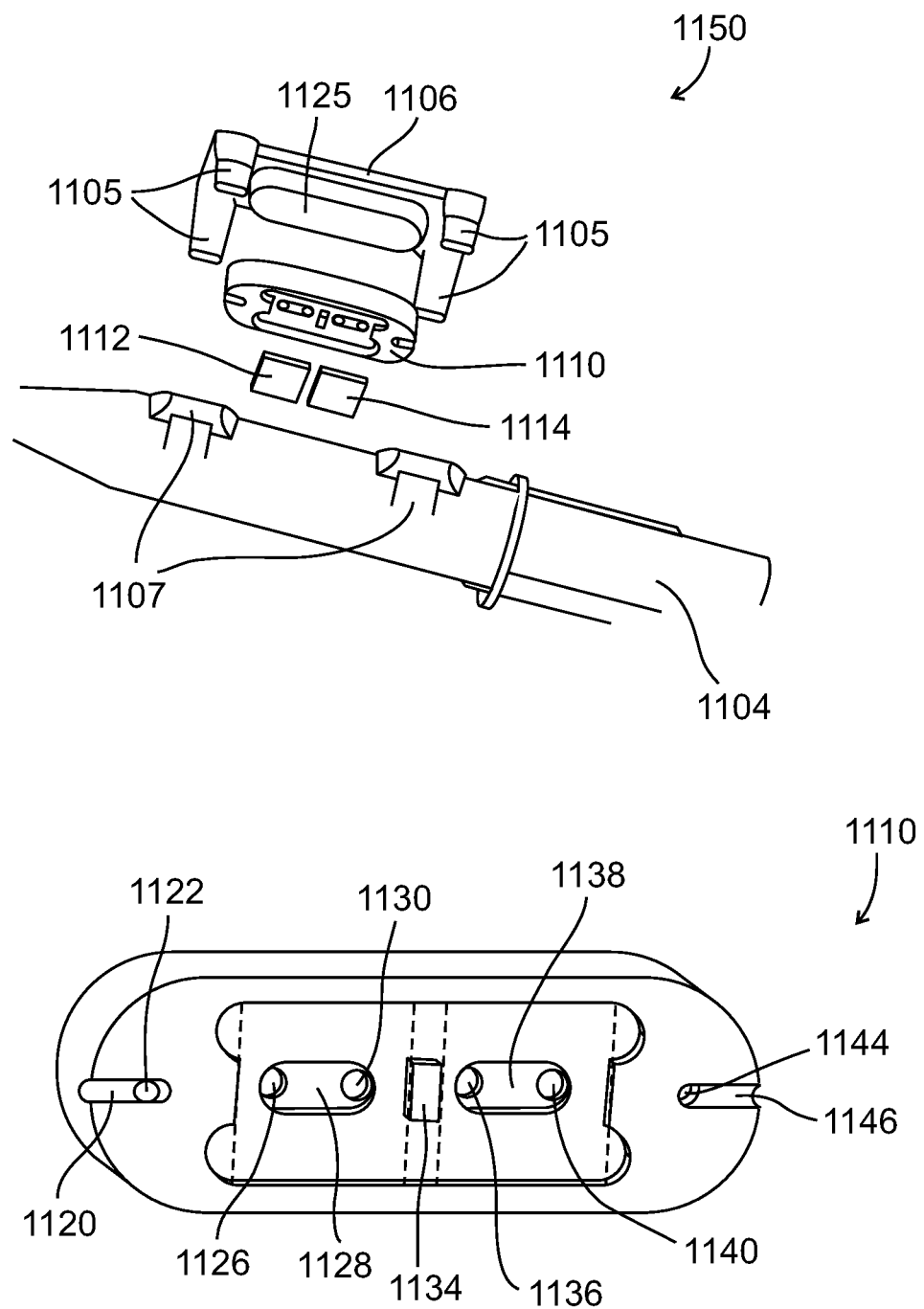
FIG. 11B shows a schematic perspective exploded view of the tip of FIG. 11A, from a different perspective, and a more detailed perspective view of the gasket.

FIG. 11B shows an exploded perspective view 1150, of the same tip shown in FIG. 11A, but from a different angle, below the tip, looking up at plug 1106, gasket 1110, and SPR surface elements 1112 and 1114. The lower surface 1125 of plug 1106, which forms part of the flow channel, is visible in view 1150, and is the lower surface of gasket 1110. A more detailed view of the lower surface of gasket 1110 is shown below view 1150 in FIG. 11B. Outlines of the positions of SPR surface elements 1112 and 1114 are shown with dotted lines. Spacer 1134 is seen between the positions of the two SPR surface elements. Grooves 1120, 1128, 1138, and 1146, in the bottom surface of gasket 1110, and holes 1122, 1126, 1130, 1136, 1140, and 1140, which form part of the flow channel as described above, are also visible in the detailed view of bottom of gasket 1110.

Chemical Treatment of Active and Reference SPR Surfaces

Figure 12A:
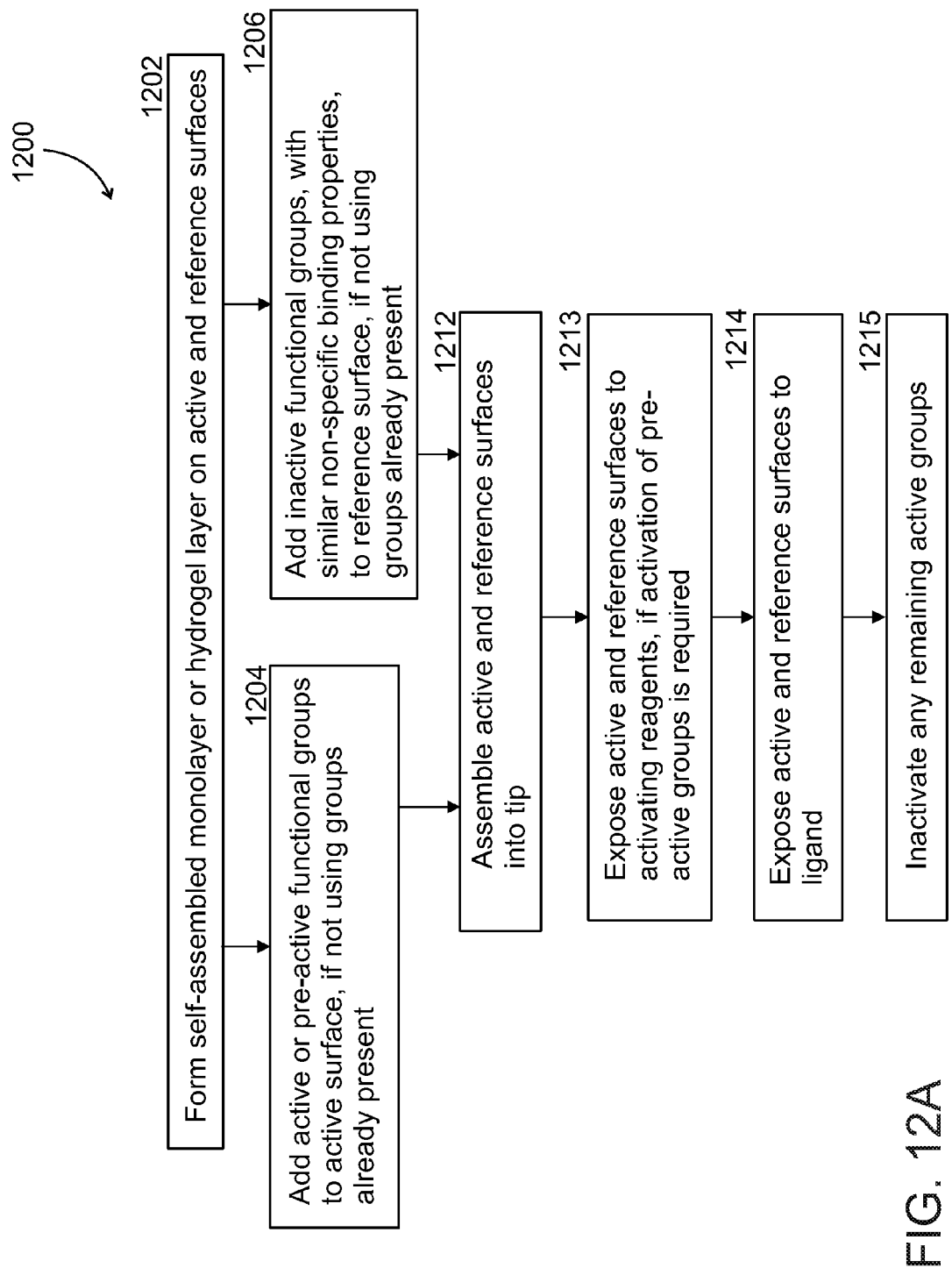
FIGS. 12A and 12B are flow charts showing methods of chemically treating active and reference SPR surfaces, according to exemplary embodiments of the invention.
Figure 12B:
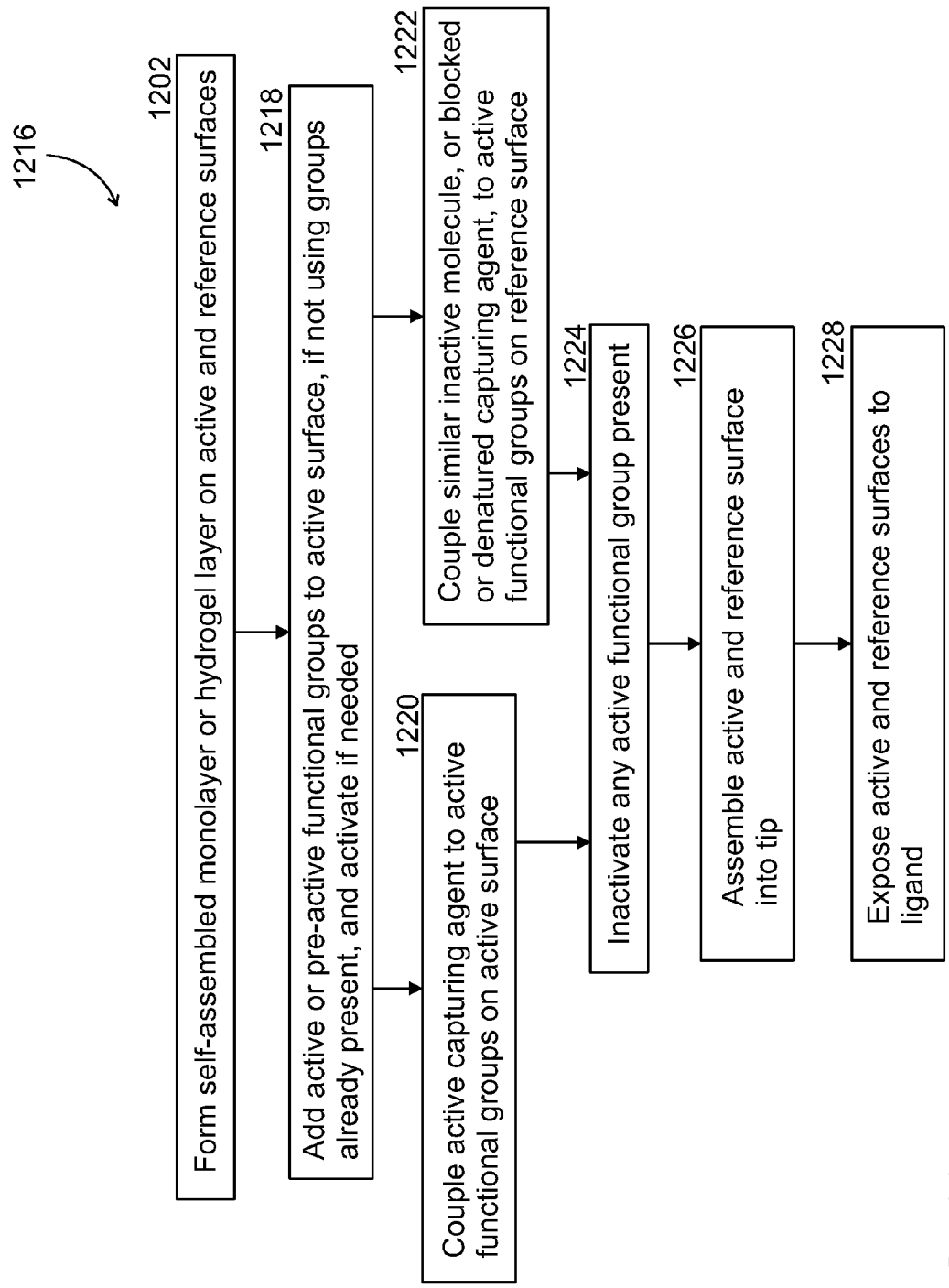

The methods of preparing SPR tips described in FIGS. 4A, 4B, and 4C can include chemically treating an active SPR surface and/or a reference SPR surface in different ways, such that both surfaces can then be exposed to a ligand specific for an analyte of interest, but the ligand will bind only to the active surface, and not to the reference surface. However, it is potentially advantageous if both the active and the reference surface have similar non-specific binding properties, for example to the analyte and to other materials likely to be present in a fluid sample, so that the reference surface can serve effectively as a reference. FIGS. 12A and 12B show flowcharts for two different approaches to methods of chemically treating active and reference SPR surfaces that satisfy these requirements. The methods shown in FIGS. 12A and 12B correspond to two general approaches to binding ligands to an SPR surface: covalent coupling, described in FIG. 12A, and affinity-based capturing, described in FIG. 12B.

FIG. 12A shows a flowchart 1200 for a method of chemically treating an active SPR surface and a reference SPR surface, where the ligand is bound to the active SPR surface using covalent coupling. At 1202, a thin chemical layer, for example a self-assembled monolayer or a hydrogel layer, is formed on both the active and reference surface. Optionally, the layer is hydrophilic, which has the potential advantage of reducing hydrophobic non-specific binding. For example, a polysaccharide layer such as dextran or alginate is used, in the case of a hydrogel layer. In the case of an assembled monolayer, it is formed to contain hydrophilic end groups such as hydroxylic or carboxylic acid groups. Methods of forming such monolayers and hydrogel layers on an SPR surface are described, for example, in U.S. Pat. No. 5,436,161 to Bergström et al; in Stefan Lofas and Bo Johnsson, "A Novel Hydrogel Matrix on Gold Surfaces in Surface Plasmon Resonance Sensors for Fast and Efficient Covalent Mobilization of Ligands," *J. Chem. Soc., Chem. Commun.* (1990), 1526-1528; and in published PCT application WO 2007/049269, "Binding Layer and Methods for its Preparation and Uses Thereof," assigned to Bio-Rad Haifa, Ltd., and with Shai Nimri as the inventor, with the same assignee and one of the same inventors as the present application.

At 1204, active or pre-active functional groups are added to the layer on the active SPR surface, if such groups are not already present. These active functional groups are, for example, groups that can react with an amine group of the ligand, for example if the ligand is a protein, to form a covalent bond. For example, carboxylic acid groups, which are negatively charged, may be used, as well as neutral functional groups, such as epoxide, aldehyde, or acrylate. Alternatively, thiol groups of the ligand may be bound by forming disulfide bonds. One way to add neutral functional groups to the layer, for example, if there are carboxylic acid groups present initially, is to activate the carboxylic acid groups (as will be described below at 1208), and then expose the surface to an excess of a molecule containing amine groups as well as the desired neutral group, such as epoxide, aldehyde, acrylate or disulfide. This is described, for example, by Stefan Lofas et al, "Methods for site controlled coupling to carboxymethyldextran surfaces in surface plasmon resonance sensors," *Biosensors & Bioelectronics* 10 (1995), 813-822.

If active groups such as epoxide, aldehyde, acrylate or disulfide are already present on the active SPR surface, but it is desired instead to use different active groups, then the undesired active groups are optionally inactivated, before adding the desired active groups to the layer of the active SPR surface. This can be done, for example, by exposing the surface to a concentrated solution of small molecules which contain amine groups, such as ethanolamine, that will bind to the active functional groups.

At 1206, inactive functional groups, that will not covalently bond to the ligand, are added to the layer on the reference SPR surface (if not using groups already present), with similar non-specific binding properties to the active functional groups used for the active SPR layer. Non-specific binding can be due to electrostatic attraction between functional groups on the surface and charged groups in the non-specifically binding molecules. Inactive functional groups may have similar electrostatic non-specific binding properties to active functional groups if they have the same sign of charge. For example, sulfate, sulfonate and phosphonate groups are negatively charged functional groups that do not form covalent bonds with amine groups, and have similar electrostatic non-specific binding properties to carboxylic acid groups, which are also negatively charged. So if carboxylic acid groups are the functional groups used on the active SPR surface, then sulfate, sulfonate, and/or phosphonate groups are optionally used, in similar density, on the reference SPR surface. But if neutral functional groups, such as epoxide, aldehyde or acrylate groups, are used for the active SPR surface, then optionally no inactive charged functional groups are added to the reference SPR surface.

At 1212, the active and reference SPR surfaces are assembled into the tip, using, for example, any of the methods described in FIG. 4A, 4B, or 4C.

At 1213, the pre-active functional groups on the active SPR surface, if present, are activated by exposure to activating reagents. For example, carboxylic acid groups will not form covalent bonds with amine groups unless they are exposed to activating reagents, for example a mixture of carbodiimide, such as EDC, and NHS or sulfo-NHS, which form active esters of carboxylic acid groups, such as NHS or sulfo-NHS esters, which do form covalent bonds with amine groups. This is described, for example, in Lofas et al, 1995, and in WO 2007/049269, both cited above. Optionally, this procedure is done by the user, after the active and reference SPR surfaces have been assembled together into the SPR tip, sometimes immediately before using the SPR tip to bind a ligand, since the tip might have a limited shelf life once the surface is activated. In this case, the reference SPR surface may also be exposed to the activating reagents, but they will not activate the reference SPR surface, since it does not contain pre-active groups.

At 1214, the active and reference SPR surfaces are exposed to the ligand, which binds substantially only to the active surface, and not to the reference surface. Optionally, this last procedure is done by the user, sometimes immediately before using the SPR tip to test a sample of the analyte, rather than by the manufacturer, since users may have their own specialized ligands they want to use, and since the tip might have a limited shelf life once the ligand is attached to the active surface.

At 1215, any active functional groups remaining on the active surface or on the reference surface are optionally inactivated. This can be done, for example, by exposing the surface to a concentrated solution of small molecules which contain amine groups, such as ethanolamine, that will bind to the active functional groups. This procedure would also be done by the user, if exposing the surfaces to the ligand is done by the user. Once the ligand has been bound to the active SPR surface, it may be advantageous to inactivate any remaining active functional groups on the SPR surfaces, so materials in the sample do not bind to the active functional groups, but only to the ligand, which is specific for the analyte.

FIG. 12B shows a flowchart 1216, for a method of chemically treating active and reference SPR surfaces, in a case where the ligand is bound to the active SPR surface using affinity-based capturing. At 1202, a thin chemical layer such as a self-assembled monolayer or hydrogel layer is formed on the active and reference SPR surfaces, as in FIG. 12A. At 1218, active or pre-active functional groups are added, if not already present, and activated, if needed, as in 1204 and 1213 of FIG. 12A, but this is optionally done for both the active and reference SPR surfaces. At 1220, an active capturing agent is coupled to active functional groups on the active SPR surface. For example, if the ligand is a biotin-labeled molecule, the active capturing agent is optionally avidin or an avidin derivative, which can be bound to the surface layer using, for example, the method described in Lofas et al, 1995, cited above. If the ligand is an antibody, the capturing agent is optionally a protein with a high affinity to the antibody, such as protein A, protein G, or a secondary antibody. Capturing agents that are proteins can, for example, be bound to the layer by active functional groups that form covalent bonds with amine groups, as described above in the description of FIG. 12A. If the ligand is a recombinant tagged protein, the capture agent is, for example, a molecule with a high affinity to the tag of that protein. For example, Ni(II) activated complexes of nitrilo triacetic acid (NTA) are optionally used to capture polyhistidine-tagged proteins. This is described, for example, by Lata and Piehler, "Stable and Functional Immobilization of Histidine-Tagged Proteins via Multivalent Chelator Headgroups on a Molecular Poly(ethylene glycol) Brush," *Anal. Chem.* 77, 1096-1105 (2005).

At 1222, an inactive molecule, similar to the active capturing agent, is coupled to the layer of the reference SPR surface. For example, the inactive molecule is the same as the active capturing agent, but it is inactivated by binding it to a high concentration of a small molecule that binds to the same active site that the ligand binds to. For example, if the capturing agent is avidin, it can be inactivated by exposing it to biotin. Alternatively, if the active capturing agent is a protein, then the inactive molecule is optionally a different protein with similar molecular weight and isoelectric point (pI) value, which does not bind to the ligand. Alternatively, if the active capturing agent is a protein, then the inactive molecule is optionally the same protein, but denatured by exposing it to high temperature or extreme pH conditions.

At 1224, any active functional groups remaining on the reference SPR surface are optionally inactivated, as described above for 1215. Optionally this is also done for the active SPR surface, after the capturing agent has been bound to it.

At 1226, the active and reference SPR surfaces are assembled into the tip, using for example any of the methods described in FIGS. 4A, 4B, and 4C. At 1228, the active and reference SPR surfaces are exposed to the ligand, which binds substantially only to the active surface, as described above for 1214.

Alternative Method of Preparing an SPR Tip

Figure 13:
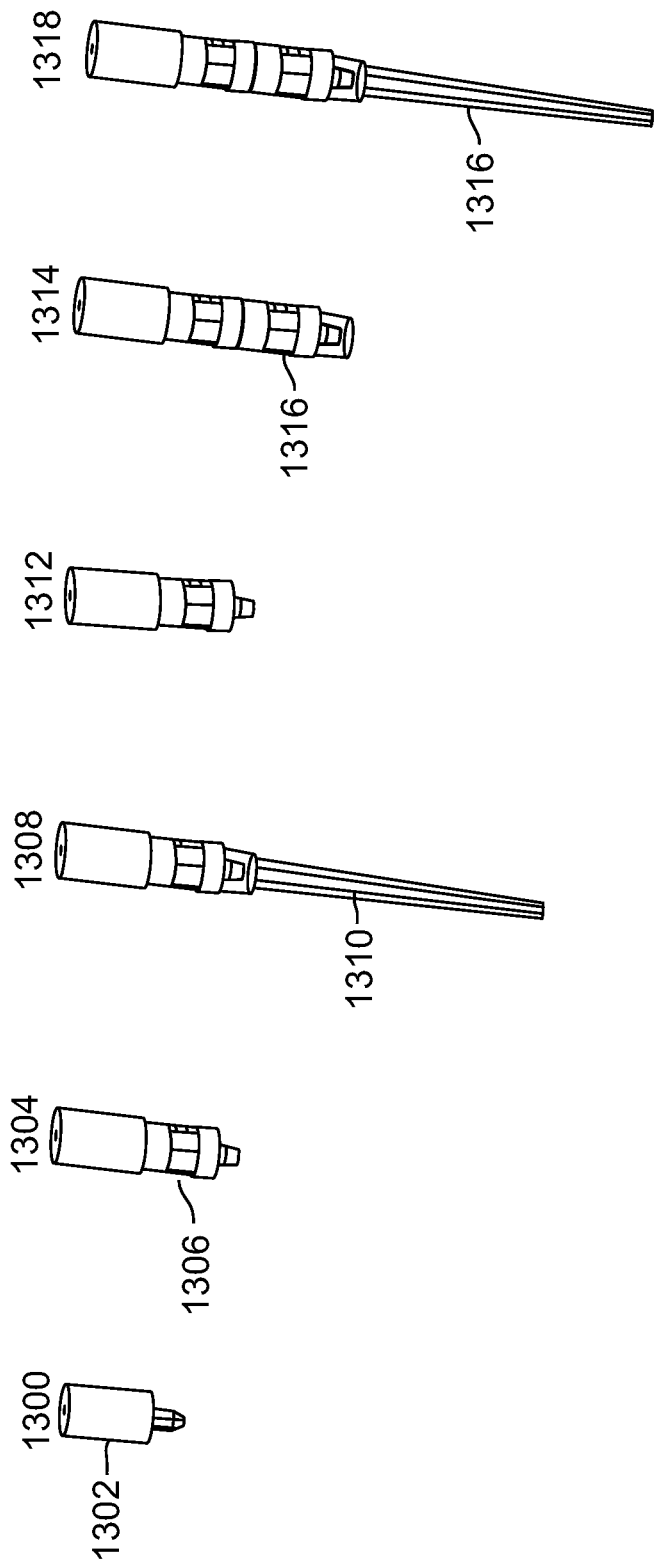
FIG. 13 is a schematic perspective view of steps in making an SPR tip with active and reference SPR surfaces, according to an exemplary embodiment of the invention.
Figure 14:
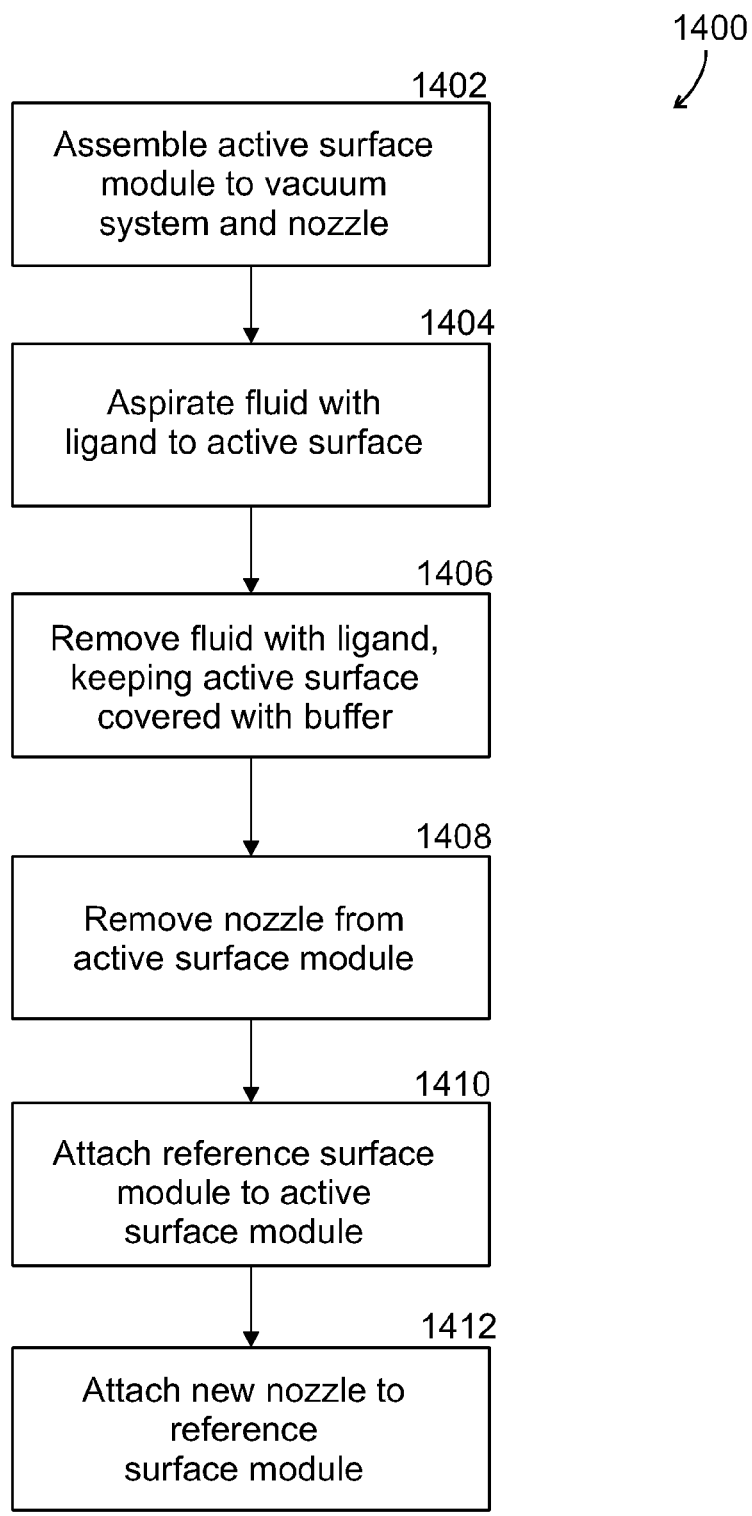
FIG. 14 is a flow chart showing the method of FIG. 13.

FIG. 13 shows a time sequence for the preparation of an SPR tip, according to a procedure shown in a flowchart 1400 of FIG. 14, in which the active SPR surface and reference SPR surface need not be given different chemical treatments. The method of FIG. 14 has the potential advantage over the methods of FIGS. 4A-4C, that there is no need to perform two different chemical treatments for the active SPR surfaces and the reference SPR surfaces. But the methods of FIGS. 4A-4C have the potential advantage that the SPR tip may be easier and less expensive to assemble. In particular, assembling a tip automatically according to the method of FIG. 14 may require more sophisticated and expensive robotics.

At 1300 of FIG. 13, an upper portion 1302 of an SPR tip is shown, which provides a coupling of the tip to a vacuum system, which is used to aspirate fluids into the tip, and to release them. At 1304, upper portion 1302 is joined to a module 1306, which includes an SPR surface, which will serve as the active SPR surface, and a prism, through which a light beam illuminates the SPR surface, reflects from it, and exits the SPR tip, eventually reaching a detector, as described above in the description of FIGS. 3A-3F. Optionally, the SPR surface in module 1306 is prepared first as part of an array of SPR surface elements in a wafer, which is later broken up, and each individual SPR surface elements is then inserted into a module like module 1306, similar to what was described above in FIGS. 4A-4C. Optionally, the SPR surface in module 1306 has received a chemical treatment making the surface capable of binding to a ligand specific for an analyte of interest, as described in FIG. 12A or FIG. 12B for the active SPR surface.

At 1308, as stated at 1402 in FIG. 14, module 1306 is joined to a tip 1310. At 1404 in FIG. 14, fluid with a ligand is aspirated into the tip, using the vacuum system connected to upper portion 1302, so that it reaches the active SPR surface in module 1306, and the ligand binds to the active SPR surface. The fluid with ligand is then removed, at 1406, optionally keeping the active SPR surface covered with a buffer fluid so it does not dry out or become exposed to oxygen. Optionally, any part of the chemical treatment that is done after binding the ligand to the surface, such as inactivating remaining active functional groups on the SPR surface, as described above in FIGS. 12A and 12B, is performed, using the vacuum system to aspirate the needed reagents into the tip, so that they reach the active SPR surface, and releasing the reagents when the chemical treatment is complete. Alternatively, this part of the chemical treatment is done later, if the same chemical treatment is to be done to the reference SPR surface, as will be described.

When the active SPR surface has been prepared with ligand bound and chemical treatment complete, nozzle 1310 is removed from module 1306, leaving only module 1306 and upper portion 1302, as shown at 1312 in FIG. 13. At 1410, a second module 1316, which contains what will be the reference SPR surface, is attached to module 1306, as shown at 1314 in FIG. 13. Optionally, module 1316 was prepared in a manner identical to module 1306 before the ligand was bound to the SPR surface in module 1306, and modules 1306 and 1316 are taken from a single supply of prepared modules. But the SPR surface in module 1316 acts as a reference SPR surface, because it does not undergo the procedure of binding the ligand. At 1412, a nozzle 1320, optionally a new nozzle without any of the fluid with the ligand in it, is attached to the end of module 1316, as shown at 1318 in FIG. 13. Optionally, if there is a part of the chemical treatment that is applied to both the active and reference SPR surfaces, such as inactivating any active functional groups, then this procedure is done now, by using the vacuum system to aspirate the reagent used, so it reaches both the active and reference SPR surfaces, and then releasing it.

The final result is an SPR tip, containing both an active SPR surface and a reference SPR surface, ready to use for testing a fluid sample.

It is expected that during the life of a patent maturing from this application many relevant optical detection systems, using light that reflects from a surface that an analyte binds to, will be developed, and many methods of chemically treating such surfaces, to block them from binding or to allow them to bind to a ligand, and the scope of the terms "optical detection system" and "chemical treatment" is intended to include all such new technologies a priori.

As used herein the term "about" refers to ±10%.

As used herein, directions are "substantially parallel" if they are parallel to within 20 degrees, and "substantially perpendicular" if they are within 20 degrees of being perpendicular to each other. As used herein, two paths are "substantially the same" but displaced from each other, if they consist of corresponding segments that have the same length within a factor of 1.3, and are oriented substantially parallel to each other.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Figure 15:
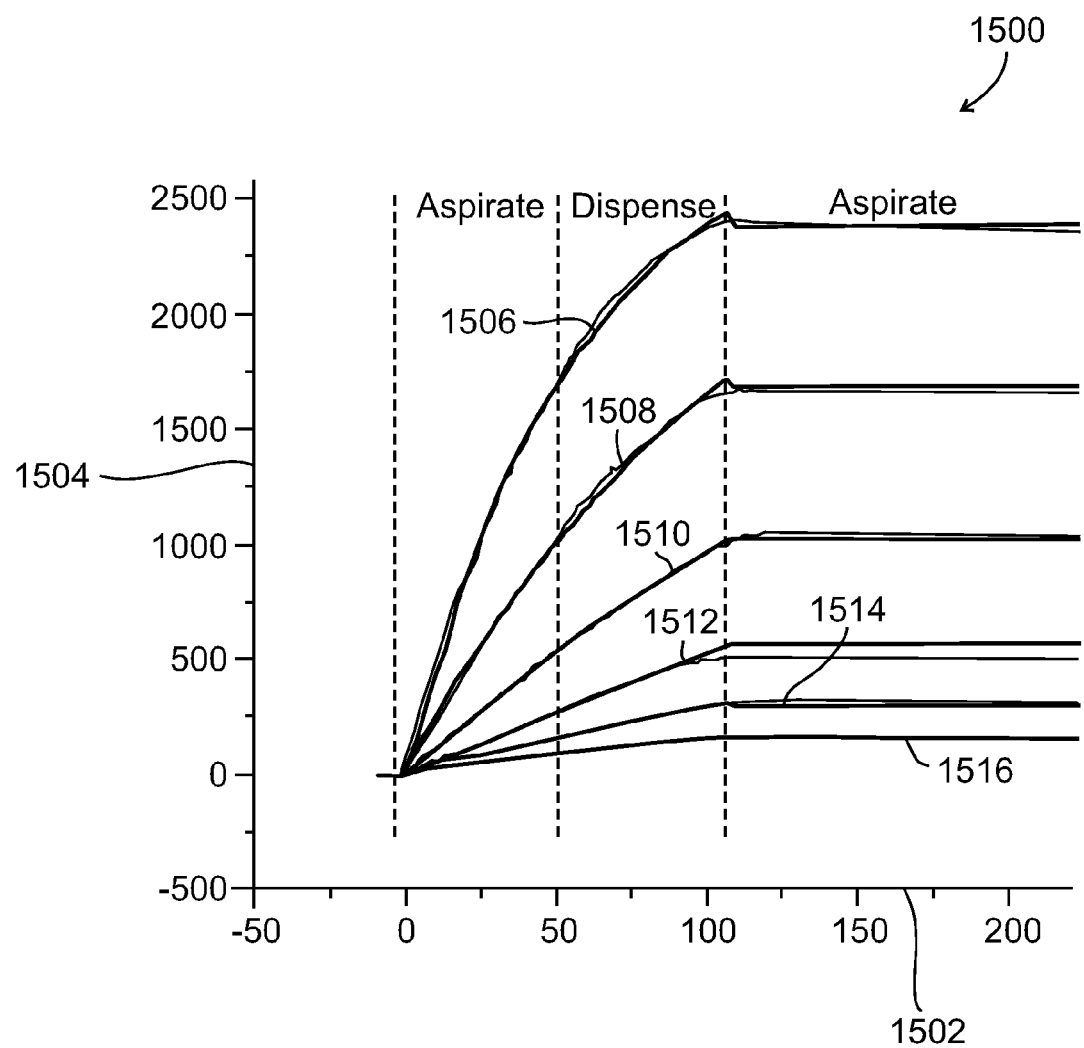
FIG. 15 is a plot of the thickness of a layer of an analyte on an SPR detection surface, as a function of time, while aspirating and dispensing a fluid sample, in a test of an SPR tip similar to the tip shown in FIGS. 11A and 11B, in accordance with an exemplary embodiment of the invention.

Reference is now made to the following examples, which together with the above descriptions illustrate some embodiments of the invention in a non limiting fashion. FIG. 15 is a plot 1500 showing the results of a test made by the inventors using a prototype SPR tip similar in design to the tip shown in FIGS. 11A and 11B, with an outer diameter of 5 mm. Fluid samples were tested with six different concentrations of human immunoglobin G (IgG), 100, 50, 25, 12.5, 6.25 and 3.125 nM, using Protein A as a ligand on the active detection surface. The density of ligand on the surface was 1000 RU, where 1 RU (SPR response unit) corresponds to a change in refractive index of 1 part in $10^6$ at the SPR surface. Each fluid sample was about 200 microliters. Two tests were made for each concentration. The change in the amount of analyte adhering on the active surface, and on a reference surface with similar non-specific binding properties, were measured in each test as a function of time, while aspirating the sample for 50 seconds, then dispensing the sample back into the well for 60 seconds. Following this, buffer solution, without any of the analyte, was aspirated for 120 seconds, then dispensed for 90 seconds, and aspirated again for 120 seconds. For each concentrate of the analyte, the amount of analyte adhering on the reference surface, as a function of time, was subtracted from the amount of analyte adhering on the detection surface, and the results are shown in plot 1500. A horizontal axis 1502 shows the time in seconds, starting from the time when aspiration of the sample began, and a vertical axis 1504 shows the difference in the amount of attached analyte on the active detection surface and on the reference surface, in RU. The amount of attached analyte was calibrated by comparing the results to a fluid sample with 1 milligram of glucose per milliliter of water, which is known to produce a change in SPR angle of 142 RU. Curves 1506, 1508, 1510, 1512, 1514, and 1516 show the difference in thickness as function of time for each of the six concentrations, respectively 100, 50, 25, 12.5, 6.25 and 3.125 nM. The two curves generated for each concentration are in all cases very close together, demonstrating repeatability. The reaction constants ka (association constant), kd (dissociation constant), and KD (equilibrium constant kd/ka) of the analyte and the ligand were calculated by fitting the curves to a model. The result was in very good agreement with an assay done using an off-the-shelf SPR system, the ProteOn system, made by Bio-Rad. The difference in ka was 7%, the difference in kd was 30%, and the difference in KD was 24%, all within the normal range of variation in these reaction constants between different batches of Human IgG and Protein A.

It should be noted that there is no visible jump or change in slope, at the time when the aspiration of the sample ends and the dispensing of the sample begins, reversing the direction of flow past the active and reference surfaces. This shows that very little buffer solution mixes with the fluid sample, as it flows past the detection surfaces into the tip. Once the sample is dispensed, and buffer solution is aspirated and dispensed, there is very little further change in the thickness of the layer, only about 2%. This shows that very little of the sample mixes with the buffer solution already in the tip, and remains in the tip, after the sample is nominally completely dispensed back into the well, and very little of the analyte is removed from the layer by buffer solution flowing past it.

These results show that an accurate measurement of concentration of a biomolecule, at biologically relevant concentrations, can be made with this tip design, and that configuration of the flow chamber is such that there is little mixing between the fluid sample and the buffer solution.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A tip for use in an optical detection system to analyze an analyte in a fluid sample drawn into the tip, using light reflected from a detection surface inside the tip that the analyte binds to, comprising:
   at least one active surface having a surface chemistry with at least one functional group that allows it to form a covalent bond with at least one amine group of a ligand; and
   at least one reference surface having a surface chemistry that do not form a covalent bond with said at least one amine group of said ligand;
   wherein said functional groups of said active surface and said reference surface have similar non-specific binding properties;
   wherein said at least one functional group of said at least one active surface comprises a carboxylic group; and
   wherein said at least one functional group of said at least one reference surface comprises at least one functional group selected from the group consisting of sulfate, sulfonate, and phosphonate groups.

2. A tip according to claim 1, wherein said at least one active surface and at least one reference surface are SPR surfaces.

3. A tip according to claim 1, wherein said at least one functional group of said at least one reference surface is used with similar density to said at least one carboxylic group of said at least one active surface.

4. A tip according to claim 1, wherein said at least one functional group of said at least one active surface comprises at least one neutrally charged functional group.

5. A tip according to claim 4, wherein said at least one neutrally charged functional group is selected from the group consisting of epoxide, and/or aldehyde, and acrylate.

6. A tip according to claim 1, wherein said at least one active surface comprises at least two active surfaces having surface chemistries that bind different ligands which bind to different analytes such that said tip detects two or more different analytes in the same fluid sample.

7. A tip according to claim 1, wherein said at least one active surface comprises at least two active surfaces having surface chemistries that bind different ligands, which bind the same analyte such that said tip studies the reaction kinetics of said analyte with two different ligands.

8. A tip for use in an optical detection system to analyze an analyte in a fluid sample drawn into the tip, using light reflected from a detection surface inside the tip that the analyte binds to, comprising:
   at least one active surface having a surface chemistry with at least one functional group that allows it to form a covalent bond with at least one amine group of a ligand;
   at least one reference surface having a surface chemistry that do not form a covalent bond with said at least one amine group of said ligand;
   wherein said functional groups of said active surface and said reference surface have similar non-specific binding properties, and wherein said at least one active surface and at least one reference surface are SPR surfaces; and
   at least one prism connected to said at least one active surface and said at least one reference surface or a separate prism for each of said at least one active surface and said at least one reference surface.

9. A system comprising:
   a tip, comprising:
      at least one active surface having a surface chemistry with at least one functional group that allows it to form a covalent bond with at least one amine group of a ligand; and
      at least one reference surface having a surface chemistry that do not form a covalent bond with said at least one amine group of said ligand;
      wherein said functional groups of said active surface and said reference surface have similar non-specific binding properties;
      wherein said at least one functional group of said at least one active surface comprises a carboxylic group; and
      wherein said at least one functional group of said at least one reference surface comprises at least one functional group selected from the group consisting of sulfate, sulfonate, and phosphonate groups; and
   an optical sub-system functionally associated with said tip, comprising:

at least one light source;

illuminating optics to direct light from said at least one light source to reflect from said at least one active surface and said at least one reference surface at a range of angles of incidence;

a detector array associated with said at least one active surface and said at least one reference surface; and detecting optics to direct light reflected from said at least one active surface and said at least one reference surface to different elements of said detector array, according to an angle of reflectance of the light.

10. A method of manufacturing a tip for use in an optical detection system that analyzes an analyte in a fluid sample by bringing the fluid sample into the tip, binding the analyte to a ligand on a detection surface in the tip, and using light reflected from the detection surface to detect the analyte bound to it, the method comprising:

a) providing a first detection surface and a second detection surface;
b) applying a chemical treatment to said first detection surface, or applying different chemical treatments to said first detection surface and said second detection surface, such that said first detection surface, but substantially not the second detection surface, is capable of binding to a ligand that is capable of binding to said analyte, but said first detection surface and said second detection surface have surface chemistries that give them similar non-specific binding properties to said analyte and other materials in the fluid sample, wherein said first detection surface comprises at least one pre-active functional group;
c) assembling said first detection surface and said second detection surface into said tip;
d) incubating said first detection surface and said second detection surface with activating reagents to activate said at least one pre-active functional group, before adding said ligand.

11. The method of claim 10, wherein said at least one pre-active functional group comprises a carboxylic acid group.

12. The method of claim 11, wherein said activating reagents comprise EDC and/or NHS and/or sulfo-NHS.

13. The method of claim 12, further comprising exposing said first detection surface and said second detection surface to an excess of a molecule containing an amine group and a neutral group.

14. The method of claim 13, wherein said neutral group is selected from a group of epoxide, aldehyde, acrylate and disulfide.

15. The method of claim 10, wherein said assembling further comprises insertion of at least one prism into said tip, to be connected with said first detection surface and said second detection surface.

16. The method of claim 10, wherein said providing further comprises providing a tip with at least one integral prism, wherein said tip and said at least one integral prism are made from a transparent polymer.

* * * * *